United States Patent
Liew et al.

(10) Patent No.: US 11,788,092 B2
(45) Date of Patent: Oct. 17, 2023

(54) RECOMBINANT MICROORGANISMS AND USES THEREFOR

(71) Applicant: LanzaTech, Inc., Skokie, IL (US)

(72) Inventors: Fungmin Liew, Chicago, IL (US); Michael Koepke, Chicago, IL (US)

(73) Assignee: LanzaTech, Inc., Skokie, IL (US)

( * ) Notice: Subject to any disclaimer, the term of this patent is extended or adjusted under 35 U.S.C. 154(b) by 61 days.

(21) Appl. No.: 17/650,191

(22) Filed: Feb. 7, 2022

(65) Prior Publication Data

US 2022/0251573 A1    Aug. 11, 2022

Related U.S. Application Data

(60) Provisional application No. 63/147,108, filed on Feb. 8, 2021.

(51) Int. Cl.
| | |
|---|---|
| *C12N 15/52* | (2006.01) |
| *C12N 15/74* | (2006.01) |
| *C12P 7/42* | (2006.01) |
| *C12P 7/18* | (2006.01) |
| *C12N 9/00* | (2006.01) |
| *C12N 9/02* | (2006.01) |
| *C12N 9/04* | (2006.01) |
| *C12N 9/10* | (2006.01) |

(52) U.S. Cl.
CPC .......... *C12N 15/52* (2013.01); *C12N 9/0006* (2013.01); *C12N 9/0008* (2013.01); *C12N 9/1096* (2013.01); *C12N 9/93* (2013.01); *C12N 15/74* (2013.01); *C12P 7/18* (2013.01); *C12P 7/42* (2013.01); *C12Y 101/01001* (2013.01); *C12Y 102/01075* (2013.01); *C12Y 102/07005* (2013.01); *C12Y 206/01018* (2013.01); *C12Y 604/01002* (2013.01)

(58) Field of Classification Search
None
See application file for complete search history.

(56) References Cited

U.S. PATENT DOCUMENTS

| | | |
|---|---|---|
| 5,173,429 A | 12/1992 | Gaddy et al. |
| 5,593,886 A | 1/1997 | Gaddy |
| 6,368,819 B1 | 4/2002 | Gaddy et al. |
| 7,186,541 B2 | 3/2007 | Gokarn et al. |
| 7,972,824 B2 | 7/2011 | Simpson |
| 8,048,624 B1 | 11/2011 | Lynch |
| 8,293,509 B2 | 10/2012 | Simpson |
| 8,658,408 B2 | 2/2014 | Simpson |
| 8,900,836 B2 | 12/2014 | Simpson |
| 9,068,202 B2 | 6/2015 | Tran |
| 9,284,564 B2 | 3/2016 | Mueller |
| 9,347,076 B2 | 5/2016 | Liew |
| 9,359,611 B2 | 6/2016 | Koepke |
| 9,410,130 B2 | 8/2016 | Koepke |
| 9,738,875 B2 | 8/2017 | Koepke |
| 9,890,384 B2 | 2/2018 | Mueller |
| 9,994,878 B2 | 6/2018 | Koepke |
| 10,174,303 B2 | 1/2019 | Behrendorff |
| 10,590,406 B2 | 3/2020 | Koepke |
| 10,913,958 B2 | 2/2021 | Koepke |
| 2011/0003344 A1 | 1/2011 | Burk et al. |
| 2011/0008861 A1 | 1/2011 | Berry et al. |
| 2011/0125118 A1 | 5/2011 | Lynch |
| 2011/0129904 A1 | 6/2011 | Burgard et al. |
| 2011/0177564 A1 | 7/2011 | Stephanopoulos |
| 2011/0201068 A1 | 8/2011 | Pharkya et al. |
| 2011/0229947 A1 | 9/2011 | Zahn et al. |
| 2012/0041232 A1 | 2/2012 | Lynch |
| 2012/0045807 A1 | 2/2012 | Simpson |
| 2012/0064622 A1 | 3/2012 | Fischer et al. |
| 2012/0077236 A1 | 3/2012 | Gokarn et al. |
| 2012/0135481 A1 | 5/2012 | Jessen et al. |
| 2012/0244588 A1 | 9/2012 | Park et al. |
| 2012/0329110 A1 | 12/2012 | Kim |
| 2013/0157322 A1 | 6/2013 | Simpson |
| 2013/0288317 A1 | 10/2013 | Ramseier et al. |
| 2013/0323766 A1 | 12/2013 | Sillers et al. |
| 2017/0159083 A1 | 6/2017 | Valgepea |
| 2019/0185888 A1 | 6/2019 | Koepke |
| 2021/0292732 A1 | 9/2021 | Liew |

FOREIGN PATENT DOCUMENTS

| | | | |
|---|---|---|---|
| JP | 2012085635 | A | 5/2012 |
| WO | 200208438 | A2 | 1/2002 |
| WO | 2008028055 | A2 | 3/2008 |
| WO | 2009064200 | A2 | 5/2009 |
| WO | 2009089457 | A1 | 7/2009 |

(Continued)

OTHER PUBLICATIONS

Abrini, Arch Microbiol, 161: 345-351, 1994.
Agarkar, Production of 3-hydroxypropionate from biomass, Iowa State University, Thesis, 2007.
Alber, Birgit et al., Malonyl-Coenzyme A reductase in the modified 3-hydroxypropionate cycle for autotrophic carbon fixation in Archaeal Metallosphaera and Sulfolobus supp, Dec. 2006, vol. 188, No. 24, pp. 8551-8559.
Al-Hinai, Appl Environ Microbiol, 78: 8112-8121, 2012.
Argyros, Appl Environ Microbiol, 77: 8288-8294, 2011.
Berg, Appl Environ Microbiol, 77:1925-1936, 2011.

(Continued)

*Primary Examiner* — Kagnew H Gebreyesus

(57) ABSTRACT

Microorganisms are genetically engineered to produce 3-hydroxypropionate (3-HP). The microorganisms are carboxydotrophic acetogens. The microorganisms produce acetyl-coA using the Wood-Ljungdahl pathway for fixing $CO/CO_2$. A β-alanine pyruvate aminotransferase from a microorganism that contains such an enzyme is introduced. Additionally, an acetyl-coA carboxylase may also be introduced. The production of 3-HP can be improved. This can be effected by improved promoters or higher copy number or enzymes that are catalytically more efficient.

20 Claims, 19 Drawing Sheets

Specification includes a Sequence Listing.

(56) References Cited

FOREIGN PATENT DOCUMENTS

| WO | 2009111513 | A1 | 9/2009 |
|---|---|---|---|
| WO | 2012015317 | A1 | 2/2012 |
| WO | 2012019175 | A2 | 2/2012 |
| WO | 2012115527 | A2 | 8/2012 |
| WO | 2013043758 | A2 | 3/2013 |
| WO | 2013180581 | A1 | 12/2013 |

OTHER PUBLICATIONS

Chiba, Section 18: Diet Formulation and Common Feed Ingredients, Animal Nutrition Handbook, 3rd revision, pp. 575-633, 2014.
Collins, M. D., Lawson, P. A., Willems, A., Cordoba, J. J., Femandez-Garayzabal, J., Garcia, P., Cai, J., et al. The phylogeny of the genus *Clostridium*: proposal of five new genera and eleven new species combinations. International journal of systematic bacteriology, 44(4), 812-26(1994).
Drake, Acetogenic Prokaryotes, In: The Prokaryotes, 3rd edition, p. 354, New York, NY, 2006.
Heap, Nucl Acids Res, 40: e59,2012.
Herbert, M., O'Keeffe, T. a., Purdy, D., Elmore, M., & Minton, N. P. Gene transfer into Clostridium difficile CD630 and characterisation of its methylase genes. FEMS Microbiology Letters, 229(1), 103-110(2003).
Hugler M., et al., 2002, "Malonyl-coenzyme A reductase from Chloroflexus aurantiacus, a key enzyme of the 3-hydroxypropionate cycle for autotrophic CO(2) fixation", Journal of Bacteriology, vol. 184, pp. 2404-2410.
Ismail et al., J. Bacteriol, 1993, 175: 5079-5105.
Jennert, K. C., Tardif, C., Young, D. I., & Young, M. Gene transfer to Clostridium cellulolyticum ATCC 35319. Microbiology (Reading, England), 146 Pt 12, 3071-80(2000).
Karim et al. Synthetic Biology. 2020; 5(1): ysaa019.
Kita, A., Iwasaki, Y., Sakai, S., Okuto, S., Takaoka, K., Suzuki, T., Yano, S., et al. Development of genetic transformation and heterologous expression system in carboxydotrophic thermophilic acetogen Moorella thermoacetica. Journal of Bioscience and Bioengineering, vol. 115 (4) pp. 347-352 (2013).
Köpke, M., Mihalcea, C., Liew, F., Tizard, J. H., Ali, M. S., Conolly, J. J., Al-Sinawi, B., et al. 2,3-Butanediol Production By Acetogenic Bacteria, an Alternative Route To Chemical Synthesis, Using Industrial Waste Gas. Applied and environmental microbiology, 77(15), 5467-75(2011).
Köpke, Curr Opin Biotechnol, 22: 320-325, 2011.
Köpke & Dürre, Biochemical production of biobutanol, In: Handbook of biofuels production: processes and technologies (Eds.: Luque, Campelo & Clark), Woodhead Publishing Ltd, Camebridge, UK: 221-257 (2011).
Köpke, M., Held, C., Hujer, S., Liesegang, H., Wiezer, A., Wollherr, A., Ehrenreich, A., et al. Clostridium Ijungdahlii represents a microbial production platform based on syngas. Proceedings of the National Academy of Sciences of the United States of America, 107(29)(2010).
Kuehne, Strain Eng: Methods and Protocols, 389-407, 2011.
Leang, C., Ueki, T., Nevin, K. P., & Lovley, D. R. A Genetic System for Clostridium Ijungdahlii: A Chassis for Autotrophic Production of Biocommodities and a Model Homoacetogen. Applied and environmental microbiology, (Nov. 2012).
Liew, Frontiers Microbiol, 7: 694, 2016.
Menendez, C., et al., 1999, "Presence of acetyl coenzyme A (CoA) carboxylase and propionyl-CoA carboxylase in autotrophic Crenarchaeota and indication for operation of a 3-hydroxypropionate cycle in autotrophic carbon fixation", Journal of Bacteriology, vol. 181, No. 4, pp. 1088-1098.
Mermelstein, L. D., Welker, N. E., Bennett, G. N., & Papoutsakis, E. T. Expression of cloned homologous fermentative genes in Clostridium acetobutylicum ATCC 824. Bio/technology (Nature Publishing Company), 10(2), 190-195(1992).

Munasinghe et al. Biomass-derived syngas fermentation into biofuels: Opportunities and cahlenges., Bioresource Technology (2010), vol. 101, Issue 13, pp. 5013-5022.
Munk et al. "Complete genome sequence of Rhodospirillum rubrum type strain (S1T)," Standards in Genomic Sciences (2011) 4:293-302.
Murray, N.E. et al. (2000) Microbial. Molec. Biol. Rev. 64, 412.
Nagaraju, Biotechnol Biofuels, 9: 219, 2016.
NCBI Reference Sequence: YP_001636995.1, acetyl-CoA carboxylase, biotin carboxylase [Chloroflexus aurantiacus J-10-fl], initial submission on Dec. 5, 2007 by Copeland, A., et al., US DOE Joint Genome Institute, 2800.
Ng, PLoS One, 8: e56051, 2013.
Ohshima, Bulletin of Kyoto University of Education, Ser, B, Nos. 71/72, pp. 17-21, 1998.
Perez, Biotechnol Bioeng, 110:1066-1077, 2012.
Ragsdale, Biochim Biophys Acta, 1784: 1873-1898, 2008.
Ravcheev et al. "Comparative genomic analysis of regulation of anaerobic respiration in ten genomes from three families of gamma-proteobacteria (Enterobacteriaceae, Pasteurellaceae, Vibrionaceae)," BMC Genomics 2007, 8:54 doi:10.1186/1471-2164-8-54, Feb. 21, 2007.
Strätz, M., Sauer, U., Kuhn, a, & Durre, P. Plasmid Transfer into the Homoacetogen Acetobacterium woodii by Electroporation and Conjugation. Applied and environmental microbiology, 60(3), 1033-7(1994).
Tang, K.H., et al. 2011, "Complete genome sequence of the filamentous anoxygenic phototrophic bacterium Chloroflexus aurantiacus," BMC Genomics, vol. 12, pp. 334-334.
Tanner, Int J System Bacteriol, 43:232-236, 1993.
Tirado-Acevedo O. Production of Bioethanol from Synthesis Gas Using Clostridium Ijungdahlii. PhD thesis, North Carolina State University, 2010.
Tyurin, Michael, & Kiriukhin, M. Electrofusion of cells of *Acetogen Clostridium* sp. MT 351 with erm (B) or cat in the chromosome. Journal of Biotech, 1-12(2012).
Tyurin, MV, Desai, S., & Lynd, L. Electrotransformation of Clostridium thermocellum. Applied and environmental mnictrobiology 70(2), 883-890(2004).
Ueki, mBio, 5: e01636-01614, 2014.
Williams, D. R., Young, D. L, & Young, M. Conjugative plasmid transfer from *Escherichia coli* to Clostridium acetobutylicum. Journal of general microbiology, 136(5), 819-26(1990).
Zarzycki, J., et al., 2011, "Coassimilation of organic substrates via the autotrophic 3-hydroxypropionate bi-cycle in Chloroflexus aurantiacus", Applied and Environmental Microbiology, vol. 77, No. 17, pp. 6181-6188.
Zhang, Construction of a recombinant E. coli could produce 3-hydroxypropionic acid via 3-hydroxypropionic acid pathway, Beijing Science and Technology University, Thesis, 2009 (with Abstract in English translation).
Zhang, Journal Microbiol Methods, 108: 49-60, 2015.
Chinese Patent Application No. 2013800407933, Chinese Patent Office, Office Action dated Aug. 22, 2016.
Office Action, Japanese Patent Application No. 2015-514947, Japanese Patent Office, dated Mar. 21, 2017.
Sambrook J, Fritsch EF, Maniatis T: Molecular Cloning: A laboratory Manual, Cold Spring Harbour Laboratory Press, Cold Spring Harbour, 1989.
Borodina et al. "Establishing a synthetic pathway for high-level production of 3-hydroxypropionic acid in *Saccharomyces cerevisiae* via β-alanine," Metabolic Engineering 27 (2015) 57-64 (Available Online Oct. 23, 2014).
Yin et al., "An extended bacterial reductive pyrimidine degradation pathway that enables nitrogen release from β-alanine," J. Biol. Chem., 2019, vol. 294, No. 43, pp. 15662-15671.
International Search Report and Written Opinion issued in International Application No. PCT/US2022/015493, dated May 31, 2022, 11 pages.
Kumar et al., "Recent Advances in Biological Production of 3-hydropropionic acid", Biotechnology Advances 31 (2013) 945-961.

(56) References Cited

OTHER PUBLICATIONS

Liu et al. "Fermentative production of ethanol from syngas using novel moderately alkaliphilic strains of Alkalibaculum bacchi" Bioresource Technology, vol. 104, Jan. 2012, pp. 336-341.

Rathnasingh et al., "Production of 3-hydroxypropionic acid via malonyl-CoA pathway using recombinant *Escherichia coli* strains," Journal of Biotechnology 157 (2012) 633-640.

Sauer et al., "Microbial production of organic acids: expanding the markets," Trends in Biotechnology, vol. 26, No. 2, 2008, p. 100-108.

Schiel-Bengelsdorf et al. "Pathway engineering and synthetic biology using acetogens" FEBS Letters 586 (2012) 2191-2198.

Tijssen, Laboratory techniques in biochemistry and molecular biology-hybridization with nucleic acid probes, Second Chapter "Overview of principles of hybridization and the strategy of nucleic acid probe assay," Elsevier, N.Y, 1993.

US 11,788,092 B2

RECOMBINANT MICROORGANISMS AND USES THEREFOR

CROSS REFERENCE TO RELATED APPLICATIONS

This application claims the benefit of U.S. Provisional Patent Application No. 63/147,108, filed Feb. 8, 2021, the entirety of which is incorporated herein by reference.

GOVERNMENT RIGHTS

This disclosure was made with government support under Cooperative Agreement DE-SC0019090 awarded by the Department of Energy. The government has certain rights in the invention.

FIELD OF THE DISCLOSURE

This disclosure relates to recombinant microorganisms and methods for the production of 3-Hydroxypropionate [3-HP] by microbial fermentation of a substrate comprising CO and/or $CO_2$.

BACKGROUND

3-Hydroxypropionate [3-HP] is a platform chemical, acting as precursor for production of polymer materials and as chemical feedstock. Poly(3-hydroxypropionicacid) [P(3-HP)] is a biodegradable polymer with promising characteristics such as unusual high heat stability.

3-HP can be used to derive a number of valuable industrial chemicals including: acrylic acid which is used in the manufacture of paint, paper, adhesives, textiles, speciality coatings, ink, and superabsorbent polymer polyacrylates; 1,3-propanediol which is of use as a solvent, adhesive, cosmetic, or to make polytrimethylene terephthalate used in carpet and textiles; 3-hydroxypropionaldehyde which is used in the preparation of foods, as a feed additive, and as a preservative in the nutritional industry.

3-HP is listed as third most important renewable chemical by the U.S. Department of Energy and a global market opening for 3-HP has been estimated to be 3.63 million tons per year (Sauer et al, 2008, Bozell et al, 2010, US DOE report: 48-49).

It is an object of the disclosure to provide recombinant microorganisms and a method for the production of 3-HP by microbial fermentation which may provide one or more advantages over known methods, or to at least to provide the public with a useful choice.

SUMMARY

The disclosure generally provides, inter alia, methods for the production of 3-HP by microbial fermentation of a substrate comprising CO and/or $CO_2$, and recombinant microorganisms of use in such methods. It combines two different $CO_2$ fixation pathways to produce a single metabolic product.

In a first aspect, the disclosure provides an anaerobic acetogenic recombinant microorganism capable of producing 3-HP and optionally one or more other products by fermentation of a substrate comprising CO and/or $CO_2$.

In one particular embodiment, the microorganism is adapted to express one or more enzymes (or one or more subunits thereof) in the 3-HP biosynthesis pathway which enzymes are not naturally present in a parental microorganism from which the recombinant microorganism is derived. In another embodiment, the microorganism is adapted to over-express one or more enzymes (or one or more subunits thereof) in the 3-HP biosynthesis pathway, which enzymes are naturally present in a parental microorganism from which the recombinant microorganism is derived. In one embodiment, the microorganism is adapted to express one or more enzymes (or one or more subunits thereof) in the 3-HP-biosynthesis pathway which are not naturally present in a parental microorganism and over-express one or more enzymes (or one or more subunits thereof) in the 3-HP biosynthesis pathway which are naturally present in a parental microorganism.

In one embodiment, the one or more enzymes are chosen from the group consisting of: β-alanine pyruvate aminotransferase (BAPAT) (EC 2.6.1.19); malonic semialdehyde reductase (MSR) (EC 1.1.1.59 and EC 1.1.1.295); Acetyl-CoA Carboxylase (ACC) (EC 6.4.1.2); and a functionally equivalent variant of any one thereof.

In one embodiment, the parental microorganism is capable of fermenting a substrate comprising CO and/or $CO_2$ to produce Acetyl-CoA but not of converting Acetyl-CoA to 3-HP and the recombinant microorganism is adapted to express one or more enzymes (or one or more subunits thereof) involved in the conversion of Acetyl-CoA to 3-HP.

In one embodiment, the microorganism comprises one or more exogenous nucleic acids adapted to increase expression of one or more nucleic acids native to the parental microorganism and which one or more nucleic acids encode one or more of the enzymes (or one or more subunits thereof) referred to herein before.

In one embodiment, the one or more exogenous nucleic acid adapted to increase expression is a regulatory element. In one embodiment, the regulatory element is a promoter.

In one embodiment, the promoter is a constitutive promoter. In one embodiment, the promoter is selected from the group comprising Wood-Ljungdahl gene cluster or Phosphotransacetylase/Acetate kinase operon promoters.

In one embodiment, the microorganism comprises one or more exogenous nucleic acids encoding and adapted to express one or more of the enzymes (or one or more subunits thereof) referred to herein before. In one embodiment, the microorganisms comprise one or more exogenous nucleic acid encoding and adapted to express at least two of the enzymes (or one or more subunits thereof).

In one embodiment, the one or more exogenous nucleic acid is a nucleic acid construct or vector, in one particular embodiment a plasmid, encoding one or more of the enzymes referred to hereinbefore in any combination.

In one embodiment, the exogenous nucleic acid is an expression plasmid.

In one embodiment, the parental microorganism is selected from the group of anaerobic acetogens.

In one particular embodiment, the parental microorganism is selected from the group of carboxydotrophic acetogenic bacteria, in one embodiment from the group comprising *Clostridium autoethanogenum, Clostridium ljungdahlii, Clostridium ragsdalei, Clostridium carboxidivorans, Clostridium drakei, Clostridium scatologenes, Clostridium aceticum, Clostridium formicoaceticum, Clostridium magnum, Butyribacterium methylotrophicum, Acetobacterium woodii, Alkalibaculum bacchii, Blautia producta, Eubacterium limosum, Moorella thermoacetica, Moorella thermautotrophica, Sporomusa ovata, Sporomusa silvacetica, Sporomusa sphaeroides, Oxobacter pfennigii,* and *Thermoanaerobacter kivui.*

In one embodiment the parental microorganism is *Clostridium autoethanogenum* or *Clostridium ljungdahlii*. In one particular embodiment, the microorganism is *Clostridium autoethanogenum* DSM23693. In another particular embodiment, the microorganism is *Clostridium ljungdahlii* DSM13528 (or ATCC55383).

In one embodiment, the parental microorganism lacks one or more genes encoding β-alanine pyruvate aminotransferase and/or Acetyl-CoA carboxylase, or one or more subunits thereof.

In a second aspect, the disclosure provides a nucleic acid encoding one or more enzymes (or one or more subunits thereof) which when expressed in a microorganism allows the microorganism to produce 3-HP by fermentation of substrate comprising CO and/or $CO_2$.

In one embodiment, the nucleic acid encodes two or more enzymes (or one or more subunits thereof) which when expressed in a microorganism allows the microorganism to produce 3-HP by fermentation of substrate comprising CO.

In one embodiment, the enzymes are chosen from β-alanine pyruvate aminotransferase and Acetyl CoA carboxylase, and a functionally equivalent variant of any one or more thereof.

In one embodiment, the nucleic acid comprises nucleic acid sequences encoding β-alanine pyruvate aminotransferase, Acetyl CoA carboxylase, or a functionally equivalent variant of any one or more thereof, in any order.

In one embodiment, the nucleic acid encoding β-alanine pyruvate aminotransferase has the sequence of SEQ ID NO: 13, or is a functionally equivalent variant thereof. In one embodiment, the nucleic acid encoding β-alanine pyruvate aminotransferase has the sequence of SEQ ID NO: 14, or is a functionally equivalent variant thereof. In one embodiment, the nucleic acid encoding β-alanine pyruvate aminotransferase has the sequence of SEQ ID NO: 15, or is a functionally equivalent variant thereof.

In one embodiment, the nucleic acids of the disclosure further comprise a promoter. In one embodiment, the promoter allows for constitutive expression of the genes under its control. In a particular embodiment a Wood-Ljungdahl cluster promoter is used. In another particular embodiment, a Phosphotransacetylase/Acetate kinase operon promoter is used. In one particular embodiment, the promoter is from *C. autoethanogenum*.

In a third aspect, the disclosure provides a nucleic acid construct or vector comprising one or more nucleic acid of the second aspect.

In one particular embodiment, the nucleic acid construct or vector is an expression construct or vector. In one particular embodiment, the expression construct or vector is a plasmid.

In a fourth aspect, the disclosure provides host organisms comprising any one or more of the nucleic acids of the seventh aspect or vectors or constructs of the third aspect.

In a fifth aspect, the disclosure provides a composition comprising an expression construct or vector as referred to in the third aspect of the disclosure and a methylation construct or vector.

Preferably, the composition is able to produce a recombinant microorganism according to the first aspect of the disclosure.

In one particular embodiment, the expression construct/vector and/or the methylation construct/vector is a plasmid.

In a sixth aspect, the disclosure provides a method for the production of 3-HP, and optionally one or more other products, by microbial fermentation comprising fermenting a substrate comprising CO and/or $CO_2$ using a recombinant microorganism of the first aspect of the disclosure.

In one embodiment the method comprises the steps of:
(a) providing a substrate comprising CO and/or $CO_2$ to a bioreactor containing a culture of one or more microorganism of the first aspect of the disclosure; and
(b) anaerobically fermenting the culture in the bioreactor to produce 3-HP.

In one embodiment the method comprises the steps of:
(a) capturing CO- and/or $CO_2$-containing gas produced as a result of the industrial process, before the gas is released into the atmosphere;
(b) the anaerobic fermentation of the CO- and/or $CO_2$-containing gas to produce at least 3-HP by a culture containing one or more microorganism of the first aspect of the disclosure.

In particular embodiments of the method aspects, the microorganism is maintained in an aqueous culture medium.

In particular embodiments of the method aspects, the fermentation of the substrate takes place in a bioreactor.

Preferably, the substrate comprising CO and/or $CO_2$ is a gaseous substrate comprising CO and/or $CO_2$. In one embodiment, the substrate comprises an industrial waste gas. In certain embodiments, the gas is steel mill waste gas or syngas.

In a particular embodiment, the substrate is a substrate comprising CO.

In embodiments of the disclosure where the substrate comprises $CO_2$, but no CO, the substrate preferably also comprises $H_2$.

In one embodiment, the substrate comprises CO and $CO_2$. In one embodiment, the substrate comprises $CO_2$ and $H_2$. In another embodiment, the substrate comprises CO, $CO_2$, and $H_2$.

In one embodiment, the substrate will typically contain a major proportion of CO, such as at least about 20% to about 100% CO by volume, from 20% to 70% CO by volume, from 30% to 60% CO by volume, and from 40% to 55% CO by volume. In particular embodiments, the substrate comprises about 25%, or about 30%, or about 35%, or about 40%, or about 45%, or about 50% CO, or about 55% CO, or about 60% CO by volume.

In certain embodiments the methods further comprise the step of recovering 3-HP and optionally one or more other products from the fermentation broth.

In a seventh aspect, the disclosure provides 3-HP when produced by the method of the sixth aspect.

In another aspect, the disclosure provides a method for the production of a microorganism of the first aspect of the disclosure comprising transforming a parental microorganism with one or more exogenous nucleic acid such that the microorganism is capable of producing 3-HP, and optionally one or more other products, by fermentation of a substrate comprising CO and/or $CO_2$, wherein the parental microorganism is not capable of producing 3-HP by fermentation of a substrate comprising CO and/or $CO_2$.

In one particular embodiment, a parental microorganism is transformed with one or more exogenous nucleic acid adapted to express one or more enzymes in the 3-HP biosynthesis pathway which are not naturally present in the parental microorganism. In another embodiment, a parental microorganism is transformed with one or more nucleic acid adapted to over-express one or more enzymes in the 3-HP biosynthesis pathway which are naturally present in the parental microorganism. In another embodiment, a parental microorganism is transformed with one or more exogenous nucleic acid adapted to express one or more enzymes in the 3-HP biosynthesis pathway which are not naturally present in the parental microorganism and over-express one or more enzymes in the 3-HP biosynthesis pathway which are naturally present in the parental microorganism.

In certain embodiments, the one or more enzymes are as herein before described.

In certain embodiment, the parental microorganism is as herein before described.

According to one embodiment a process is provided for converting CO or $CO_2$ into 3-hydroxypropionate (3-HP). A gaseous CO-containing and/or $CO_2$-containing substrate is passed to a bioreactor containing a culture of carboxydotrophic, acetogenic bacteria in a culture medium such that the bacteria convert the CO and/or $CO_2$ to 3-HP. The carboxydotrophic acetogenic bacteria are genetically engineered to express a β-alanine pyruvate aminotransferase. They also express an acetyl-CoA carboxylase, whether native or exogenous. The 3-HP is recovered from the bioreactor.

According to another embodiment an isolated, genetically engineered, carboxydotrophic, acetogenic bacterium is provided that comprises a nucleic acid encoding a β-alanine pyruvate aminotransferase. The nucleic acid is exogenous to the host bacteria. The bacteria express the β-alanine pyruvate aminotransferase and the bacteria acquire the ability to generate malonic semialdehyde via transamination reaction with pyruvate and β-alanine. The β-alanine pyruvate aminotransferase is typically at least 85% identical to the amino acid sequence encoded by the nucleotide sequence of SEQ ID NO: 13. The β-alanine pyruvate aminotransferase is typically at least 85% identical to the amino acid sequence encoded by the nucleotide sequence of SEQ ID NO: 14. The β-alanine pyruvate aminotransferase is typically at least 85% identical to the amino acid sequence encoded by the nucleotide sequence of SEQ ID NO: 15. In one embodiment, β-alanine pyruvate aminotransferase is selected because pyruvate is a central metabolite and a co-factor providing distinct advantages, such as driving enzymatic flux.

The bacteria may further comprise an exogenous nucleic acid encoding acetyl-Coenzyme A carboxylase. The nucleic acid may be operably linked to a promoter. The nucleic acid may have been codon optimized. The nucleic acid or the encoded carboxylase may be from a nonsulfur, photosynthetic bacterium. The bacteria may be selected from the group consisting of *Clostridium autoethanogenum*, *Clostridium ljungdahlii*, *Clostridium ragsdalei*, *Clostridium carboxidivorans*, *Clostridium drakei*, *Clostridium scatologenes*, *Clostridium aceticum*, *Clostridium formicoaceticum*, *Clostridium magnum*, *Butyribacterium methylotrophicum*, *Acetobacterium woodii*, *Alkalibaculum bacchii*, *Blautia producta*, *Eubacterium limosum*, *Moorella thermoacetica*, *Moorella thermautotrophica*, *Sporomusa ovata*, *Sporomusa silvacetica*, *Sporomusa sphaeroides*, *Oxobacter pfennigii*, and *Thermoanaerobacter kivui*. The donor bacterium of the exogenous nucleic acid may be a nonsulfur, photosynthetic bacterium such as, *Chloroflexus aurantiacus*, *Metallosphaera*, and *Sulfolobus* spp.

The genetically engineered bacteria may be cultured by growing in a medium comprising a gaseous carbon source. The carbon source may comprise CO and/or $CO_2$, which may be used as either or both of an energy source or a carbon source. The bacteria may optionally be grown under strictly anaerobic conditions. The carbon source may comprise an industrial waste product or off-gas.

The disclosure may also be said broadly to consist in the parts, elements and features referred to or indicated in the specification of the application, individually or collectively, in any or all combinations of two or more of said parts, elements or features, and where specific integers are mentioned herein which have known equivalents in the art to which the disclosure relates, such known equivalents are deemed to be incorporated herein as if individually set forth.

BRIEF DESCRIPTION OF THE DRAWINGS

These and other aspects of the present disclosure, which should be considered in all its novel aspects, will become apparent from the following description, which is given by way of example only, with reference to the accompanying figures, in which:

FIG. 2A: Growth profile; FIG. 2B: Peak Biomass. Unc=Unchallenged; N=2; Error bar=S.D.

FIG. 5A: End-point 3-HP titer; FIG. 5B: Biomass concentration;

FIG. 5C: 3-HP titer normalized by biomass concentration; Incubation duration=8 days.

FIG. 7A: Biomass and metabolite profile analyzed by HPLC; FIG. 7B: gas profile analyzed by GC-TCD (negative=uptake); FIG. 7C: 3-HP and 1,3-PDO profile analyzed by LC-MS and GC-MS, respectively.

FIG. 8A: Biomass and metabolite profile analyzed by HPLC; FIG. 8B: gas profile analyzed by GC-TCD (negative=uptake); FIG. 8C: 3-HP and 1,3-PDO profile analyzed by LC-MS and GC-MS, respectively.

FIG. 9A: Biomass and metabolite profile analyzed by HPLC; FIG. 9B: gas profile analyzed by GC-TCD (negative=uptake); FIG. 9C: 3-HP and 1,3-PDO profile analyzed by LC-MS and GC-MS, respectively.

FIG. 10A: Biomass and metabolite profile analyzed by HPLC; FIG. 10B: gas profile analyzed by GC-TCD (negative=uptake); FIG. 10C: 3-HP and 1,3-PDO profile analyzed by LC-MS and GC-MS, respectively. D=dilution rate/day.

DETAILED DESCRIPTION

The following description of embodiments is given in general terms. The disclosure is further elucidated from the disclosure given under the heading "Examples" herein below, which provides experimental data supporting the disclosure, specific examples of various aspects of the disclosure, and means of performing the disclosure.

The inventors have surprisingly been able to engineer a carboxydotrophic acetogenic microorganism to 3-Hydroxypropionate (3-HP) by fermentation of a substrate comprising CO and/or $CO_2$. This offers an alternative means for the production of 3-HP which may have benefits over the current methods for the production of 3-HP. In addition, it offers a means of using carbon monoxide from industrial processes which would otherwise be released into the atmosphere and pollute the environment. In this disclosure, a microorganism expresses enzymes from the beta-alanine pathway, which resulted in significantly higher titer and productivity of 3-HP from a gaseous substrate.

Figure 1:
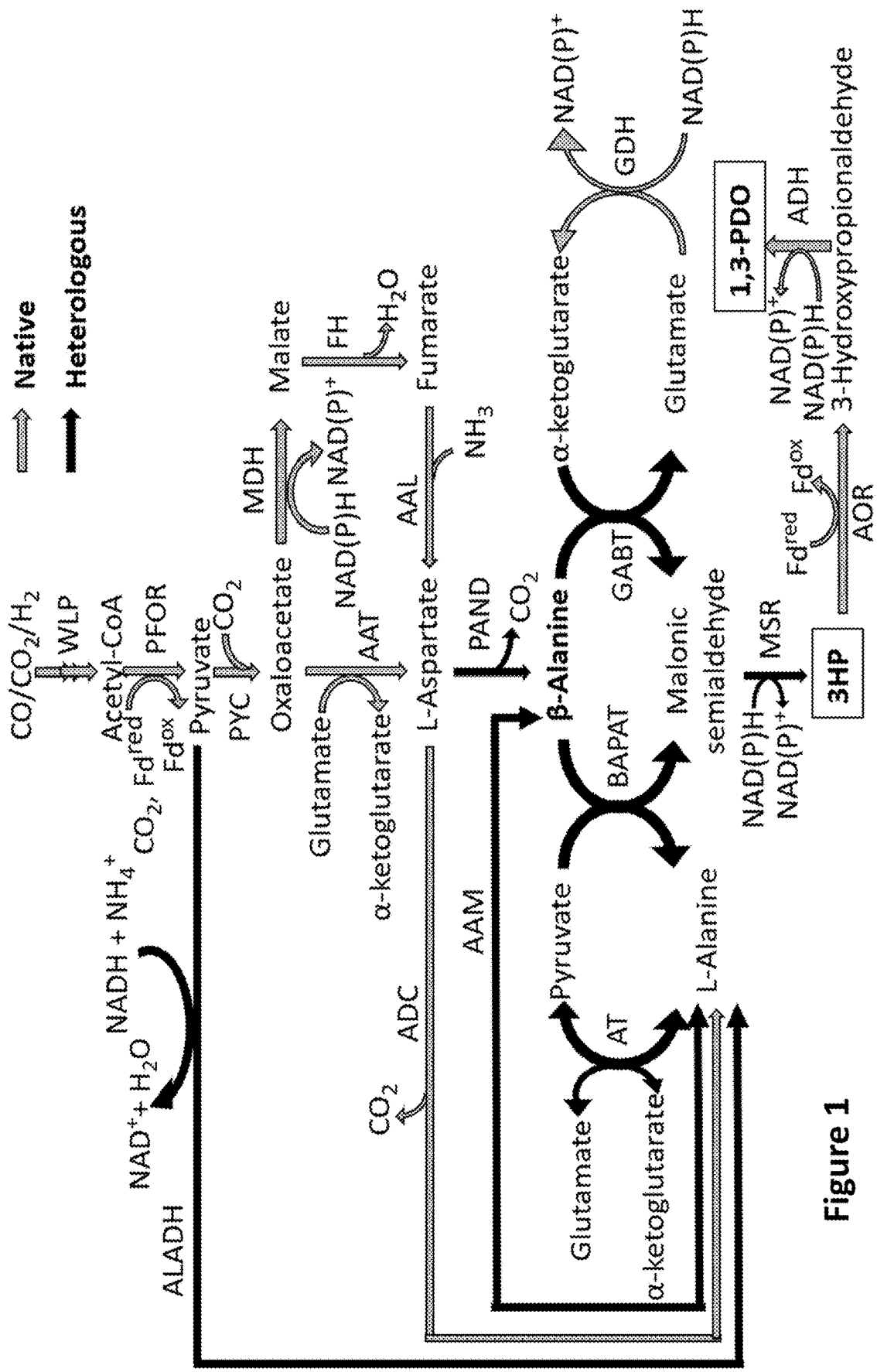
FIG. 1 shows the metabolic pathway leading to the biosynthesis of 3-hydroxypropionic acid (3-HP) and 1,3-propanediol (1,3-PDO) by *Clostridium autoethanogenum* from gas fermentation. Enzymatic steps that require heterologous expression are shown in black while native reactions are shown in grey. Carbon and hydrogen is assimilated to acetyl-CoA by the Wood-Ljungdahl pathway (WLP) which is then converted to pyruvate by a pyruvate::ferredoxin oxidoreductase (PFOR). Through the actions of pyruvate carboxylase (PYC), malate dehydrogenase (MDH), fumarate hydratase (FH), aspartate ammonia-lyase (AAL), and aspartate aminotransferase (AAT), L-aspartate is formed. Aspartate-4-decarboxylase (ADC) then converts L-aspartate to L-alanine. The key pathway intermediate β-alanine can be synthesized from L-aspartate through heterologous expression of aspartate-1-decarboxylase (PAND), or from L-alanine via 2,3-alanine aminomutase (AAM). Alanine dehydrogenase (ALADH) can be heterologous expressed to convert pyruvate to L-alanine. β-alanine pyruvate aminotransferase (BAPAT) and/or γ-aminobutyrate transaminase (GABT) can then convert β-alanine to malonic semialdehyde, which is then reduced to 3-HP via malonic semialdehyde (MSR). Alanine transaminase (AT) can be heterologously expressed to convert L-alanine to pyruvate for BAPAT reaction. Glutamate dehydrogenase (GDH) can be heterologously expressed to convert glutamate to α-ketoglutarate for GABT reaction. From 3-HP, 1,3-PDO can be generated via the action of aldehyde::ferredoxin oxidoreductase (AOR) and alcohol dehydrogenase (ADH). NAD(P)H comprises NADPH and NADH.

In engineering the microorganisms of the disclosure, the inventors have surprisingly been able to combine two separate $CO_2$ fixation pathways, as illustrated in FIG. 1. This provides for sustainable fermentation to produce 3-HP using a substrate comprising CO and/or a substrate comprising $CO_2$. Two pathways fixing $CO_2$ are thus linked to produce a desired product.

In one embodiment, the disclosure describes fixation of three molecules of $CO_2$ into one molecule of 3-HP by combining two separate $CO_2$ fixation pathways (FIG. 1), the Wood-Ljungdahl pathways of acetogens that allows fixation of two molecules of $CO_2$, and the initial carbon fixation steps of the 3-HP cycle allows fixation of another molecule of $CO_2$. $CO_2$ could also be replaced with CO, as the key enzyme of the Wood-Ljungdahl pathway, a CO dehydrogenase (CODH) is able to convert CO into $CO_2$ and energy in a biological water gas shift reaction ($CO+H_2O<->CO_2+H_2$). Any mixture of CO and $CO_2$ can be used. When $CO_2$ alone is used, energy in form of hydrogen or electricity may need to be supplied, while CO can serve as both carbon and energy source.

While the inventors have demonstrated the efficacy of the disclosure in *Clostridium autoethanogenum*, the disclosure is applicable to the wider group of anaerobic acetogenic microorganisms and fermentation on substrates comprising CO and/or $CO_2$, as discussed above and further herein.

Unless otherwise defined, the following terms as used throughout this specification are defined as follows:

The terms "increasing the efficiency," "increased efficiency," and the like, when used in relation to a fermentation process, include, but are not limited to, increasing one or more of the rate of growth of microorganisms catalyzing the fermentation, the growth and/or product production rate at elevated product concentrations, increasing the volume of desired product produced per volume of substrate consumed, increasing the rate of production or level of production of the desired product, increasing the relative proportion of the desired product produced compared with other byproducts of the fermentation, decreasing the amount of water consumed by the process, and decreasing the amount of energy utilized by the process.

The term "fermentation" should be interpreted as a metabolic process that produces chemical changes in a substrate. For example, a fermentation process receives one or more substrates and produces one or more products through utilization of one or more microorganisms. The term "fermentation," "gas fermentation" and the like should be interpreted as the process which receives one or more substrate, such as syngas produced by gasification and produces one or more product through the utilization of one or more C1-fixing microorganism. Preferably the fermentation process includes the use of one or more bioreactor. The fermentation process may be described as either "batch" or "continuous". "Batch fermentation" is used to describe a fermentation process where the bioreactor is filled with raw material, e.g. the carbon source, along with microorganisms, where the products remain in the bioreactor until fermentation is completed. In a "batch" process, after fermentation is completed, the products are extracted, and the bioreactor is cleaned before the next "batch" is started. "Continuous fermentation" is used to describe a fermentation process where the fermentation process is extended for longer periods of time, and product and/or metabolite is extracted during fermentation. Preferably the fermentation process is continuous.

The term "non-naturally occurring" when used in reference to a microorganism is intended to mean that the microorganism has at least one genetic modification not found in a naturally occurring strain of the referenced species, including wild-type strains of the referenced species. Non-naturally occurring microorganisms are typically developed in a laboratory or research facility.

The terms "genetic modification," "genetic alteration," or "genetic engineering" broadly refer to manipulation of the genome or nucleic acids of a microorganism by the hand of man. Likewise, the terms "genetically modified," "genetically altered," or "genetically engineered" refers to a microorganism containing such a genetic modification, genetic alteration, or genetic engineering. These terms may be used to differentiate a lab-generated microorganism from a naturally-occurring microorganism. Methods of genetic modification of include, for example, heterologous gene expression, gene or promoter insertion or deletion, nucleic acid mutation, altered gene expression or inactivation, enzyme engineering, directed evolution, knowledge-based design, random mutagenesis methods, gene shuffling, and codon optimization.

Metabolic engineering of microorganisms, such as Clostridia, can tremendously expand their ability to produce many important fuel and chemical molecules other than native metabolites, such as ethanol. However, until recently, Clostridia were considered genetically intractable and therefore generally off limits to extensive metabolic engineering efforts. In recent years several different methods for genome engineering for Clostridia have been developed including intron-based methods (ClosTron) (Kuehne, *Strain Eng: Methods and Protocols*, 389-407, 2011), allelic exchange methods (ACE) (Heap, *Nucl Acids Res*, 40: e59, 2012; Ng, *PLoS One*, 8: e56051, 2013), Triple Cross (Liew, *Frontiers Microbiol*, 7: 694, 2016), methods mediated through I-SceI (Zhang, *Journal Microbiol Methods*, 108: 49-60, 2015), MazF (Al-Hinai, *Appl Environ Microbiol*, 78: 8112-8121, 2012), or others (Argyros, *Appl Environ Microbiol*, 77: 8288-8294, 2011), Cre-Lox (Ueki, mBio, 5: e01636-01614, 2014), and CRISPR/Cas9 (Nagaraju, Biotechnol Biofuels, 9: 219, 2016). However, it remains extremely challenging to iteratively introduce more than a few genetic changes, due to slow and laborious cycling times and limitations on the transferability of these genetic techniques across species. Furthermore, we do not yet sufficiently understand C1 metabolism in Clostridia to reliably predict modifications that will maximize C1 uptake, conversion, and carbon/energy/redox flows towards product synthesis. Accordingly, introduction of target pathways in Clostridia remains a tedious and time-consuming process.

"Recombinant" indicates that a nucleic acid, protein, or microorganism is the product of genetic modification, engineering, or recombination. Generally, the term "recombinant" refers to a nucleic acid, protein, or microorganism that contains or is encoded by genetic material derived from multiple sources, such as two or more different strains or species of microorganisms.

"Wild type" refers to the typical form of an organism, strain, gene, or characteristic as it occurs in nature, as distinguished from mutant or variant forms.

"Endogenous" refers to a nucleic acid or protein that is present or expressed in the wild-type or parental microorganism from which the microorganism of the disclosure is derived. For example, an endogenous gene is a gene that is natively present in the wild-type or parental microorganism from which the microorganism of the disclosure is derived. In one embodiment, the expression of an endogenous gene may be controlled by an exogenous regulatory element, such as an exogenous promoter.

"Exogenous" refers to a nucleic acid or protein that originates outside the microorganism of the disclosure. For example, an exogenous gene or enzyme may be artificially or recombinantly created and introduced to or expressed in the microorganism of the disclosure. An exogenous gene or enzyme may also be isolated from a heterologous microorganism and introduced to or expressed in the microorganism of the disclosure. Exogenous nucleic acids may be adapted to integrate into the genome of the microorganism of the disclosure or to remain in an extra-chromosomal state in the microorganism of the disclosure, for example, in a plasmid.

"Heterologous" refers to a nucleic acid or protein that is not present in the wild-type or parental microorganism from which the microorganism of the disclosure is derived. For example, a heterologous gene or enzyme may be derived from a different strain or species and introduced to or expressed in the microorganism of the disclosure. The heterologous gene or enzyme may be introduced to or expressed in the microorganism of the disclosure in the form in which it occurs in the different strain or species. Alternatively, the heterologous gene or enzyme may be modified in some way, e.g., by codon-optimizing it for expression in the microorganism of the disclosure or by engineering it to alter function, such as to reverse the direction of enzyme activity or to alter substrate specificity.

The terms "polynucleotide," "nucleotide," "nucleotide sequence," "nucleic acid," and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides or nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene products."

The terms "polypeptide", "peptide," and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein, the term "amino acid" includes natural and/or unnatural or synthetic amino acids, including glycine and both the D or L optical isomers, and amino acid analogs and peptidomimetics.

"Enzyme activity," or simply "activity," refers broadly to enzymatic activity, including, but not limited to, the activity of an enzyme, the amount of an enzyme, or the availability of an enzyme to catalyze a reaction. Accordingly, "increasing" enzyme activity includes increasing the activity of an enzyme, increasing the amount of an enzyme, or increasing the availability of an enzyme to catalyze a reaction. Similarly, "decreasing" enzyme activity includes decreasing the activity of an enzyme, decreasing the amount of an enzyme, or decreasing the availability of an enzyme to catalyze a reaction.

"Mutated" refers to a nucleic acid or protein that has been modified in the microorganism of the disclosure compared to the wild-type or parental microorganism from which the microorganism of the disclosure is derived. In one embodiment, the mutation may be a deletion, insertion, or substitution in a gene encoding an enzyme. In another embodiment, the mutation may be a deletion, insertion, or substitution of one or more amino acids in an enzyme.

In particular, a "disruptive mutation" is a mutation that reduces or eliminates (i.e., "disrupts") the expression or activity of a gene or enzyme. The disruptive mutation may partially inactivate, fully inactivate, or delete the gene or enzyme. The disruptive mutation may be any mutation that reduces, prevents, or blocks the biosynthesis of a product produced by an enzyme. The disruptive mutation may be a knockout (KO) mutation. The disruption may also be a knockdown (KD) mutation that reduces, but does not entirely eliminate, the expression or activity of a gene, protein, or enzyme. While KOs are generally effective in increasing product yields, they sometimes come with the penalty of growth defects or genetic instabilities that outweigh the benefits, particularly for non-growth coupled products. The disruptive mutation may include, for example, a mutation in a gene encoding an enzyme, a mutation in a genetic regulatory element involved in the expression of a gene encoding an enzyme, the introduction of a nucleic acid which produces a protein that reduces or inhibits the activity of an enzyme, or the introduction of a nucleic acid (e.g., antisense RNA, siRNA, CRISPR) or protein which inhibits the expression of an enzyme. The disruptive mutation may be introduced using any method known in the art.

Introduction of a disruptive mutation results in a microorganism of the disclosure that produces no target product or substantially no target product or a reduced amount of target product compared to the parental microorganism from which the microorganism of the disclosure is derived. For example, the microorganism of the disclosure may produce no target product or at least about 1%, 3%, 5%, 10%, 20%, 30%, 40%, 50%, 60%, 70%, 80%, 90%, or 95% less target product than the parental microorganism. For example, the microorganism of the disclosure may produce less than about 0.001, 0.01, 0.10, 0.30, 0.50, or 1.0 g/L target product.

"Codon optimization" refers to the mutation of a nucleic acid, such as a gene, for optimized or improved translation of the nucleic acid in a particular strain or species. Codon optimization may result in faster translation rates or translation accuracy. In an embodiment, the genes of the disclosure are codon optimized for expression in *Clostridium*, particularly *Clostridium autoethanogenum*, *Clostridium ljungdahlii*, or *Clostridium ragsdalei*. In a further embodiment, the genes of the disclosure are codon optimized for expression in *Clostridium autoethanogenum* LZ1561, which is deposited under DSMZ accession number DSM23693.

"Overexpressed" refers to an increase in expression of a nucleic acid or protein in the microorganism of the disclosure compared to the wild-type or parental microorganism from which the microorganism of the disclosure is derived. Overexpression may be achieved by any means known in the art, including modifying gene copy number, gene transcription rate, gene translation rate, or enzyme degradation rate.

The term "variants" includes nucleic acids and proteins whose sequence varies from the sequence of a reference nucleic acid and protein, such as a sequence of a reference nucleic acid and protein disclosed in the prior art or exemplified herein. The disclosure may be practiced using variant nucleic acids or proteins that perform substantially the same function as the reference nucleic acid or protein. For example, a variant protein may perform substantially the same function or catalyze substantially the same reaction as a reference protein. A variant gene may encode the same or substantially the same protein as a reference gene. A variant promoter may have substantially the same ability to promote the expression of one or more genes as a reference promoter.

Such nucleic acids or proteins may be referred to herein as "functionally equivalent variants." By way of example, functionally equivalent variants of a nucleic acid may include allelic variants, fragments of a gene, mutated genes, polymorphisms, and the like. Homologous genes from other microorganisms are also examples of functionally equivalent variants. These include homologous genes in species such as *Clostridium acetobutylicum, Clostridium beijerinckii*, or *Clostridium ljungdahlii*, the details of which are publicly available on websites such as Genbank or NCBI. Functionally equivalent variants also include nucleic acids whose sequence varies as a result of codon optimization for a particular microorganism. A functionally equivalent variant of a nucleic acid will preferably have at least approximately 70%, approximately 80%, approximately 85%, approximately 90%, approximately 95%, approximately 98%, or greater nucleic acid sequence identity (percent homology) with the referenced nucleic acid. A functionally equivalent variant of a protein will preferably have at least approximately 70%, approximately 80%, approximately 85%, approximately 90%, approximately 95%, approximately 98%, or greater amino acid identity (percent homology) with the referenced protein. The functional equivalence of a variant nucleic acid or protein may be evaluated using any method known in the art.

"Complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%. 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent and vary depending on a number of factors. In general, the longer the sequence, the higher the temperature at which the sequence specifically hybridizes to its target sequence. Non-limiting examples of stringent conditions are well known in the art (e.g., Tijssen, Laboratory techniques in biochemistry and molecular biology-hybridization with nucleic acid probes, Second Chapter "Overview of principles of hybridization and the strategy of nucleic acid probe assay," Elsevier, N.Y., 1993).

"Hybridization" refers to a reaction in which one or more polynucleotides react to form a complex that is stabilized via hydrogen bonding between the bases of the nucleotide residues. The hydrogen bonding may occur by Watson Crick base pairing, Hoogsteen binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

Nucleic acids may be delivered to a microorganism of the disclosure using any method known in the art. For example, nucleic acids may be delivered as naked nucleic acids or may be formulated with one or more agents, such as liposomes. The nucleic acids may be DNA, RNA, cDNA, or combinations thereof, as is appropriate. Restriction inhibitors may be used in certain embodiments. Additional vectors may include plasmids, viruses, bacteriophages, cosmids, and artificial chromosomes. In an embodiment, nucleic acids are delivered to the microorganism of the disclosure using a plasmid. By way of example, transformation (including transduction or transfection) may be achieved by electroporation, ultrasonication, polyethylene glycol-mediated transformation, chemical or natural competence, protoplast transformation, prophage induction, or conjugation. In certain embodiments having active restriction enzyme systems, it may be necessary to methylate a nucleic acid before introduction of the nucleic acid into a microorganism.

Furthermore, nucleic acids may be designed to comprise a regulatory element, such as a promoter, to increase or otherwise control expression of a particular nucleic acid. The promoter may be a constitutive promoter or an inducible promoter. Ideally, the promoter is a Wood-Ljungdahl pathway promoter, a ferredoxin promoter, a pyruvate:ferredoxin oxidoreductase promoter, an Rnf complex operon promoter, an ATP synthase operon promoter, or a phosphotransacetylase/acetate kinase operon promoter.

A "microorganism" is a microscopic organism, especially a bacterium, archaeon, virus, or fungus. The microorganism of the disclosure is typically a bacterium. As used herein, recitation of "microorganism" should be taken to encompass "bacterium."

A "parental microorganism" is a microorganism used to generate a microorganism of the disclosure. The parental microorganism may be a naturally-occurring microorganism (i.e., a wild-type microorganism) or a microorganism that has been previously modified (i.e., a mutant or recombinant microorganism). The microorganism of the disclosure may be modified to express or overexpress one or more enzymes that were not expressed or overexpressed in the parental microorganism. Similarly, the microorganism of the disclosure may be modified to contain one or more genes that were not contained by the parental microorganism. The microorganism of the disclosure may also be modified to not express or to express lower amounts of one or more enzymes that were expressed in the parental microorganism. In one embodiment, the parental microorganism is *Clostridium autoethanogenum*, *Clostridium ljungdahlii*, or *Clostridium ragsdalei*. In an embodiment, the parental microorganism is *Clostridium autoethanogenum* LZ1561, which was deposited with Deutsche Sammlung von Mikroorganismen and Zellkulturen GmbH (DSMZ) located at Inhoffenstraße 7B, D-38124 Braunschweig, Germany on Jun. 7, 2010, under the terms of the Budapest Treaty and accorded accession number DSM23693. This strain is described in International Patent Application No. PCT/NZ2011/000144, which published as WO 2012/015317.

The term "derived from" indicates that a nucleic acid, protein, or microorganism is modified or adapted from a different (e.g., a parental or wild-type) nucleic acid, protein, or microorganism, so as to produce a new nucleic acid, protein, or microorganism. Such modifications or adaptations typically include insertion, deletion, mutation, or substitution of nucleic acids or genes. Generally, the microorganism of the disclosure is derived from a parental microorganism. In one embodiment, the microorganism of the disclosure is derived from *Clostridium autoethanogenum*, *Clostridium ljungdahlii*, or *Clostridium ragsdalei*. In an embodiment, the microorganism of the disclosure is derived from *Clostridium autoethanogenum* LZ1561, which is deposited under DSMZ accession number DSM23693.

The microorganism of the disclosure may be further classified based on functional characteristics. For example, the microorganism of the disclosure may be or may be derived from a C1-fixing microorganism, an anaerobe, an acetogen, an ethanologen, a carboxydotroph, and/or a methanotroph. Table 1 provides a representative list of microorganisms and identifies their functional characteristics.

TABLE 1

| | Wood-Ljungdahl | C1-fixing | Anaerobe | Acetogen | Ethanologen | Autotroph | Carboxydotroph |
|---|---|---|---|---|---|---|---|
| *Acetobacterium woodii* | + | + | + | + | +/− [1] | + | − |
| *Alkalibaculum bacchii* | + | + | + | + | + | + | + |
| *Blautia producta* | + | + | + | + | − | + | + |
| *Butyribacterium methylotrophicum* | + | + | + | + | + | + | + |
| *Clostridium aceticum* | + | + | + | + | − | + | + |
| *Clostridium autoethanogenum* | + | + | + | + | + | + | + |
| *Clostridium carboxidivorans* | + | + | + | + | + | + | + |
| *Clostridium coskatii* | + | + | + | + | + | + | + |
| *Clostridium drakei* | + | + | + | + | − | + | + |
| *Clostridium formicoaceticum* | + | + | + | + | − | + | + |
| *Clostridium ljungdahlii* | + | + | + | + | + | + | + |
| *Clostridium magnum* | + | + | + | + | − | + | +/− [2] |
| *Clostridium ragsdalei* | + | + | + | + | + | + | + |
| *Clostridium scatologenes* | + | + | + | + | − | + | + |
| *Eubacterium limosum* | + | + | + | + | − | + | + |
| *Moorella thermautotrophica* | + | + | + | + | + | + | + |
| *Moorella thermoacetica* (formerly *Clostridium thermoaceticum*) | + | + | + | + | − [3] | + | + |
| *Oxobacter pfennigii* | + | + | + | + | − | + | + |
| *Sporomusa ovata* | + | + | + | + | − | + | +/− [4] |
| *Sporomusa silvacetica* | + | + | + | + | − | + | +/− [5] |

TABLE 1-continued

| | Wood-Ljungdahl | C1-fixing | Anaerobe | Acetogen | Ethanologen | Autotroph | Carboxydotroph |
|---|---|---|---|---|---|---|---|
| *Sporomusa sphaeroides* | + | + | + | + | − | + | +/− [6] |
| *Thermoanaerobacter kivui* | + | + | + | + | − | + | − |

[1] *Acetobacterium woodii* can produce ethanol from fructose, but not from gas.
[2] It has not been investigated whether *Clostridium magnum* can grow on CO.
[3] One strain of *Moorella thermoacetica*, *Moorella* sp. HUC22-1, has been reported to produce ethanol from gas.
[4] It has not been investigated whether *Sporomusa ovata* can grow on CO.
[5] It has not been investigated whether *Sporomusa silvacetica* can grow on CO.
[6] It has not been investigated whether *Sporomusa sphaeroides* can grow on CO.

"Wood-Ljungdahl" refers to the Wood-Ljungdahl pathway of carbon fixation as described, e.g., by Ragsdale, Biochim Biophys Acta, 1784: 1873-1898, 2008. "Wood-Ljungdahl microorganisms" refers, predictably, to microorganisms containing the Wood-Ljungdahl pathway. Generally, the microorganism of the disclosure contains a native Wood-Ljungdahl pathway. Herein, a Wood-Ljungdahl pathway may be a native, unmodified Wood-Ljungdahl pathway or it may be a Wood-Ljungdahl pathway with some degree of genetic modification (e.g., overexpression, heterologous expression, knockout, etc.) so long as it still functions to convert CO, $CO_2$, and/or $H_2$ to acetyl-CoA.

"C1" refers to a one-carbon molecule, for example, CO, $CO_2$, $CH_4$, or $CH_3OH$. "C1-oxygenate" refers to a one-carbon molecule that also comprises at least one oxygen atom, for example, CO, $CO_2$, or $CH_3OH$. "C1-carbon source" refers a one carbon-molecule that serves as a partial or sole carbon source for the microorganism of the disclosure. For example, a C1-carbon source may comprise one or more of CO, $CO_2$, $CH_4$, $CH_3OH$, or $CH_2O_2$. Preferably, the C1-carbon source comprises one or both of CO and $CO_2$. A "C1-fixing microorganism" is a microorganism that has the ability to produce one or more products from a C1 carbon source. Typically, the microorganism of the disclosure is a C1-fixing bacterium. In an embodiment, the microorganism of the disclosure is derived from a C1-fixing microorganism identified in Table 1.

An "anaerobe" is a microorganism that does not require oxygen for growth. An anaerobe may react negatively or even die if oxygen is present above a certain threshold. However, some anaerobes are capable of tolerating low levels of oxygen (e.g., 0.000001-5% oxygen). Typically, the microorganism of the disclosure is an anaerobe. In an embodiment, the microorganism of the disclosure is derived from an anaerobe identified in Table 1.

"Acetogens" are obligately anaerobic bacteria that use the Wood-Ljungdahl pathway as their main mechanism for energy conservation and for synthesis of acetyl-CoA and acetyl-CoA-derived products, such as acetate (Ragsdale, Biochim Biophys Acta, 1784: 1873-1898, 2008). In particular, acetogens use the Wood-Ljungdahl pathway as a (1) mechanism for the reductive synthesis of acetyl-CoA from $CO_2$, (2) terminal electron-accepting, energy conserving process, (3) mechanism for the fixation (assimilation) of $CO_2$ in the synthesis of cell carbon (Drake, Acetogenic Prokaryotes, In: The Prokaryotes, 3rd edition, p. 354, New York, N.Y., 2006). All naturally occurring acetogens are C1-fixing, anaerobic, autotrophic, and non-methanotrophic. Typically, the microorganism of the disclosure is an acetogen. In an embodiment, the microorganism of the disclosure is derived from an acetogen identified in Table 1.

An "ethanologen" is a microorganism that produces or is capable of producing ethanol. Typically, the microorganism of the disclosure is an ethanologen. In an embodiment, the microorganism of the disclosure is derived from an ethanologen identified in Table 1.

An "autotroph" is a microorganism capable of growing in the absence of organic carbon. Instead, autotrophs use inorganic carbon sources, such as CO and/or $CO_2$. Typically, the microorganism of the disclosure is an autotroph. In an embodiment, the microorganism of the disclosure is derived from an autotroph identified in Table 1.

A "carboxydotroph" is a microorganism capable of utilizing CO as a sole source of carbon and energy. Typically, the microorganism of the disclosure is a carboxydotroph. In an embodiment, the microorganism of the disclosure is derived from a carboxydotroph identified in Table 1.

A "methanotroph" is a microorganism capable of utilizing methane as a sole source of carbon and energy. In certain embodiments, the microorganism of the disclosure is a methanotroph or is derived from a methanotroph. In other embodiments, the microorganism of the disclosure is not a methanotroph or is not derived from a methanotroph.

More broadly, the microorganism of the disclosure may be derived from any genus or species identified in Table 1. For example, the microorganism may be a member of a genus selected from the group consisting of *Acetobacterium, Alkalibaculum, Blautia, Butyribacterium, Clostridium, Eubacterium, Moorella, Oxobacter, Sporomusa*, and *Thermoanaerobacter*. In particular, the microorganism may be derived from a parental bacterium selected from the group consisting of *Acetobacterium woodii, Alkalibaculum bacchii, Blautia producta, Butyribacterium methylotrophicum, Clostridium aceticum, Clostridium autoethanogenum, Clostridium carboxidivorans, Clostridium coskatii, Clostridium drakei, Clostridium formicoaceticum, Clostridium ljungdahlii, Clostridium magnum, Clostridium ragsdalei, Clostridium scatologenes, Eubacterium limosum, Moorella thermautotrophica, Moorella thermoacetica, Oxobacter pfennigii, Sporomusa ovata, Sporomusa silvacetica, Sporomusa sphaeroides*, and *Thermoanaerobacter kivui*.

In an embodiment, the microorganism of the disclosure is derived from the cluster of Clostridia comprising the species *Clostridium autoethanogenum, Clostridium ljungdahlii*, and *Clostridium ragsdalei*. These species were first reported and characterized by Abrini, Arch Microbiol, 161: 345-351, 1994 (*Clostridium autoethanogenum*), Tanner, Int J System Bacteriol, 43: 232-236, 1993 (*Clostridium ljungdahlii*), and Huhnke, WO 2008/028055 (*Clostridium ragsdalei*).

These three species have many similarities. In particular, these species are all C1 fixing, anaerobic, acetogenic, ethanologenic, and carboxydotrophic members of the genus *Clostridium*. These species have similar genotypes and phenotypes and modes of energy conservation and fermentative metabolism. Moreover, these species are clustered in clostridial rRNA homology group I with 16S rRNA DNA that is more than 99% identical, have a DNA G+C content of about 22-30 mol %, are gram-positive, have similar morphology and size (logarithmic growing cells between 0.5-0.7×3-5 μm), are mesophilic (grow optimally at 30-37° C.), have similar pH ranges of about 4-7.5 (with an optimal pH of about 5.5-6), lack cytochromes, and conserve energy via an Rnf complex. Also, reduction of carboxylic acids into their corresponding alcohols has been shown in these species (Perez, Biotechnol Bioeng, 110:1066-1077, 2012). Importantly, these species also all show strong autotrophic growth on CO-containing gases, produce ethanol and acetate (or acetic acid) as main fermentation products, and produce small amounts of 2,3-butanediol and lactic acid under certain conditions.

However, these three species also have a number of differences. These species were isolated from different sources: *Clostridium autoethanogenum* from rabbit gut, *Clostridium ljungdahlii* from chicken yard waste, and *Clostridium ragsdalei* from freshwater sediment. These species differ in utilization of various sugars (e.g., rhamnose, arabinose), acids (e.g., gluconate, citrate), amino acids (e.g., arginine, histidine), and other substrates (e.g., betaine, butanol). Moreover, these species differ in auxotrophy to certain vitamins (e.g., thiamine, biotin). These species have differences in nucleic and amino acid sequences of Wood-Ljungdahl pathway genes and proteins, although the general organization and number of these genes and proteins has been found to be the same in all species (Köpke, *Curr Opin Biotechnol*, 22: 320-325, 2011).

Thus, in summary, many of the characteristics of *Clostridium autoethanogenum, Clostridium ljungdahlii*, or *Clostridium ragsdalei* are not specific to that species, but are rather general characteristics for this cluster of C1 fixing, anaerobic, acetogenic, ethanologenic, and carboxydotrophic members of the genus *Clostridium*. However, since these species are, in fact, distinct, the genetic modification or manipulation of one of these species may not have an identical effect in another of these species. For instance, differences in growth, performance, or product production may be observed.

The microorganism of the disclosure may also be derived from an isolate or mutant of *Clostridium autoethanogenum, Clostridium ljungdahlii*, or *Clostridium ragsdalei*. Isolates and mutants of *Clostridium autoethanogenum* include JA1-1 (DSM10061) (Abrini, *Arch Microbiol*, 161: 345-351, 1994), LZ1560 (DSM19630) (WO 2009/064200), and LZ1561 (DSM23693) (WO 2012/015317). Isolates and mutants of *Clostridium ljungdahlii* include ATCC 49587 (Tanner, *Int J Syst Bacteriol*, 43: 232-236, 1993), PETCT (DSM13528, ATCC 55383), ERI-2 (ATCC 55380) (U.S. Pat. No. 5,593,886), C-01 (ATCC 55988) (U.S. Pat. No. 6,368,819), O-52 (ATCC 55989) (U.S. Pat. No. 6,368,819), and OTA-1 (Tirado-Acevedo, Production of bioethanol from synthesis gas using *Clostridium ljungdahlii*, PhD thesis, North Carolina State University, 2010). Isolates and mutants of *Clostridium ragsdalei* include PI 1 (ATCC BAA-622, ATCC PTA-7826) (WO 2008/028055).

"Substrate" refers to a carbon and/or energy source for the microorganism of the disclosure. Typically, the substrate is gaseous and comprises a C1-carbon source, for example, $CO$, $CO_2$, and/or $CH_4$. Preferably, the substrate comprises a C1-carbon source of $CO$ or $CO+CO_2$. The substrate may further comprise other non-carbon components, such as $H_2$, $N_2$, or electrons.

The substrate generally comprises at least some amount of CO, such as about 1, 2, 5, 10, 20, 30, 40, 50, 60, 70, 80, 90, or 100 mol % CO. The substrate may comprise a range of CO, such as about 20-80, 30-70, or 40-60 mol % CO. Preferably, the substrate comprises about 40-70 mol % CO (e.g., steel mill or blast furnace gas), about 20-30 mol % CO (e.g., basic oxygen furnace gas), or about 15-45 mol % CO (e.g., syngas). In some embodiments, the substrate may comprise a relatively low amount of CO, such as about 1-10 or 1-20 mol % CO. The microorganism of the disclosure typically converts at least a portion of the CO in the substrate to a product. In some embodiments, the substrate comprises no or substantially no (<1 mol %) CO.

The substrate may comprise some amount of $H_2$. For example, the substrate may comprise about 1, 2, 5, 10, 15, 20, or 30 mol % $H_2$. In some embodiments, the substrate may comprise a relatively high amount of $H_2$, such as about 60, 70, 80, or 90 mol % $H_2$. In further embodiments, the substrate comprises no or substantially no (<1 mol %) $H_2$.

The substrate may comprise some amount of $CO_2$. For example, the substrate may comprise about 1-80 or 1-30 mol % $CO_2$. In some embodiments, the substrate may comprise less than about 20, 15, 10, or 5 mol % $CO_2$. In another embodiment, the substrate comprises no or substantially no (<1 mol %) $CO_2$.

Although the substrate is typically gaseous, the substrate may also be provided in alternative forms. For example, the substrate may be dissolved in a liquid saturated with a CO-containing gas using a microbubble dispersion generator. By way of further example, the substrate may be adsorbed onto a solid support.

The substrate and/or C1-carbon source may be a waste gas obtained as a byproduct of an industrial process or from some other source, such as from automobile exhaust fumes or biomass gasification. In certain embodiments, the industrial process is selected from the group consisting of ferrous metal products manufacturing, such as a steel mill manufacturing, non-ferrous products manufacturing, petroleum refining, coal gasification, electric power production, carbon black production, ammonia production, methanol production, and coke manufacturing. In these embodiments, the substrate and/or C1-carbon source may be captured from the industrial process before it is emitted into the atmosphere, using any convenient method.

The substrate and/or C1-carbon source may be syngas, such as syngas obtained by gasification of coal or refinery residues, gasification of biomass or lignocellulosic material, or reforming of natural gas. In another embodiment, the syngas may be obtained from the gasification of municipal solid waste or industrial solid waste. The substrate and/or C1-carbon source may be derived from pyrolysis with or without subsequent partial oxidation of the pyrolysis oil.

The composition of the substrate may have a significant impact on the efficiency and/or cost of the reaction. For example, the presence of oxygen ($O_2$) may reduce the efficiency of an anaerobic fermentation process. Depending on the composition of the substrate, it may be desirable to treat, scrub, or filter the substrate to remove any undesired impurities, such as toxins, undesired components, or dust particles, and/or increase the concentration of desirable components.

In particular embodiments, the presence of hydrogen results in an improved overall efficiency of the fermentation process.

Syngas composition can be improved to provide a desired or optimum $H_2:CO:CO_2$ ratio. The syngas composition may be improved by adjusting the feedstock being fed to the gasification process. The desired $H_2:CO:CO_2$ ratio is dependent on the desired fermentation product of the fermentation process. For ethanol, the optimum $H_2:CO:CO_2$ ratio would be:

$$(x):(y):\left(\frac{x-2y}{3}\right),$$

where x>2y, in order to satisfy the stoichiometry for ethanol production $$(x)H_2 + (y)CO + \left(\frac{x-2y}{3}\right)CO_2 \rightarrow \left(\frac{x+y}{6}\right)C_2H_5OH + \left(\frac{x-y}{2}\right)H_2O.$$

Operating the fermentation process in the presence of hydrogen has the added benefit of reducing the amount of $CO_2$ produced by the fermentation process. For example, a gaseous substrate comprising minimal $H_2$ will typically produce ethanol and $CO_2$ by the following stoichiometry [$6CO+3H_2O \rightarrow C_2H_5OH+4CO_2$]. As the amount of hydrogen utilized by the C1-fixing bacterium increases, the amount of $CO_2$ produced decreases [e.g., $2CO+4H_2 \rightarrow C_2H_5OH+H_2O$].

When CO is the sole carbon and energy source for ethanol production, a portion of the carbon is lost to $CO_2$ as follows:

$6CO+3H_2O \rightarrow C_2H_5OH+4CO_2 (\Delta G°=-224.90$ kJ/mol ethanol)

As the amount of $H_2$ available in the substrate increases, the amount of $CO_2$ produced decreases. At a stoichiometric ratio of 2:1 ($H_2$:CO), $CO_2$ production is completely avoided.

$5CO+1H_2+2H_2O \rightarrow 1C_2H_5OH+3CO_2 (\Delta G°=-204.80$ kJ/mol ethanol)

$4CO+2H_2+1H_2O \rightarrow 1C_2H_5OH+2CO_2 (\Delta G°=-184.70$ kJ/mol ethanol)

$3CO+3H_2 \rightarrow 1C_2H_5OH+1CO_2 (\Delta G°=-164.60$ kJ/mol ethanol)

"Stream" refers to any substrate which is capable of being passed, for example, from one process to another, from one module to another, and/or from one process to a carbon capture means.

"Reactants" as used herein refer to a substance that takes part in and undergoes change during a chemical reaction. In particular embodiments, the reactants include but are not limited to CO and/or $H_2$.

"Microbe inhibitors" as used herein refer to one or more constituent that slows down or prevents a particular chemical reaction or another process including the microbe. In particular embodiments, the microbe inhibitors include, but are not limited to, oxygen (O2), hydrogen cyanide (HCN), acetylene ($C_2H_2$), and BTEX (benzene, toluene, ethylbenzene, xylene).

"Catalyst inhibitor", "adsorbent inhibitor", and the like, as used herein, refer to one or more substance that decreases the rate of, or prevents, a chemical reaction. In particular embodiments, the catalyst and/or adsorbent inhibitors may include but are not limited to, hydrogen sulfide ($H_2S$) and carbonyl sulfide (COS).

"Removal process", "removal module", "clean-up module", and the like includes technologies that are capable of either converting and/or removing microbe inhibitors and/or catalyst inhibitors from the gas stream. In particular embodiments, catalyst inhibitors must be removed by an upstream removal module in order to prevent inhibition of one or more catalyst in a downstream removal module.

The term "constituents", "contaminants", and the like, as used herein, refers to the microbe inhibitors, and/or catalyst inhibitors that may be found in the gas stream. In particular embodiments, the constituents include, but are not limited to, sulphur compounds, aromatic compounds, alkynes, alkenes, alkanes, olefins, nitrogen compounds, phosphorous-containing compounds, particulate matter, solids, oxygen, halogenated compounds, silicon-containing compounds, carbonyls, metals, alcohols, esters, ketones, peroxides, aldehydes, ethers, and tars.

The term "treated gas", "treated stream" and the like refers to the gas stream that has been passed through at least one removal module and has had one or more constituent removed and/or converted.

The term "desired composition" is used to refer to the desired level and types of components in a substance, such as, for example, of a gas stream, including but not limited to syngas. More particularly, a gas is considered to have a "desired composition" if it contains a particular component (e.g. CO, $H_2$, and/or $CO_2$) and/or contains a particular component at a particular proportion and/or does not contain a particular component (e.g. a contaminant harmful to the microorganisms) and/or does not contain a particular component at a particular proportion. More than one component may be considered when determining whether a gas stream has a desired composition.

The composition of the substrate may have a significant impact on the efficiency and/or cost of the reaction. For example, the presence of oxygen ($O_2$) may reduce the efficiency of an anaerobic fermentation process. Depending on the composition of the substrate, it may be desirable to treat, scrub, or filter the substrate to remove any undesired impurities, such as toxins, undesired components, or dust particles, and/or increase the concentration of desirable components.

The term "carbon capture" as used herein refers to the sequestration of carbon compounds including $CO_2$ and/or CO from a stream comprising $CO_2$ and/or CO and either: converting the $CO_2$ and/or CO into products; or converting the $CO_2$ and/or CO into substances suitable for long-term storage; or trapping the $CO_2$ and/or CO in substances suitable for long-term storage;
or a combination of these processes.

In certain embodiments, the fermentation is performed in the absence of carbohydrate substrates, such as sugar, starch, lignin, cellulose, or hemicellulose.

The microorganism of the disclosure may be cultured with the gaseous substrate to produce one or more products. For instance, the microorganism of the disclosure may produce or may be engineered to produce ethanol (WO 2007/117157), acetate (WO 2007/117157), 1-butanol (WO 2008/115080, WO 2012/053905, and WO 2017/066498), butyrate (WO 2008/115080), 2,3-butanediol (WO 2009/151342 and WO 2016/094334), lactate (WO 2011/112103), butene (WO 2012/024522), butadiene (WO 2012/024522), methyl ethyl ketone (2-butanone) (WO 2012/024522 and WO 2013/185123), ethylene (WO 2012/026833), acetone (WO 2012/115527), isopropanol (WO 2012/115527), lipids (WO 2013/036147), 3-hydroxypropionate (3-HP) (WO 2013/180581), terpenes, including isoprene (WO 2013/180584), fatty acids (WO 2013/191567), 2-butanol (WO 2013/185123), 1,2-propanediol (WO 2014/036152), 1-propanol (WO 2017/066498), 1-hexanol (WO 2017/066498), 1-octanol (WO 2017/066498), chorismate-derived products (WO 2016/191625), 3-hydroxybutyrate (WO 2017/066498), 1,3-butanediol (WO 2017/066498), 2-hydroxyisobutyrate or 2-hydroxyisobutyric acid (WO 2017/066498), isobutylene (WO 2017/066498), adipic acid (WO 2017/066498), 1,3-hexanediol (WO 2017/066498), 3-methyl-2-butanol (WO 2017/066498), 2-buten-1-ol (WO 2017/066498), isovalerate (WO 2017/066498), isoamyl alcohol (WO 2017/066498), and/or monoethylene glycol (WO 2019/126400) in addition to 2-phenylethanol. In certain embodiments, microbial biomass itself may be considered a product. These products may be further converted to produce at least one component of diesel, jet fuel, and/or gasoline. In certain embodiments, 2-phenylethanol may be used as an ingredient in fragrances, essential oils, flavors, and soaps. Additionally, the microbial biomass may be further processed to produce a single cell protein (SCP).

A "single cell protein" (SCP) refers to a microbial biomass that may be used in protein-rich human and/or animal feeds, often replacing conventional sources of protein supplementation such as soymeal or fishmeal. To produce a single cell protein or other product, the process may comprise additional separation, processing, or treatments steps. For example, the method may comprise sterilizing the microbial biomass, centrifuging the microbial biomass, and/or drying the microbial biomass. In certain embodiments, the microbial biomass is dried using spray drying or paddle drying. The method may also comprise reducing the nucleic acid content of the microbial biomass using any method known in the art, since intake of a diet high in nucleic acid content may result in the accumulation of nucleic acid degradation products and/or gastrointestinal distress. The single cell protein may be suitable for feeding to animals, such as livestock or pets. In particular, the animal feed may be suitable for feeding to one or more beef cattle, dairy cattle, pigs, sheep, goats, horses, mules, donkeys, deer, buffalo/bison, llamas, alpacas, reindeer, camels, bantengs, gayals, yaks, chickens, turkeys, ducks, geese, quail, guinea fowl, squabs/pigeons, fish, shrimp, crustaceans, cats, dogs, and rodents. The composition of the animal feed may be tailored to the nutritional requirements of different animals. Furthermore, the process may comprise blending or combining the microbial biomass with one or more excipients.

An "excipient" may refer to any substance that may be added to the microbial biomass to enhance or alter the form, properties, or nutritional content of the animal feed. For example, the excipient may comprise one or more of a carbohydrate, fiber, fat, protein, vitamin, mineral, water, flavor, sweetener, antioxidant, enzyme, preservative, probiotic, or antibiotic. In some embodiments, the excipient may be hay, straw, silage, grains, oils or fats, or other plant material. The excipient may be any feed ingredient identified in Chiba, Section 18: Diet Formulation and Common Feed Ingredients, Animal Nutrition Handbook, 3rd revision, pages 575-633, 2014.

A "native product" is a product produced by a genetically unmodified microorganism. For example, ethanol, acetate, and 2,3-butanediol are native products of *Clostridium autoethanogenum, Clostridium ljungdahlii,* and *Clostridium ragsdalei*. A "non-native product" is a product that is produced by a genetically modified microorganism but is not produced by a genetically unmodified microorganism from which the genetically modified microorganism is derived.

"Selectivity" refers to the ratio of the production of a target product to the production of all fermentation products produced by a microorganism. The microorganism of the disclosure may be engineered to produce products at a certain selectivity or at a minimum selectivity. In one embodiment, a target product account for at least about 5%, 10%, 15%, 20%, 30%, 50%, or 75% of all fermentation products produced by the microorganism of the disclosure. In one embodiment, the target product accounts for at least 10% of all fermentation products produced by the microorganism of the disclosure, such that the microorganism of the disclosure has a selectivity for the target product of at least 10%. In another embodiment, the target product accounts for at least 30% of all fermentation products produced by the microorganism of the disclosure, such that the microorganism of the disclosure has a selectivity for the target product of at least 30%.

"Increasing the efficiency," "increased efficiency," and the like include, but are not limited to, increasing growth rate, product production rate or volume, product volume per volume of substrate consumed, or product selectivity. Efficiency may be measured relative to the performance of parental microorganism from which the microorganism of the disclosure is derived.

Typically, the culture is performed in a bioreactor. The term "bioreactor" includes a culture/fermentation device consisting of one or more vessels, towers, or piping arrangements, such as a continuous stirred tank reactor (CSTR), immobilized cell reactor (ICR), trickle bed reactor (TBR), bubble column, gas lift fermenter, static mixer, or other vessel or other device suitable for gas-liquid contact. In some embodiments, the bioreactor may comprise a first growth reactor and a second culture/fermentation reactor. The substrate may be provided to one or both of these reactors. As used herein, the terms "culture" and "fermentation" are used interchangeably. These terms encompass both the growth phase and product biosynthesis phase of the culture/fermentation process.

The culture is generally maintained in an aqueous culture medium that contains nutrients, vitamins, and/or minerals sufficient to permit growth of the microorganism. Preferably the aqueous culture medium is an anaerobic microbial growth medium, such as a minimal anaerobic microbial growth medium. Suitable media are well known in the art.

The culture/fermentation should desirably be carried out under appropriate conditions for production of the target product. Typically, the culture/fermentation is performed under anaerobic conditions. Reaction conditions to consider include pressure (or partial pressure), temperature, gas flow rate, liquid flow rate, media pH, media redox potential, agitation rate (if using a continuous stirred tank reactor), inoculum level, maximum gas substrate concentrations to ensure that gas in the liquid phase does not become limiting, and maximum product concentrations to avoid product inhibition. In particular, the rate of introduction of the substrate may be controlled to ensure that the concentration of gas in the liquid phase does not become limiting, since products may be consumed by the culture under gas-limited conditions.

Operating a bioreactor at elevated pressures allows for an increased rate of gas mass transfer from the gas phase to the liquid phase. Accordingly, it is generally preferable to perform the culture/fermentation at pressures higher than atmospheric pressure. Also, since a given gas conversion rate is, in part, a function of the substrate retention time and retention time dictates the required volume of a bioreactor, the use of pressurized systems can greatly reduce the volume of the bioreactor required and, consequently, the capital cost of the culture/fermentation equipment. This, in turn, means that the retention time, defined as the liquid volume in the bioreactor divided by the input gas flow rate, can be reduced when bioreactors are maintained at elevated pressure rather than atmospheric pressure. The optimum reaction conditions will depend partly on the particular microorganism used. However, in general, it is preferable to operate the fermentation at a pressure higher than atmospheric pressure. Also, since a given gas conversion rate is in part a function of substrate retention time and achieving a desired retention time in turn dictates the required volume of a bioreactor, the use of pressurized systems can greatly reduce the volume of the bioreactor required, and consequently the capital cost of the fermentation equipment.

In certain embodiments, the fermentation is performed in the absence of light or in the presence of an amount of light insufficient to meet the energetic requirements of photosynthetic microorganisms. In certain embodiments, the microorganism of the disclosure is a non-photosynthetic microorganism.

As used herein, the terms "fermentation broth" or "broth" refer to the mixture of components in a bioreactor, which includes cells and nutrient media. As used herein, a "separator" is a module that is adapted to receive fermentation broth from a bioreactor and pass the broth through a filter to yield a "retentate" and a "permeate." The filter may be a membrane, e.g. a cross-flow membrane or a hollow fibre membrane. The term "permeate" is used to refer to substantially soluble components of the broth that pass through the separator. The permeate will typically contain soluble fermentation products, byproducts, and nutrients. The retentate will typically contain cells. As used herein, the term "broth bleed" is used to refer to a portion of the fermentation broth that is removed from a bioreactor and not passed to a separator.

Target products may be separated or purified from a fermentation broth using any method or combination of methods known in the art, including, for example, fractional distillation, evaporation, pervaporation, gas stripping, phase separation, and extractive fermentation, including for example, liquid-liquid extraction. In certain embodiments, target products are recovered from the fermentation broth by continuously removing a portion of the broth from the bioreactor, separating microbial cells from the broth (conveniently by filtration), and recovering one or more target products from the broth. Alcohols and/or acetone may be recovered, for example, by distillation. Acids may be recovered, for example, by adsorption on activated charcoal. Separated microbial cells are preferably recycled back to the bioreactor. The cell-free permeate remaining after target products have been removed is also preferably returned to the bioreactor. Additional nutrients may be added to the cell-free permeate to replenish the medium before it is returned to the bioreactor.

As referred to herein, a "shuttle microorganism" is a microorganism in which a methyltransferase enzyme is expressed and is distinct from the destination microorganism.

As referred to herein, a "destination microorganism" is a microorganism in which the genes included on an expression construct/vector are expressed and is distinct from the shuttle microorganism. This is also called a host microorganism.

The term "main fermentation product" is intended to mean the one fermentation product which is produced in the highest concentration and/or yield. There may be one or more fermentation products. The most prevalent may or may not be the most commercially valuable.

The phrase "substrate comprising carbon monoxide" and like terms should be understood to include any substrate in which carbon monoxide is available to one or more strains of bacteria for growth and/or fermentation, for example.

The phrase "gaseous substrate comprising carbon monoxide" and like phrases and terms includes any gas which contains a level of carbon monoxide. In certain embodiments the substrate contains at least about 20% to about 100% CO by volume, from 20% to 70% CO by volume, from 30% to 60% CO by volume, and from 40% to 55% CO by volume. In particular embodiments, the substrate comprises about 25%, or about 30%, or about 35%, or about 40%, or about 45%, or about 50% CO, or about 55% CO, or about 60% CO by volume.

While it is not necessary for a substrate comprising CO to contain any hydrogen, the presence of $H_2$ should not be detrimental to product formation in accordance with methods of the disclosure. In particular embodiments, the presence of hydrogen results in an improved overall efficiency of alcohol production. For example, in particular embodiments, the substrate may comprise an approx. 2:1, or 1:1, or 1:2 ratio of $H_2$:CO. In one embodiment the substrate comprises about 30% or less $H_2$ by volume, 20% or less $H_2$ by volume, about 15% or less $H_2$ by volume or about 10% or less $H_2$ by volume. In other embodiments, the substrate stream comprises low concentrations of $H_2$, for example, less than 5%, or less than 4%, or less than 3%, or less than 2%, or less than 1%, or is substantially hydrogen free. The substrate may also contain some $CO_2$ for example, such as about 1% to about 80% $CO_2$ by volume, or 1% to about 30% $CO_2$ by volume. In one embodiment the substrate comprises less than or equal to about 20% $CO_2$ by volume. In particular embodiments the substrate comprises less than or equal to about 15% $CO_2$ by volume, less than or equal to about 10% $CO_2$ by volume, less than or equal to about 5% $CO_2$ by volume or substantially no $CO_2$.

The phrase "substrate comprising carbon dioxide" and like terms should be understood to include any substrate in which carbon dioxide is available to one or more strains of bacteria for growth and/or fermentation, for example. Substrates comprising carbon dioxide may further comprise hydrogen and/or carbon monoxide.

The phrase "gaseous substrate comprising carbon dioxide" and like phrases and terms includes any gas which contains a level of carbon dioxide. In certain embodiments the substrate contains at least about 10% to about 60% $CO_2$ by volume, from 20% to 50% $CO_2$ by volume, from 30% to 60% $CO_2$ by volume, and from 40% to 55% $CO_2$ by volume. In particular embodiments, the substrate comprises about 20%, or about 25%, or about 30%, or about 35%, or about 40%, or about 45%, or about 50% CO, or about 55% CO, or about 60% $CO_2$ by volume.

Preferably, a substrate comprising $CO_2$ will also contain a level of CO or $H_2$. In particular embodiments, the substrate comprises a $CO_2$:$H_2$ ratio of at least about 1:1, or at least about 1:2, or at least about 1:3, or at least about 1:4, or at least about 1:5.

In the description which follows, embodiments of the disclosure are described in terms of delivering and fermenting a "gaseous substrate containing CO and/or $CO_2$." However, it should be appreciated that the gaseous substrate may be provided in alternative forms. For example, the gaseous substrate containing CO and/or $CO_2$ may be provided dissolved in a liquid. Essentially, a liquid is saturated with a carbon monoxide containing gas and then that liquid is added to the bioreactor. This may be achieved using standard methodology. By way of example, a microbubble dispersion generator (Hensirisak et. al. Scale-up of microbubble dispersion generator for aerobic fermentation; Applied Biochemistry and Biotechnology Volume 101, Number 3/October 2002) could be used. By way of further example, the gaseous substrate containing CO may be adsorbed onto a solid support. Such alternative methods are encompassed by use of the term "substrate containing CO and/or $CO_2$," and the like.

In particular embodiments of the disclosure, the CO-containing gaseous substrate (or a gaseous substrate comprising $CO_2$, or CO and $CO_2$, or $CO_2$ and $H_2$ and CO) is an industrial off or waste gas. "Industrial waste or off gases" should be taken broadly to include any gases comprising CO and/or $CO_2$ produced by an industrial process and include gases produced as a result of ferrous metal products manufacturing, non-ferrous products manufacturing, petroleum refining processes, gasification of coal, gasification of biomass, electric power production, carbon black production, and coke manufacturing. Further examples may be provided elsewhere herein.

Unless the context requires otherwise, the phrases "fermenting", "fermentation process" or "fermentation reaction" and the like, as used herein, are intended to encompass both the growth phase and product biosynthesis phase of the process. As will be described further herein, in some embodiments the bioreactor may comprise a first growth reactor and a second fermentation reactor. As such, the addition of metals or compositions to a fermentation reaction should be understood to include addition to either or both of these reactors.

The term "bioreactor" includes a fermentation device consisting of one or more vessels and/or towers or piping arrangement, which includes the Continuous Stirred Tank Reactor (CSTR), Immobilized Cell Reactor (ICR), Trickle Bed Reactor (TBR), Bubble Column, Gas Lift Fermenter, Static Mixer, or other vessel or other device suitable for gas-liquid contact. In some embodiments the bioreactor may comprise a first growth reactor and a second fermentation reactor. As such, when referring to the addition of substrate to the bioreactor or fermentation reaction it should be understood to include addition to either or both of these reactors where appropriate.

It should be appreciated that the disclosure may be practiced using nucleic acids whose sequence varies from the sequences specifically exemplified herein provided they perform substantially the same function. For nucleic acid sequences that encode a protein or peptide this means that the encoded protein or peptide has substantially the same function. For nucleic acid sequences that represent promoter sequences, the variant sequence will have the ability to promote expression of one or more genes. Such nucleic acids may be referred to herein as "functionally equivalent variants." By way of example, functionally equivalent variants of a nucleic acid include allelic variants, fragments of a gene, genes which include mutations (deletion, insertion, nucleotide substitutions and the like) and/or polymorphisms and the like. Homologous genes from other microorganisms may also be considered as examples of functionally equivalent variants of the sequences specifically exemplified herein.

These include homologous genes in species such as *Clostridium ljungdahlii, Chloroflexus aurantiacus, Metallosphaera* or *Sulfolobus* spp, details of which are publicly available on web sites such as Genbank or NCBI. The phrase "functionally equivalent variants" should also be taken to include nucleic acids whose sequence varies as a result of codon optimisation for a particular organism. "Functionally equivalent variants" of a nucleic acid herein will preferably have at least approximately 70%, preferably approximately 80%, more preferably approximately 85%, preferably approximately 90%, preferably approximately 95% or greater nucleic acid sequence identity with the nucleic acid identified.

It should also be appreciated that the disclosure may be practiced using polypeptides whose sequence varies from the amino acid sequences specifically exemplified herein. These variants may be referred to herein as "functionally equivalent variants." A functionally equivalent variant of a protein or a peptide includes those proteins or peptides that share at least 40%, preferably 50%, preferably 60%, preferably 70%, preferably 75%, preferably 80%, preferably 85%, preferably 90%, preferably 95% or greater amino acid identity with the protein or peptide identified and has substantially the same function as the peptide or protein of interest. Such variants include within their scope fragments of a protein or peptide wherein the fragment comprises a truncated form of the polypeptide wherein deletions may be from 1 to 5, to 10, to 15, to 20, to 25 amino acids, and may extend from residue 1 through 25 at either terminus of the polypeptide, and wherein deletions may be of any length within the region; or may be at an internal location. Functionally equivalent variants of the specific polypeptides herein should also be taken to include polypeptides expressed by homologous genes in other species of bacteria, for example as exemplified in the previous paragraph.

The microorganisms of the disclosure may be prepared from a parental microorganism and one or more exogenous nucleic acids using any number of techniques known in the art for producing recombinant microorganisms. By way of example only, transformation (including transduction or transfection) may be achieved by electroporation, ultrasonication, polyethylene glycol-mediated transformation, chemical or natural competence, or conjugation. Suitable transformation techniques are described for example in, Sambrook J, Fritsch E F, Maniatis T: Molecular Cloning: A laboratory Manual, Cold Spring Harbour Laboratory Press, Cold Spring Harbour, 1989.

In certain embodiments, due to the restriction systems which are active in the microorganism to be transformed, it is necessary to methylate the nucleic acid to be introduced into the microorganism. This can be done using a variety of techniques, including those described below, and further exemplified in the Examples section herein after.

By way of example, in one embodiment, a recombinant microorganism of the disclosure is produced by a method comprises the following steps: introduction into a shuttle microorganism of (i) of an expression construct/vector as described herein and (ii) a methylation construct/vector comprising a methyltransferase gene; expression of the methyltransferase gene; isolation of one or more constructs/vectors from the shuttle microorganism; and, introduction of the one or more construct/vector into a destination microorganism.

In one embodiment, the methyltransferase gene of step B is expressed constitutively. In another embodiment, expression of the methyltransferase gene of step B is induced.

The shuttle microorganism is a microorganism, preferably a restriction negative microorganism that facilitates the methylation of the nucleic acid sequences that make up the expression construct/vector. In a particular embodiment, the shuttle microorganism is a restriction negative *E. coli, Bacillus subtilis,* or *Lactococcus lactis*.

The methylation construct/vector comprises a nucleic acid sequence encoding a methyltransferase.

Once the expression construct/vector and the methylation construct/vector are introduced into the shuttle microorganism, the methyltransferase gene present on the methylation construct/vector is induced. Induction may be by any suitable promoter system although in one particular embodiment of the disclosure, the methylation construct/vector comprises an inducible lac promoter and is induced by addition of lactose or an analogue thereof, more preferably isopropyl-β-D-thio-galactoside (IPTG). Other suitable promoters include the ara, tet, or T7 system. In a further embodiment of the disclosure, the methylation construct/vector promoter is a constitutive promoter.

In a particular embodiment, the methylation construct/vector has an origin of replication specific to the identity of the shuttle microorganism so that any genes present on the methylation construct/vector are expressed in the shuttle microorganism. Preferably, the expression construct/vector has an origin of replication specific to the identity of the destination microorganism so that any genes present on the expression construct/vector are expressed in the destination microorganism.

Expression of the methyltransferase enzyme results in methylation of the genes present on the expression construct/vector. The expression construct/vector may then be isolated from the shuttle microorganism according to any one of a number of known methods. By way of example only, the methodology described in the Examples section described hereinafter may be used to isolate the expression construct/vector.

In one particular embodiment, both construct/vector are concurrently isolated.

The expression construct/vector may be introduced into the destination microorganism using any number of known methods. However, by way of example, the methodology described in the Examples section hereinafter may be used. Since the expression construct/vector is methylated, the nucleic acid sequences present on the expression construct/vector are able to be incorporated into the destination microorganism and successfully expressed.

It is envisaged that a methyltransferase gene may be introduced into a shuttle microorganism and over-expressed. Thus, in one embodiment, the resulting methyltransferase enzyme may be collected using known methods and used in vitro to methylate an expression plasmid. The expression construct/vector may then be introduced into the destination microorganism for expression. In another embodiment, the methyltransferase gene is introduced into the genome of the shuttle microorganism followed by introduction of the expression construct/vector into the shuttle microorganism, isolation of one or more constructs/vectors from the shuttle microorganism and then introduction of the expression construct/vector into the destination microorganism.

It is envisaged that the expression construct/vector and the methylation construct/vector as defined above may be combined to provide a composition of matter. Such a composition has particular utility in circumventing restriction barrier mechanisms to produce the recombinant microorganisms of the disclosure.

In one particular embodiment, the expression construct/vector and/or the methylation construct/vector are plasmids.

Persons of ordinary skill in the art will appreciate a number of suitable methyltransferases of use in producing the microorganisms of the disclosure. However, by way of example the *Bacillus subtilis* phage ΦT1 methyltransferase and the methyltransferase described in the Examples herein after may be used. Nucleic acids encoding suitable methyltransferases will be readily appreciated having regard to the sequence of the desired methyltransferase and the genetic code.

Any number of constructs/vectors adapted to allow expression of a methyltransferase gene may be used to generate the methylation construct/vector.

The disclosure provides a method for the production of 3-HP and optionally one or more other products by microbial fermentation comprising fermenting a substrate comprising CO and/or $CO_2$ using a recombinant microorganism of the disclosure. Preferably, 3-HP is the main fermentation product. The methods of the disclosure may be used to reduce the total atmospheric carbon emissions from an industrial process.

Preferably, the fermentation comprises the steps of anaerobically fermenting a substrate in a bioreactor to produce at least 3-HP using a recombinant microorganism of the disclosure.

In one embodiment the method comprises the steps of:
(a) providing a substrate comprising CO and/or $CO_2$ to a bioreactor containing a culture of one or more microorganism of the disclosure; and
(b) anaerobically fermenting the culture in the bioreactor to produce at least 3-HP.

In one embodiment the method comprises the steps of:
(a) capturing CO- and/or $CO_2$-containing gas produced as a result of the industrial process, before the gas is released into the atmosphere;
(b) the anaerobic fermentation of the CO- and/or $CO_2$-containing gas to produce the at least 3-HP by a culture containing one or more microorganism of the disclosure.

In one embodiment, the substrate comprises CO. In one embodiment, the substrate comprises $CO_2$ and CO. In another embodiment, the substrate comprises $CO_2$ and $H_2$. In another embodiment, the substrate comprises $CO_2$ and CO and $H_2$.

In one particular embodiment of the disclosure, the gaseous substrate fermented by the microorganism is a gaseous substrate containing CO. The gaseous substrate may be a CO-containing waste gas obtained as a by-product of an industrial process, or from some other source such as from automobile exhaust fumes. In certain embodiments, the industrial process is selected from the group consisting of ferrous metal products manufacturing, such as a steel mill, non-ferrous products manufacturing, petroleum refining processes, gasification of coal, electric power production, carbon black production, ammonia production, methanol production and coke manufacturing. In these embodiments, the CO-containing gas may be captured from the industrial process before it is emitted into the atmosphere, using any convenient method. The CO may be a component of syngas (gas comprising carbon monoxide and hydrogen). The CO produced from industrial processes is normally flared off to produce $CO_2$ and therefore the disclosure has particular utility in reducing $CO_2$ greenhouse gas emissions and producing butanol for use as a biofuel. Depending on the composition of the gaseous CO-containing substrate, it may also be desirable to treat it to remove any undesired impurities, such as dust particles before introducing it to the fermentation. For example, the gaseous substrate may be filtered or scrubbed using known methods.

In particular embodiments of the disclosure, the gaseous substrate fermented by the microorganisms a gaseous substrate comprising $CO_2$ and $H_2$. The $CO_2/H_2$ containing substrate may be a waste gas obtained as a by-product of an industrial process. In certain embodiments the industrial process is selected from the group consisting of hydrogen production. In certain embodiments the gaseous substrate comprising $CO_2$ and $H_2$ may be a blended gas stream, wherein at least a portion of the gas stream is derived from one or more industrial process is blended with at least a portion of $CO_2$ or $H_2$ to optimise the $CO_2$:$H_2$ ratio of the gaseous substrate. This may be particularly beneficial for industrial gas streams rich in either $CO_2$ or $H_2$. Examples of industrial process which produce by-product gas streams which can be used as a source for a $CO_2$ and $H_2$ substrate, or a $CO_2$ and $H_2$ blended substrate include coke manufacturing, refinery processes, ammonia production processes, methanol production processes, acetic acid production, natural gas refineries and power plants.

It will be appreciated that for growth of the bacteria and conversion of gas to products comprising 3-HP to occur, a suitable liquid nutrient medium in addition to the CO- and/or $CO_2$-containing substrate gas will need to be fed to the bioreactor. The substrate and media may be fed to the bioreactor in a continuous, batch or batch fed fashion. A nutrient medium will contain vitamins and minerals sufficient to permit growth of the micro-organism used. Anaerobic media suitable for fermentation to produce one or more products using CO and/or $CO_2$ are known in the art. For example, suitable media are described Biebel (2001). In one embodiment of the disclosure the media is as described in the Examples section herein after.

The fermentation should desirably be carried out under appropriate conditions for the fermentation supporting the conversion of the gas to products comprising 3-HP to occur. Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO and/or $CO_2$ in the liquid phase does not become limiting, and maximum product concentrations to avoid product inhibition.

In addition, it is often desirable to increase the CO and/or $CO_2$ concentration of a substrate stream (or CO and/or $CO_2$ partial pressure in a gaseous substrate) and thus increase the efficiency of fermentation reactions where CO and/or $CO_2$ is a substrate. Operating at increased pressures allows a significant increase in the rate of CO and/or $CO_2$ transfer from the gas phase to the liquid phase where it can be taken up by the micro-organism as a carbon source to make products comprising 3-HP. This in turn means that the retention time (defined as the liquid volume in the bioreactor divided by the input gas flow rate) can be reduced when bioreactors are maintained at elevated pressure rather than atmospheric pressure. The optimum reaction conditions will depend partly on the particular micro-organism of the disclosure used. However, in general, it is preferred that the fermentation be performed at pressure higher than ambient pressure. Also, since a given CO- and/or $CO_2$-to-at least 3-HP conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment. According to examples given in U.S. Pat. No. 5,593,886, reactor volume can be reduced in linear proportion to increases in reactor operating pressure, i.e. bioreactors operated at 10 atmospheres of pressure need only be one tenth the volume of those operated at 1 atmosphere of pressure.

By way of example, the benefits of conducting a gas-to-ethanol fermentation at elevated pressures has been described. For example, WO 02/08438 describes gas-to-ethanol fermentations performed under pressures of 30 psig and 75 psig, giving ethanol productivities of 150 g/l/day and 369 g/l/day respectively. However, example fermentations performed using similar media and input gas compositions at atmospheric pressure were found to produce between 10 and 20 times less ethanol per litre per day.

It is also desirable that the rate of introduction of the CO and/or $CO_2$-containing gaseous substrate is such as to ensure that the concentration of CO and/or $CO_2$ in the liquid phase does not become limiting. This is because a consequence of CO- and/or $CO_2$-limited conditions may be that one or more product is consumed by the culture.

The composition of gas streams used to feed a fermentation reaction can have a significant impact on the efficiency and/or costs of that reaction. For example, $O_2$ may reduce the efficiency of an anaerobic fermentation process. Processing of unwanted or unnecessary gases in stages of a fermentation process before or after fermentation can increase the burden on such stages (to products comprising where the gas stream is compressed before entering a bioreactor, unnecessary energy may be used to compress gases that are not needed in the fermentation). Accordingly, it may be desirable to treat substrate streams, particularly substrate streams derived from industrial sources, to remove unwanted components and increase the concentration of desirable components.

In certain embodiments a culture of a bacterium of the disclosure is maintained in an aqueous culture medium. Preferably the aqueous culture medium is a minimal anaerobic microbial growth medium. Suitable media are known in the art and described for example in U.S. Pat. Nos. 5,173,429 and 5,593,886 and WO 02/08438, and as described in the Examples section herein after.

3-HP, or a mixed stream containing 3-HP and/or one or more other products, may be recovered from the fermentation broth by methods known in the art, such as fractional distillation or evaporation, pervaporation, gas stripping and extractive fermentation, including for example, liquid-liquid extraction.

In certain embodiments of the disclosure, 3-HP and one or more products are recovered from the fermentation broth by continuously removing a portion of the broth from the bioreactor, separating microbial cells from the broth (conveniently by filtration), and recovering one or more products from the broth. Alcohols may conveniently be recovered for example by distillation. Acetone may be recovered for example by distillation. Any acids produced may be recovered for example by adsorption on activated charcoal. The separated microbial cells are preferably returned to the fermentation bioreactor. The cell free permeate remaining after any alcohol(s) and acid(s) have been removed is also preferably returned to the fermentation bioreactor. Additional nutrients (such as B vitamins) may be added to the cell free permeate to replenish the nutrient medium before it is returned to the bioreactor.

Also, if the pH of the broth was adjusted as described above to enhance adsorption of acetic acid to the activated charcoal, the pH should be re-adjusted to a similar pH to that of the broth in the fermentation bioreactor, before being returned to the bioreactor.

3-HP may be recovered following fermentation using any appropriate methodology including but not limited to pervaporation, reverse osmosis, and liquid extraction techniques.

One embodiment is directed to a recombinant C1-fixing bacteria capable of producing 3-hydroxypropionate (3-HP) from a carbon source comprising a nucleic acid encoding a group of exogenous enzymes comprising β-alanine pyruvate aminotransferase and malonic semialdehyde reductase.

The bacteria according to an embodiment, further comprising a nucleic acid encoding a group of exogenous enzymes comprising pyruvate carboxylase, aspartate aminotransferase, and aspartate decarboxylase, wherein the nucleic acid is operably linked to a promoter.

The bacteria according to an embodiment, further comprising a nucleic acid encoding a group of exogenous enzymes comprising alanine dehydrogenase and 2,3-alanine aminomutase, wherein the nucleic acid is operably linked to a promoter.

The bacteria according to an embodiment, which are selected from the group consisting of *Clostridium autoethanogenum, Clostridium ljungdahlii, Clostridium ragsdalei, Clostridium carboxidivorans, Clostridium drakei, Clostridium scatologenes, Clostridium aceticum, Clostridium formicoaceticum, Clostridium magnum, Butyribacterium methylotrophicum, Acetobacterium woodii, Alkalibaculum bacchii, Blautia producta, Eubacterium limosum, Moorella thermoacetica, Moorella thermautotrophica, Sporomusa ovata, Sporomusa silvacetica, Sporomusa sphaeroides, Oxobacter pfennigii*, and *Thermoanaerobacter kivui*.

The bacteria according to an embodiment, which are a *Clostridium* species selected from the group consisting of *C. ljungdahlii*, and *C. autoethanogenum*.

The bacteria according to an embodiment, further comprising a nucleic acid encoding acetyl-Coenzyme A carboxylase, wherein the nucleic acid is codon optimized for expression in the bacteria.

The bacteria according to an embodiment, wherein the acetyl-Coenzyme A carboxylase is derived from a member of the genus *Clostridium, Metallosphaera, Sulfolobus*, or *Chloroflexus*.

The bacteria according to an embodiment, wherein the nucleic acid encoding a group of exogenous enzymes comprising β-alanine pyruvate aminotransferase and malonic semialdehyde reductase is codon optimized for expression in the bacteria.

The bacteria according to an embodiment, further comprising a nucleic acid encoding a group of exogenous enzymes comprising aldehyde::ferredoxin oxidoreductase and alcohol dehydrogenase, wherein the nucleic acid is operably linked to a promoter.

The bacteria according to an embodiment, wherein the nucleic acid encoding a group of exogenous enzymes enable production of 1,3-propanediol.

The bacteria according to an embodiment, further comprises at least one disruptive mutation in a gene encoding an enzyme selected from aldehyde::ferredoxin oxidoreductase, alcohol dehydrogenase, or any combination thereof.

The bacteria according to an embodiment, wherein 3-HP is converted into a material selected from the group consisting of acrylic acid, acrylonitrile, paint, paper, adhesives, textiles, specialty coatings, ink, superabsorbent polymer polyacrylates, 1,3-propanediol, solvents, adhesives, cosmetics, polytrimethylene terephthalate, 3-hydroxypropionaldehyde, foods, feed additives, and any combination thereof.

A method of converting CO and/or $CO_2$ into 3-hydroxyproprionate (3-HP), the process comprising: passing a gaseous CO-containing and/or $CO_2$-containing substrate to a bioreactor containing a culture of a recombinant C1-fixing bacteria according to claim 1, in a culture medium such that the bacteria convert the CO and/or $CO_2$ to 3-HP; and recovering the 3-HP from the bioreactor.

A method of culturing the bacteria according to an embodiment, comprising growing the bacteria in a medium comprising a gaseous carbon source, wherein the carbon source comprises CO and/or $CO_2$.

A method of culturing the bacteria according to an embodiment, comprising growing the bacteria in a medium comprising an energy source, wherein the energy source comprises CO and/or $CO_2$.

The method according to an embodiment, wherein the culturing is strictly anaerobic.

The method according to an embodiment, wherein the culturing is strictly anaerobic.

The method according to an embodiment, wherein the carbon source comprises an industrial waste product or off-gas.

The method according to an embodiment, wherein the energy source comprises an industrial waste product or off-gas.

The method according to an embodiment, wherein 3-HP is converted into a material selected from the group consisting of acrylic acid, acrylonitrile, paint, paper, adhesives, textiles, specialty coatings, ink, superabsorbent polymer polyacrylates, 1,3-propanediol, solvents, adhesives, cosmetics, polytrimethylene terephthalate, 3-hydroxypropionaldehyde, foods, feed additives, and any combination thereof.

The method according to an embodiment, wherein 3-HP is converted into a material selected from the group consisting of acrylic acid, acrylonitrile, paint, paper, adhesives, textiles, specialty coatings, ink, superabsorbent polymer polyacrylates, 1,3-propanediol, solvents, adhesives, cosmetics, polytrimethylene terephthalate, 3-hydroxypropionaldehyde, foods, feed additives, and any combination thereof.

EXAMPLES

The following examples further illustrate the methods and compositions of the disclosure but should not be construed to limit its scope in any way.

In this work, combinatorial analysis of the aspartate-1-decarboxylase (PAND), β-alanine pyruvate aminotransferase (BAPAT), γ-aminobutyrate transaminase (GABT), malonic semialdehyde reductase (MSR), 2,3-alanine aminomutase (AAM), alanine transaminase (AT), and alanine dehydrogenase (ALADH) was carried out in C1-fixing bacteria to improve 3-HP selectivity and production. The 3-HP biosynthesis pathway and the genes that were heterologously expressed in the following Examples are highlighted in FIG. 1.

Example 1. 3-HP Tolerance of *C. autoethanogenum* in Schott Bottles

Figure 2A:
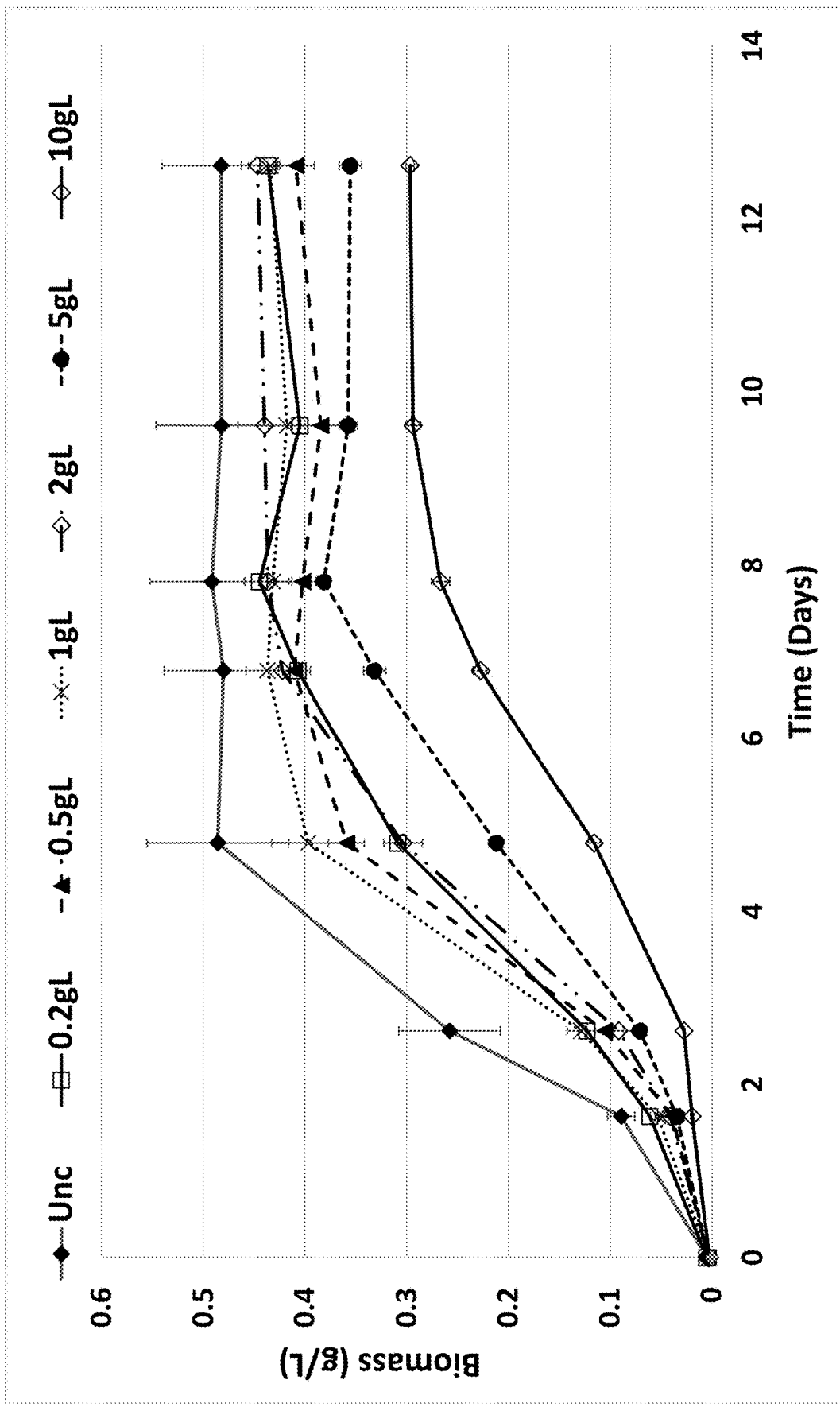
FIGS. 2A-2B show autotrophic growth of *Clostridium autoethanogenum* Δaor strain in the presence of different amounts of 3-hydroxypropionic acid (at 0, 0.2, 0.5, 1, 2, 5 and 10 g/L) in Schott bottles.
Figure 2B:
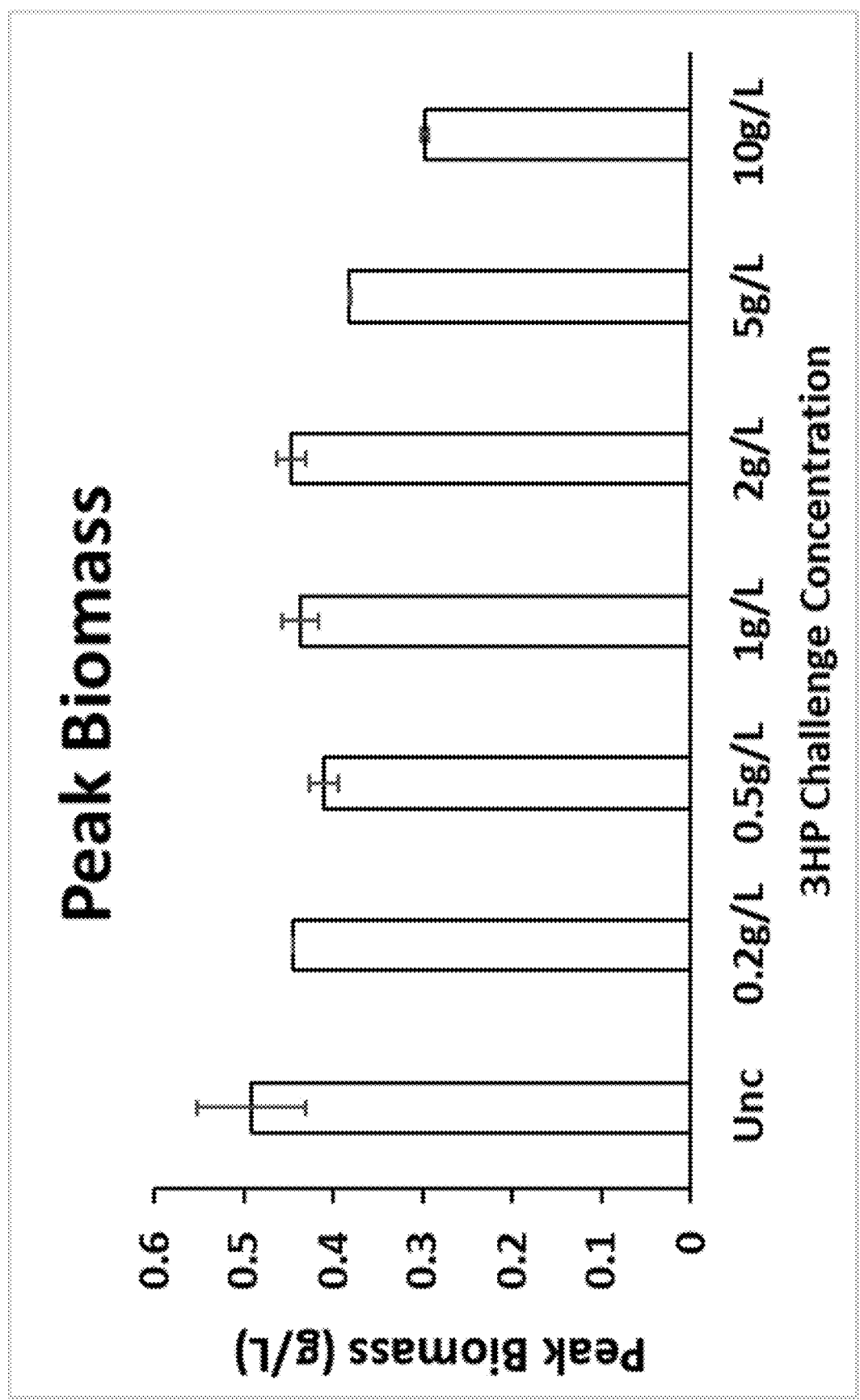

3-HP has been shown to be toxic to microorganisms such as Synechococcus *elongatus* with a minimal inhibitory concentration of 180 mg/L (Begemann et al., *PLoS One*. 2013; 8:e76594). To study the toxicity of 3-HP on autotrophic growth of *C. autoethanogenum*, a 3-HP challenge experiment (at 0, 0.2, 0.5, 1, 2, 5 and 10 g/L) was conducted in Schott bottles with synthetic gas blend (50% CO, 10% $H_2$, 30% $CO_2$ and 10% $N_2$) using a strain with aldehyde::ferredoxin oxidoreductase (AOR) enzymes deleted (FIG. 2). In comparison to the unchallenged culture, 5 g/L of 3-HP reduced the growth rate and reduced peak $OD_{600\ nm}$ by 22%. At 10 g/L 3-HP, a decrease in peak $OD_{600\ nm}$ of 40% was observed and accompanied by a more pronounced decrease in growth rate. FIG. 2A shows growth profile; FIG. 2B shows peak biomass. Unc=Unchallenged; N=2; Error bar=S.D.

Example 2. Conversion of Exogenously Added 3-HP to 1,3-Propanediol (1,3-PDO) in *C. autoethanogenum*

Figure 3:
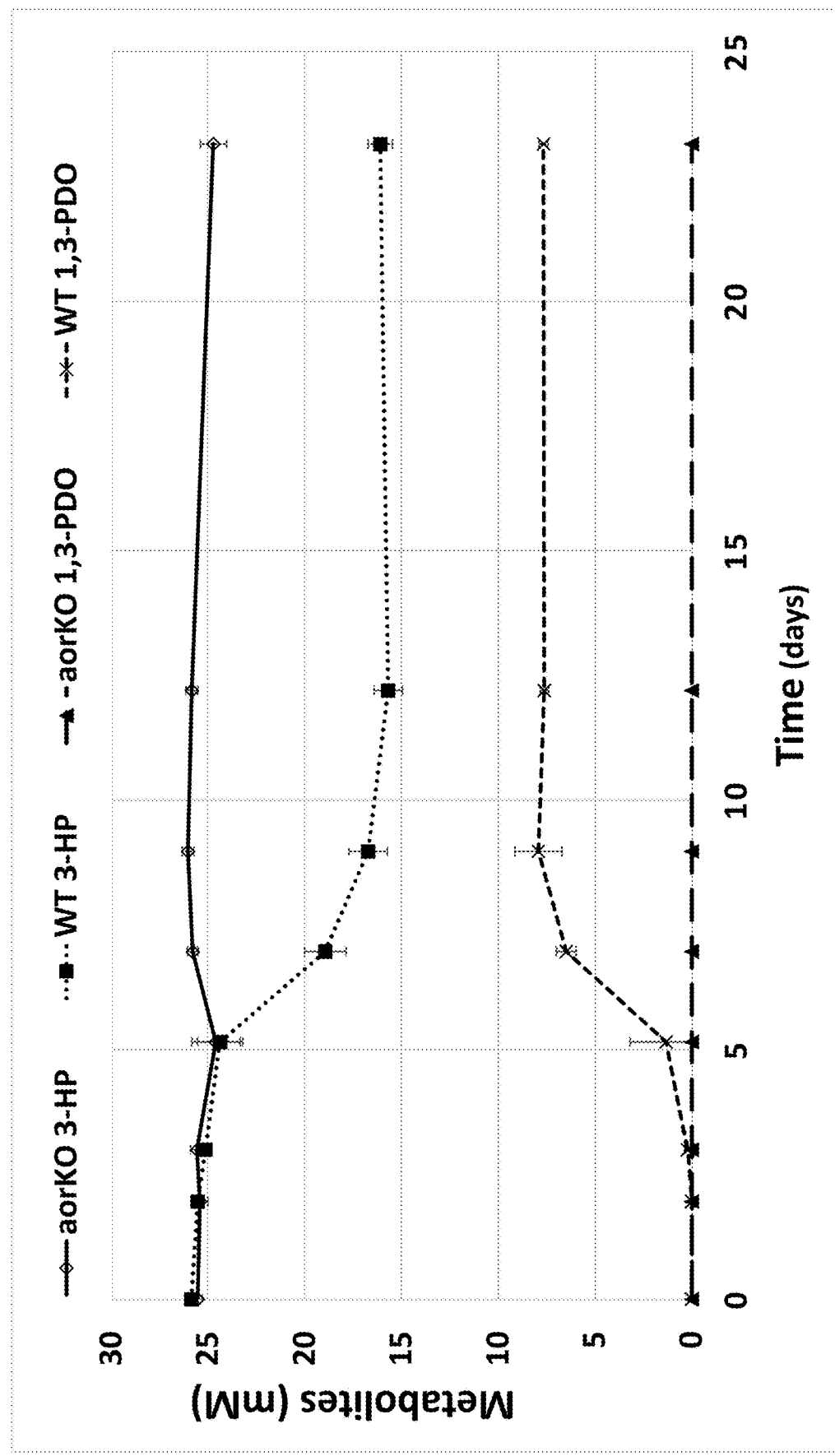
FIG. 3 shows that *Clostridium autoethanogenum* is able to convert exogenous 3-hydroxypropionic acid to 1,3-propanediol during autotrophic growth in Schott bottles. The deletion of aldehyde::ferredoxin oxidoreductase (AOR) stops this native reaction from occurring in *C. autoethanogenum*. N=2; Error bar=S.D.

The genome of *C. autoethanogenum* encodes two AOR enzyme variants and they were shown to be reduce a range of carboxylic acids (including propanoic acid and butyric acid) to the corresponding aldehydes, followed by native alcohol dehydrogenase activities that result in alcohols (Liew et al., Metabolic Engineering. 2017: 104-114.). To test if *C. autoethanogenum* is able to convert 3-HP to 1,3-propanediol (1,3-PDO) via 3-hydroxypropionaldehyde, exogenous 3-HP was added to growth medium of *C. autoethanogenum* at 25 mM (2.25 g/L) concentration and subjected to autotrophic growth in Schott bottles. As shown in FIG. 3, the *C. autoethanogenum* wild-type (WT) strain is able to convert some of the added 3-HP to 1,3-PDO at similar molar concentrations. In contrast, the aor deletion strain was unable to generate any 1,3-PDO under the same growth conditions.

Example 3. Combinatorial Analysis of 3-HP Pathway

Figure 4:
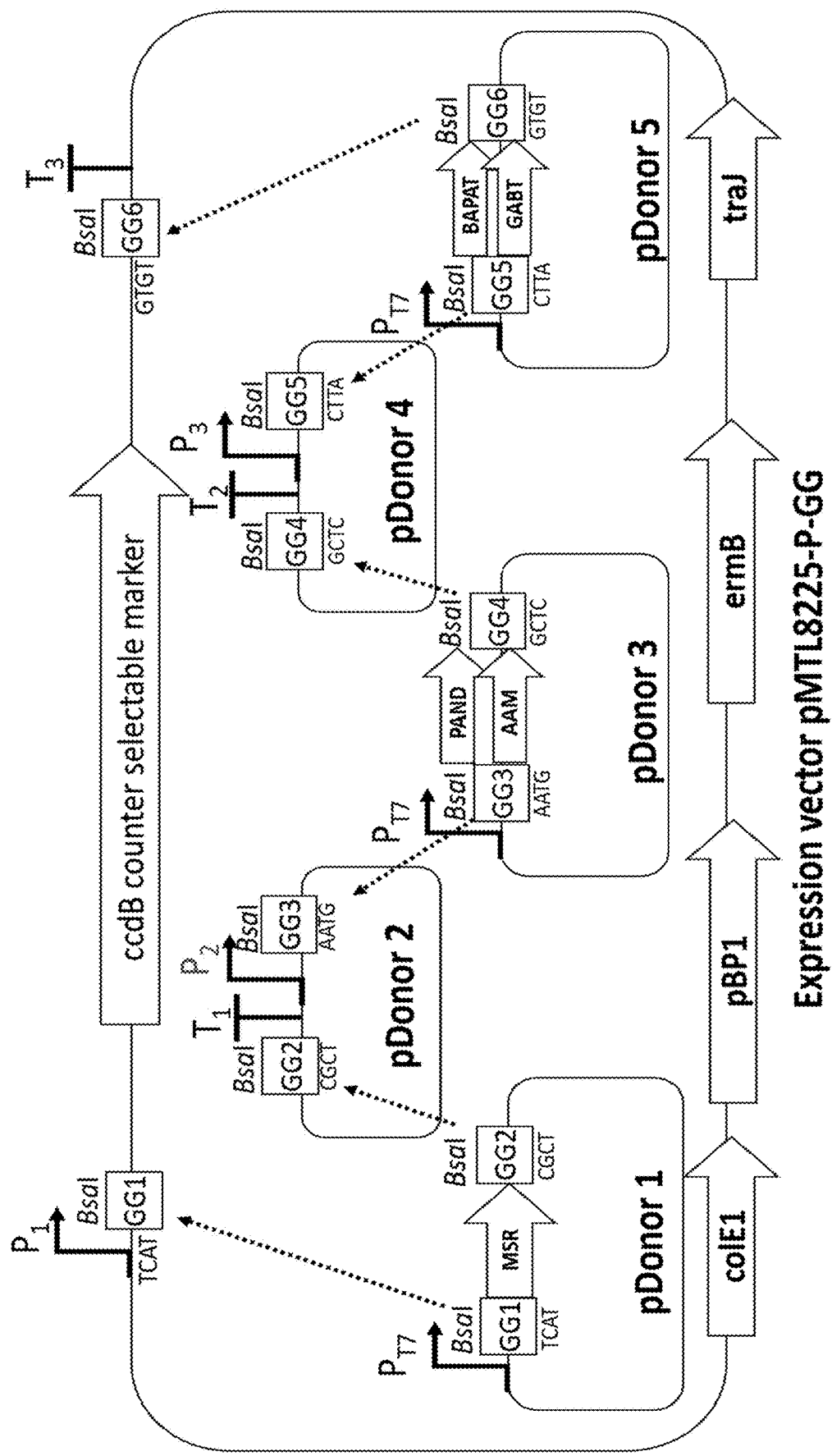
FIG. 4 shows combinatorial assembly of 3-hydroxypropionic acid pathway genes using the Golden Gate (GG) method.

In order to determine the optimum flux and gene variants for the biosynthesis of 3-HP, a combinatorial assembly of the 3-HP pathway genes and promoters using the Golden Gate (GG) method was first performed in *Escherichia coli* (FIG. 4) before transformation into C1-utilizing microorganisms. To facilitate the screening of assembly, a ccdB toxin-antitoxin counter-selectable marker flanked by Golden Gate site GG1 and GG6 was first cloned into *Clostridium-E. coli* shuttle vector pMTL8225 (Heap, J Microbiol Methods, 78: 79-85, 2009). These shuttle vectors have a pre-cloned clostridial promoter (shown as $P_1$ in FIG. 4) and terminator (shown as T3 in FIG. 4). The genes that encode aspartate-1-decarboxylase (PAND), β-alanine pyruvate aminotransferase (BAPAT), γ-aminobutyrate transaminase (GABT), malonic semialdehyde reductase (MSR), and 2,3-alanine aminomutase (AAM), together with two donor vectors (pDonor 2 and pDonor 4, which provide the terminators and promoters), were added to the shuttle vectors for GG assembly. The promoter sequences, Golden Gate sites, and assembly workflow are described in Karim et al. Synthetic Biology. 2020; 5(1): ysaa019. The resulting combinatorial plasmids with ermB antibiotic selectable marker have a promoter and terminator to express each of MSR, PAND/AAM and BAPAT/GABT in an insulated manner. The gene variants (7×MSR (SEQ ID NOs: 1-7), 5×PAND (SEQ ID NOs: 8-12), 4×BAPAT/GABT (SEQ ID NOs: 13-16), and 2×AAM (SEQ ID NOs: 17-18) that were included in the combinatorial analysis are shown in Table 2. When combined with a choice of three clostridial promoters per gene, the total permutation of this combinatorial library is 5292 (from 3×7×3×7×3×4).

TABLE 2

3-HP pathway gene variants employed for combinatorial analysis.

| Enzyme | Gene [SEQ ID NO] | Description | Reference |
|---|---|---|---|
| Malonic Semialdehyde Reductase (MSR) (E.C. 1.1.1.59 or 1.1.1.295) | bcMSR [1] | *Bacillus cereus* | Yao et al. Applied Biochemistry and Biotechnology. 2010; 160: 694-703 |
| | pdMSR [2] | *Pseudomonas denitrificans* | Zhou et al. PLOS ONE. 2013; 8(5): e62666 |
| | nmMSR [3] | *Nitrosopumilus maritimus* | Otte et al. Applied and Environmental Microbiology. 2015; 81(5): 1700-1707 |
| | ecMSR [4] | *Escherichia coli* | Fujisawa et al. Biochimica et Biophysica Acta - Proteins and Proteomics. 2003; 1645(1): 89-94 |
| | scMSR [5] | *Saccharomyces cerevisiae* | Fujisawa et al. Biochimica et Biophysica Acta - Proteins and Proteomics. 2003; 1645(1): 89-94 |
| | msMSR [6] | *Metallosphaera sedula* | Kockelkorn et al. Journal of Bacteriology. 2009; 191(20): 6352-6362 |
| | caMSR-N [7] | N-terminus of *Chloroflexus aurantiacus* malonyl-CoA reductase | Liu et al. PLOS ONE. 2013; 8(9): e75554 |
| Aspartate Decarboxylase (PAND) (E.C. 4.1.1.11) | cgPAND [8] | *Corynebacterium glutamicum* | Dusch et al. Applied and Environmental Microbiology. 1999; 65(4): 1530-1539 |
| | caPAND [9] | *Clostridium acetobutylicum* | Annan et al. Applied Microbiology and Biotechnology. 2019; 103(11): 4633-4648 |
| | ecPAND [10] | *Escherichia coli* | Borodina et al. Metabolic Engineering. 2015; 27: 57-64 |
| | tcPAND [11] | *Tribolium castaneum* | Borodina et al. Metabolic Engineering. 2015; 27: 57-64 |
| | mjPAND [12] | *Methanocaldococcus jannaschii* | Wang et al. Journal of Bacteriology. 2014; 196(15): 2869-2875 |

TABLE 2-continued

3-HP pathway gene variants employed for combinatorial analysis.

| Enzyme | Gene [SEQ ID NO] | Description | Reference |
|---|---|---|---|
| β-Alanine Aminotransferase (BAPAT) or γ-aminobutyrate transaminase (GABT) (E.C. 2.6.1.19) | paBAPAT [13] | *Pseudomonas aeruginosa* | Song et al. ACS Synthetic Biology. 2016; 5(11): 1256-1263 |
| | bcBAPAT [14] | *Bacillus cereus* YHXA gene | Borodina et al. Metabolic Engineering. 2015; 27: 57-64 |
| | ppBAPAT [15] | *Pseudomonas putida* | Song et al. ACS Synthetic Biology. 2016; 5(11): 1256-1263 |
| | skGABT [16] | *Saccharomyces kluyveri* | Andersen et al. FEBS Journal. 2007; 274 (7): 1804-1817 |
| 2,3-Alanine Aminomutase (AAM) (E.C. 5.4.3.a) | pgAAM [17] | *Porphyromonas gingivalis* | U.S. Pat. No. 7,655,451 B2 |
| | bsAAM [18] | *Bacillus subtilis* | U.S. Pat. No. 7,655,451 B2 |

To determine the assembly efficiency of combinatorial plasmids in *E. coli*, and to investigate the promoter and gene variant combinations, 192 plasmids were extracted from transformed *E. coli* strain NEB10-beta and subjected to sequencing. Analysis of the sequencing results showed an assembly rate of 99%, and all the promoters and gene variants employed were represented without significant bias. Following transformation of these sequence-verified combinatorial plasmids into *C. autoethanogenum*, a total of 111 combinatorial strains were subjected to autotrophic growth in 12-well plates.

Figure 5A:
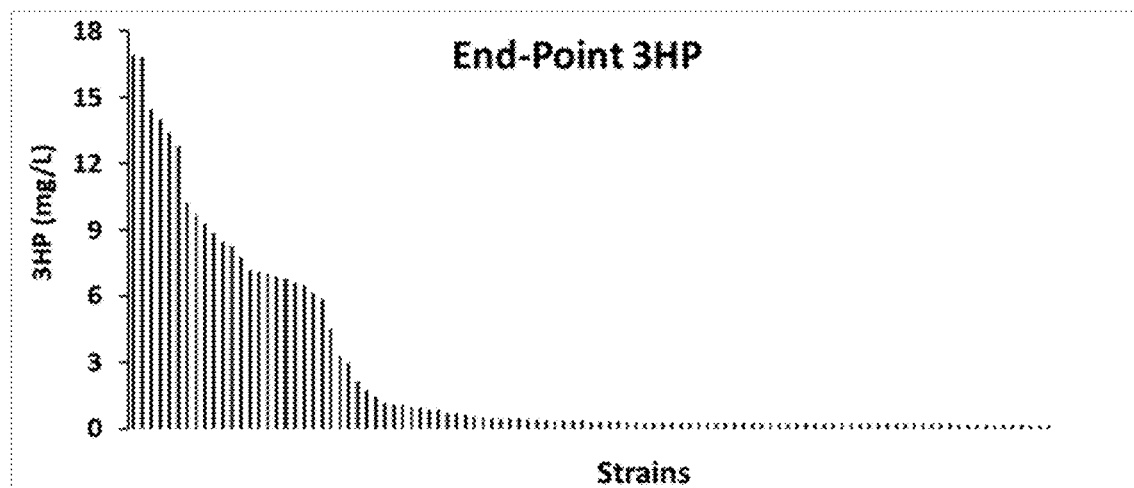
FIGS. 5A-C show characterization of 111 3-hydroxypropionic acid (3-HP) combinatorial strains in 12-well plates with 200 kPa synthetic gas blend (50% CO, 10% $H_2$, 30% $CO_2$, and 10% $N_2$).
Figure 5B:
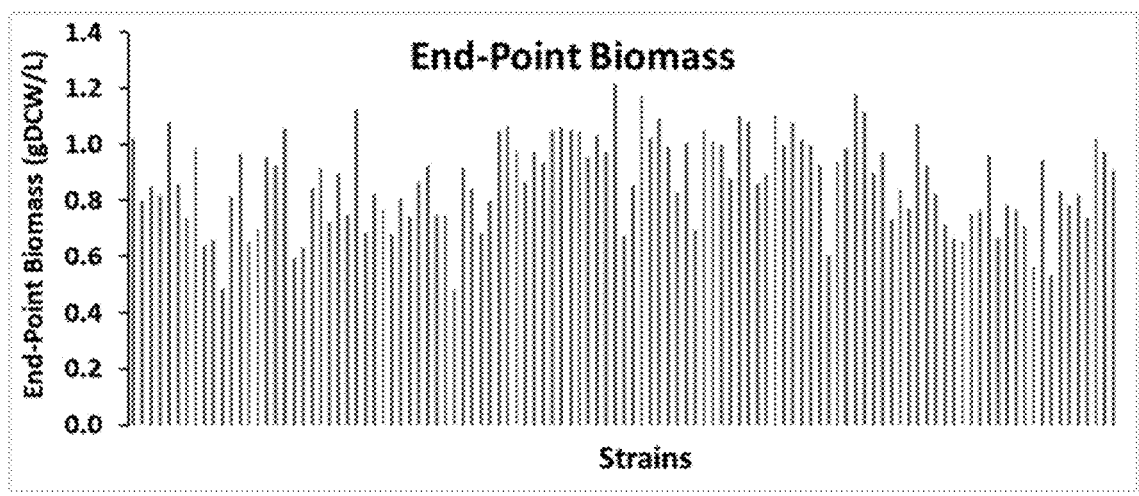
Figure 5C:
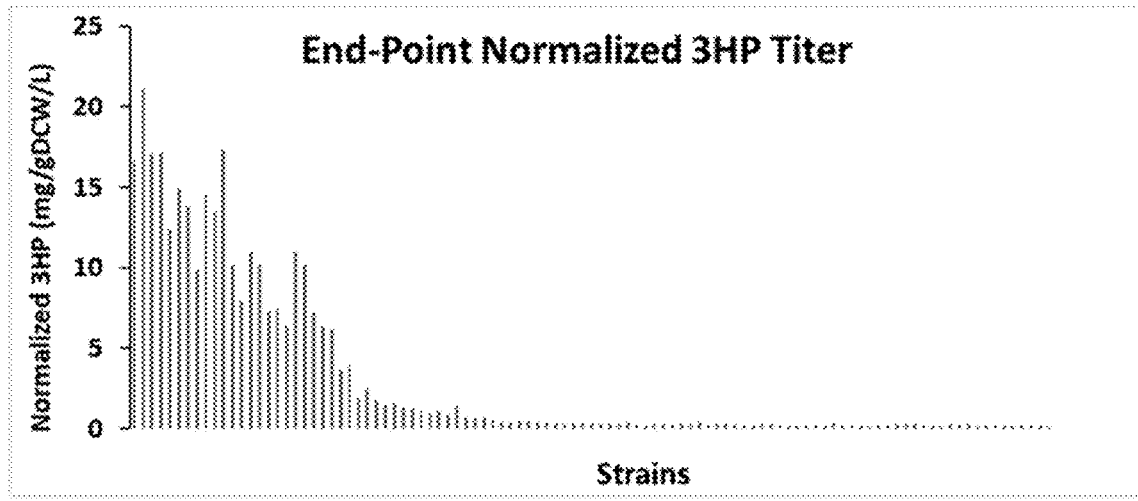

Growth experiments were conducted in 12-well plates with 2 mL minimal media and 200 kPa of synthetic gas mix (50% CO, 10% $H_2$, 30% $CO_2$, and 10% $N_2$) at 37° C. for 8 days (FIGS. 5A-C). Broth samples were then taken for biomass measurement and LC-MS analysis to determine 3-HP titer.

Following 8 days of incubation, the 3-HP combinatorial strains reached biomass concentration of 0.5-1.2 gDCW/L (FIG. 5B). Out of these 111 combinatorial strains, 33 strains produced >1 mg/L 3-HP. Seven strains produced more than 10 mg/L 3-HP (17 mg/L being highest) (FIG. 5A). The genotype of the top 20 3-HP-producing strains is shown in Table 3. The 3-HP titer normalized by biomass concentration is shown in FIG. 5C.

TABLE 3

Genotype of top 20 3-HP-producing combinatorial strains in the 12-well plate growth assay.

| Strain Name | promoter 1 | gene 1 | promoter 2 | gene 2 | promoter 3 | gene 3 | 3HP (mg/L) | Biomass (gDCW/L) | Normalized 3HP (mg/gDCW/L) |
|---|---|---|---|---|---|---|---|---|---|
| A59B | Pwl | pdMSR | Ppfor | caPAND | Pfer | paBAPAT | 16.93 | 1.02 | 16.61 |
| A63B | Pfer | scMSR | Pfer | caPAND | Pwl | skGABT | 16.85 | 0.80 | 21.15 |
| A63C | Pfer | scMSR | Pfer | caPAND | Pwl | skGABT | 14.46 | 0.85 | 17.08 |
| A63A | Pfer | scMSR | Pfer | caPAND | Pwl | skGABT | 14.05 | 0.82 | 17.13 |
| A35A | Pwl | pdMSR | Pfer | cgPAND | Pfer | paBAPAT | 13.40 | 1.08 | 12.42 |
| A59A | Pwl | pdMSR | Ppfor | caPAND | Pfer | paBAPAT | 12.82 | 0.86 | 14.91 |
| A59C | Pwl | pdMSR | Ppfor | caPAND | Pfer | paBAPAT | 10.24 | 0.74 | 13.87 |
| A10A | Ppfor | nmMSR | Pwl | mjPAND | Pwl | ppBAPAT | 9.71 | 0.98 | 9.87 |
| A95B | Pfer | ecMSR | Pwl | cgPAND | Ppfor | paBAPAT | 9.29 | 0.64 | 14.55 |
| A36B | Pwl | nmMSR | Pfer | cgPAND | Pwl | bcBAPAT | 8.87 | 0.66 | 13.51 |
| A37B | Pwl | nmMSR | Pfer | cgPAND | Pfer | bcBAPAT | 8.44 | 0.49 | 17.34 |
| A28B | Pfer | msMSR | Pfer | mjPAND | Ppfor | paBAPAT | 8.28 | 0.82 | 10.15 |
| A20B | Pfer | scMSR | Pfer | mjPAND | Pwl | skGABT | 7.70 | 0.97 | 7.97 |
| A83A | Pfer | caMCR-N | Ppfor | cgPAND | Ppfor | pa BAPAT | 7.19 | 0.66 | 10.98 |
| A37A | Pwl | nmMSR | Pfer | cgPAND | Pfer | bcBAPAT | 7.07 | 0.69 | 10.20 |
| A20A | Pfer | scMSR | Pfer | mjPAND | Pwl | skGABT | 6.97 | 0.96 | 7.28 |
| B02A | Pwl | scMSR | Pfer | cgPAND | Ppfor | bcBAPAT | 6.84 | 0.92 | 7.41 |
| A17A | Pwl | nmMSR | Pfer | cgPAND | Pfer | bcBAPAT | 6.77 | 1.06 | 6.42 |
| A75A | Pwl | caMCR-N | Pwl | cgPAND | Pwl | pa BAPAT | 6.56 | 0.60 | 11.03 |
| A95A | Pfer | ecMSR | Pwl | cgPAND | Ppfor | pa BAPAT | 6.43 | 0.63 | 10.18 |

Figure 6:
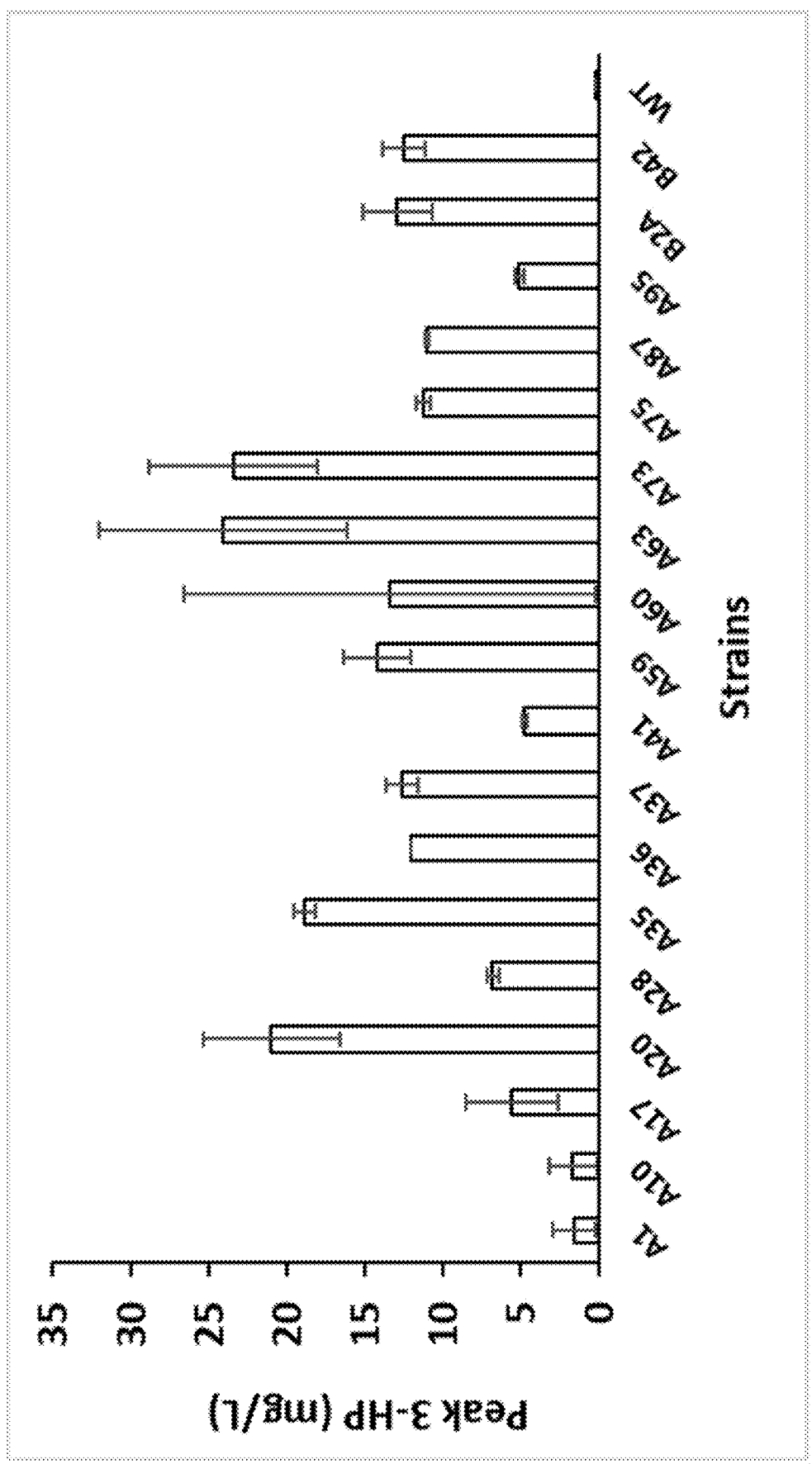
FIG. 6 shows the peak 3-hydroxypropionic acid titer from combinatorial strains and WT *C. autoethanogenum* strain during autotrophic growth in Schott bottles. Incubation duration=14 days; N=2; Error bar=S.D.

Eighteen 3-HP combinatorial strains were further subjected to autotrophic growth in 250 mL Schott bottle with 10 mL minimal media in the presence of 150 kPa synthetic gas mix (50% CO, 10% $H_2$, 30% $CO_2$, and 10% $N_2$) at 37° C. for 14 days with regular samplings for biomass measurement and 3-HP analysis. Up to 24.09±7.95 mg/L 3-HP was detected in these combinatorial strains, compared to only 0.23±0.02 mg/L 3-HP in the WT control (FIG. 6).

Example 4. 3-HP and 1,3-PDO Production from Syngas Fermentation in CSTR

3-HP combinatorial strains "A59B", "B2A" and "A63B" (Table 3) were characterized in CSTR under batch mode to compare their 3-HP production to WT *C. autoethanogenum*. Actively growing (early exponential) culture from Schott bottles was used as inoculum for 2 L CSTRs with a synthetic gas blend (50% CO, 10% $H_2$, 30% $CO_2$, and 10% $N_2$) at atmospheric pressure. 3-HP combinatorial strain "A59B" (Table 3) was also characterized in CSTR under continuous mode.

Figure 7A:
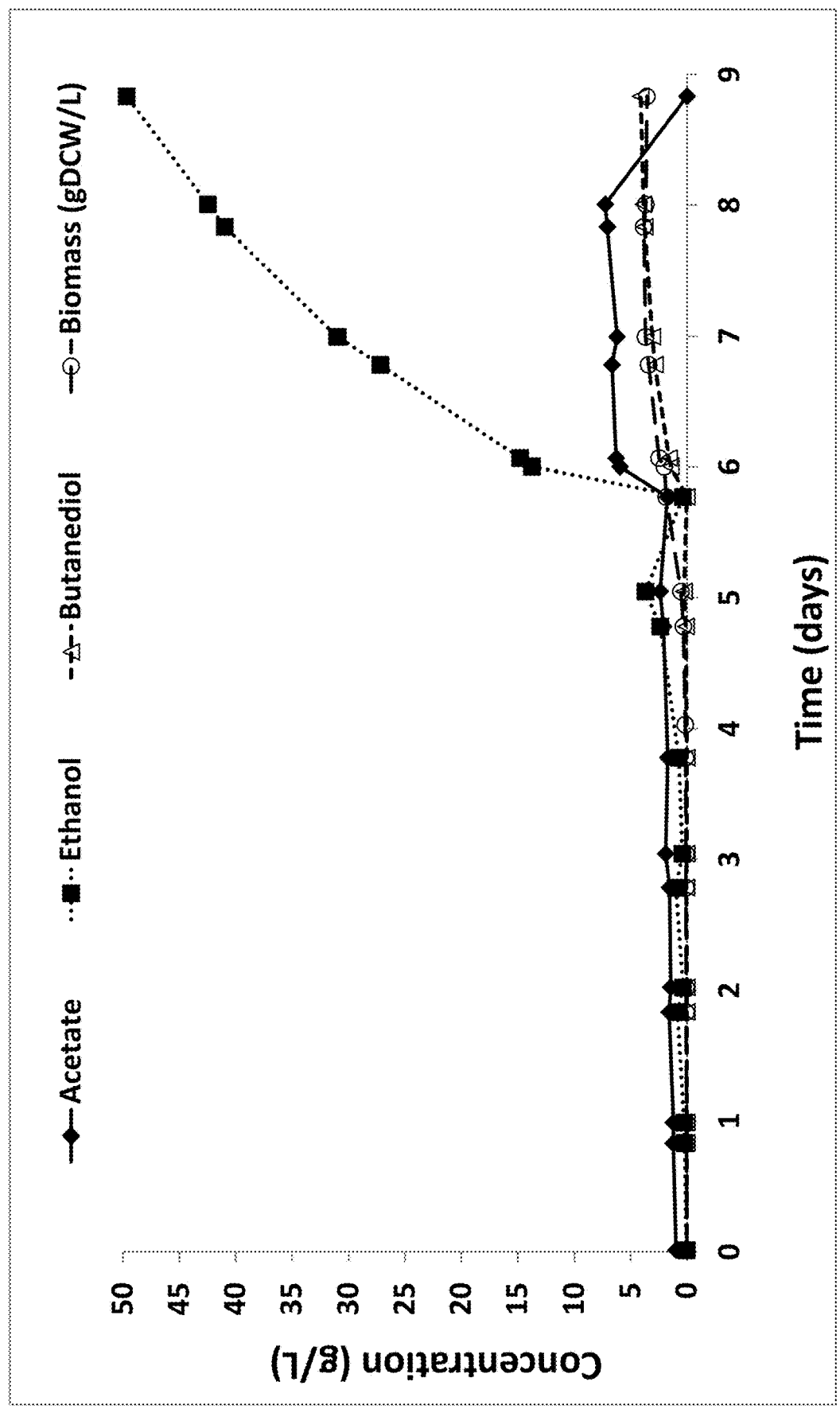
FIGS. 7A-7C show the performance of combinatorial strain A59B in batch CSTR fermentation using a synthetic gas blend (50% CO, 10% $H_2$, 30% $CO_2$ and 10% $N_2$).
Figure 7B:
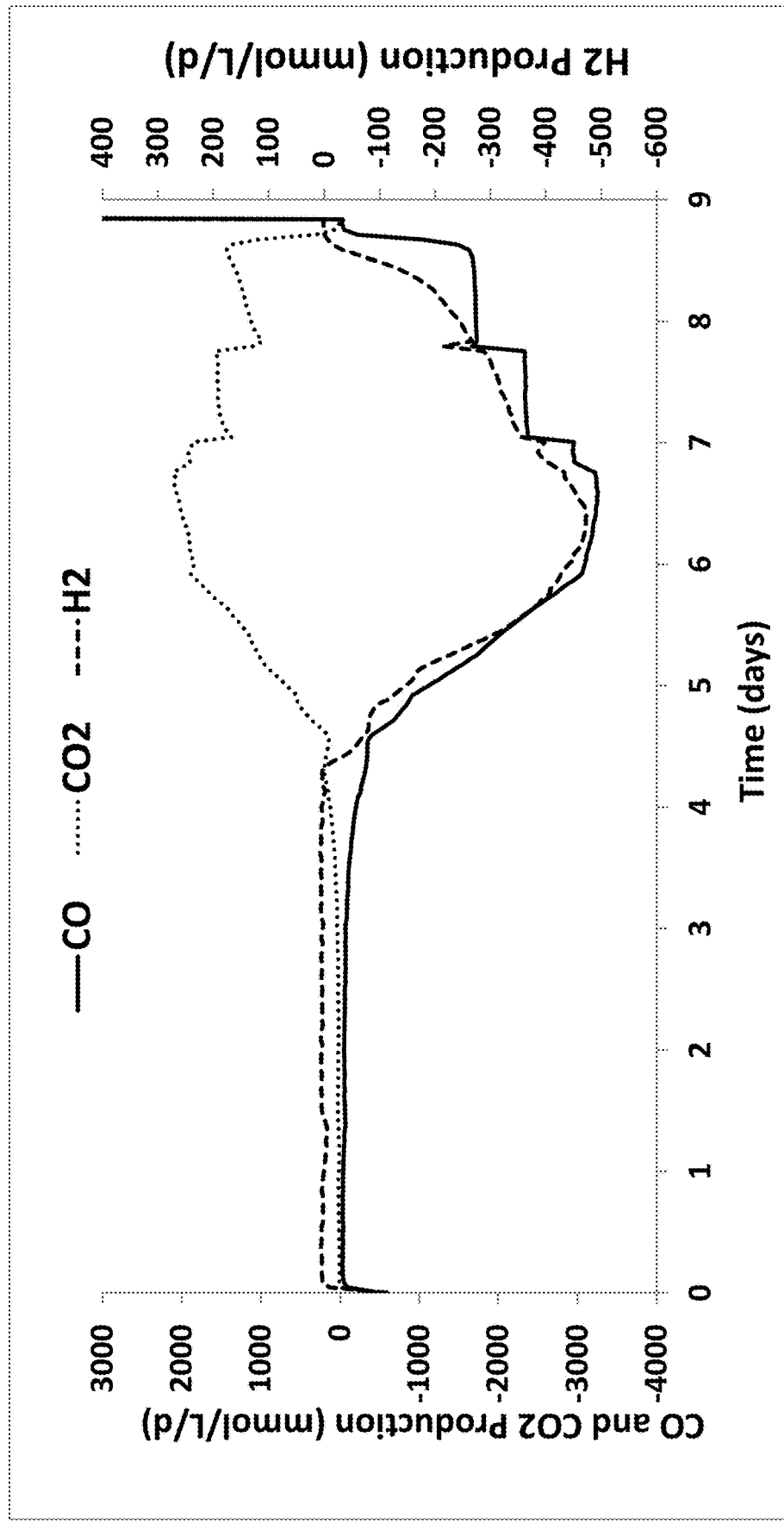
Figure 7C:
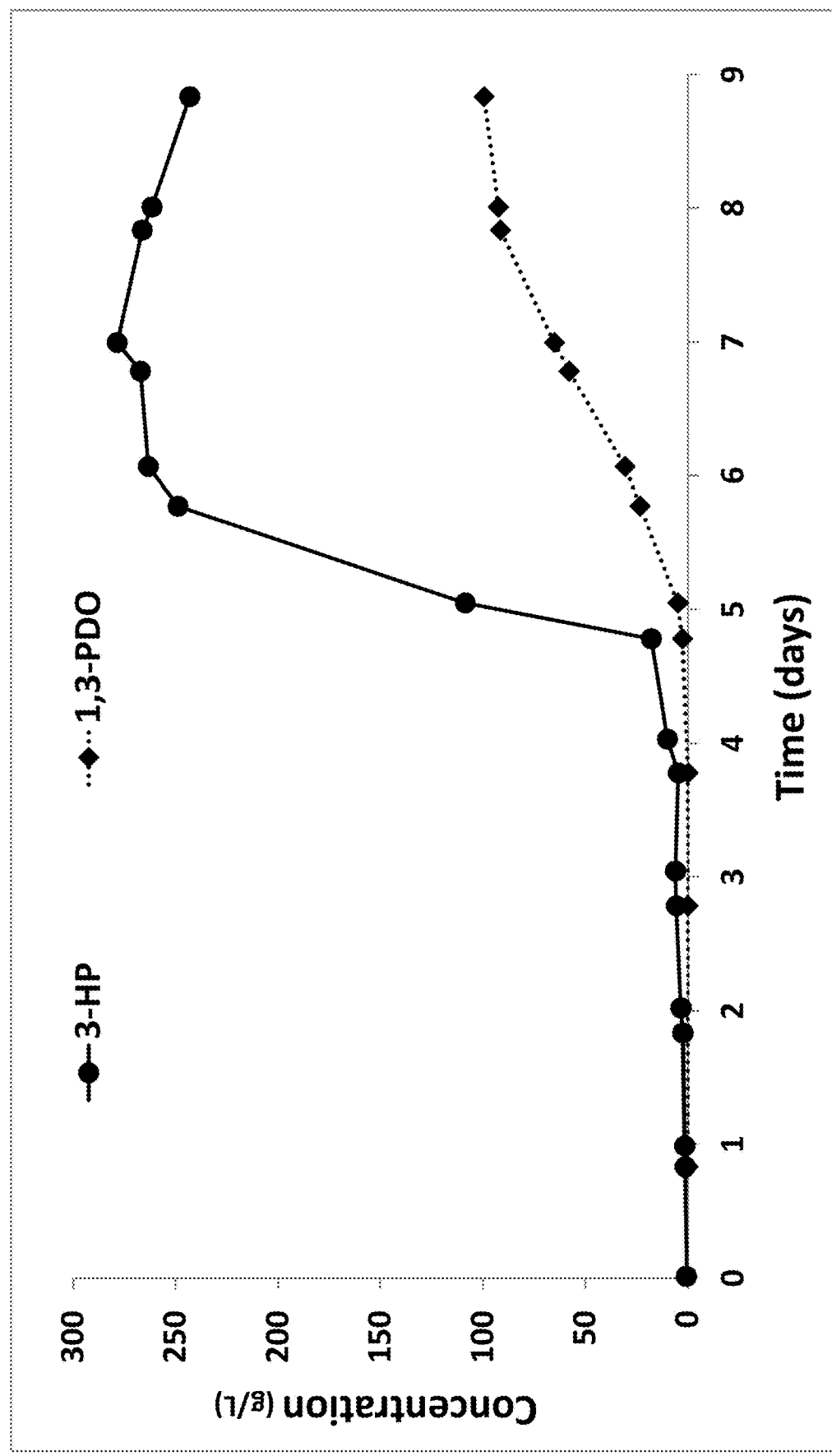

Strain A59B achieved a peak biomass concentration of 3.8 gDCW/L (FIG. 7A) and reached a peak CO uptake of 3260 mmol/L/d (FIG. 7B). In addition to a peak ethanol concentration of 50 g/L (FIG. 7A), this strain reached a peak 3-HP titer of 278.5 mg/L and peak 1,3-PDO titer of 99.5 mg/L (FIG. 7C).

Figure 8A:
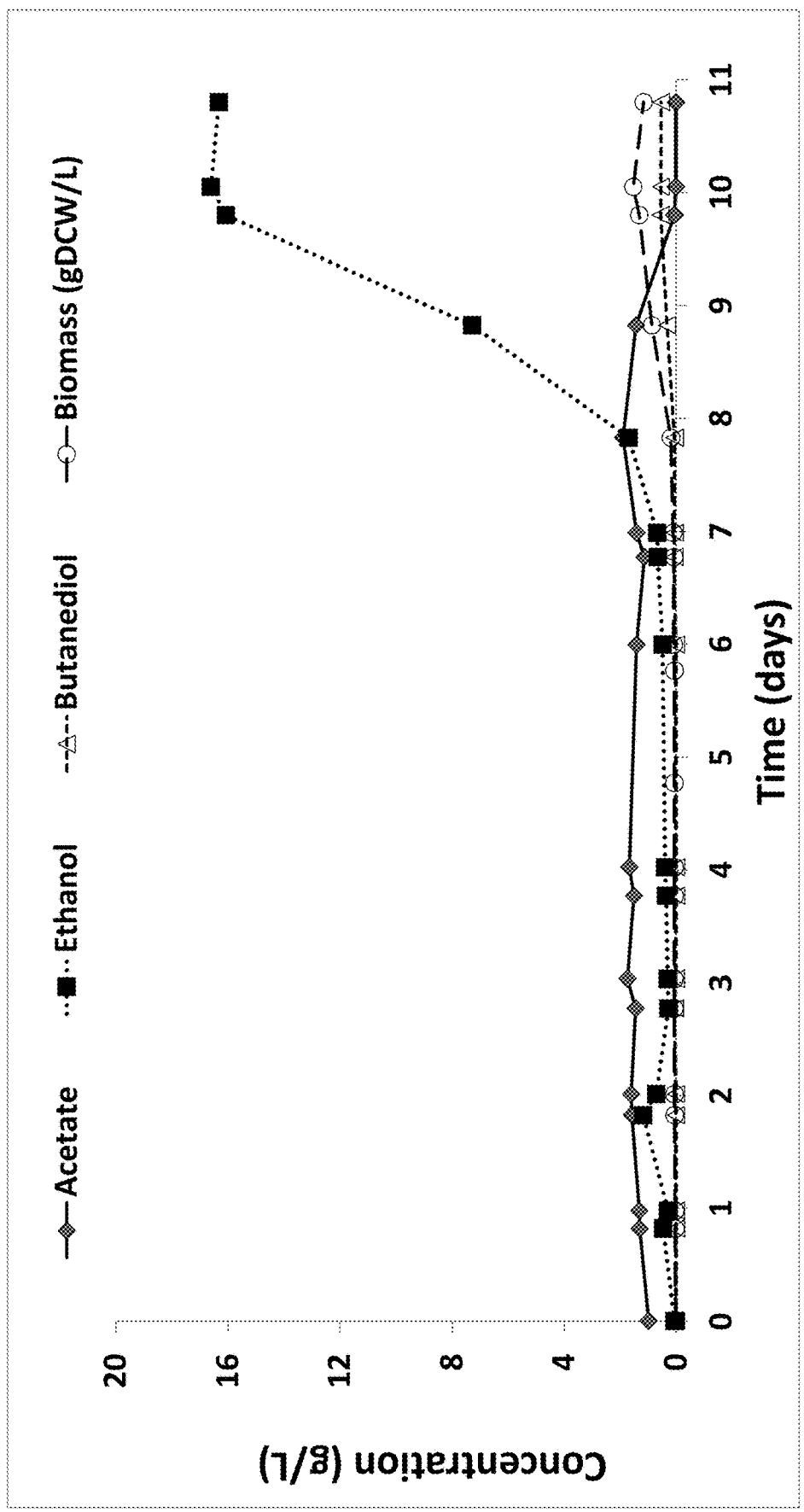
FIGS. 8A-8C show the performance of combinatorial strain B2A in batch CSTR fermentation using a synthetic gas blend (50% CO, 10% $H_2$, 30% $CO_2$ and 10% $N_2$).
Figure 8B:
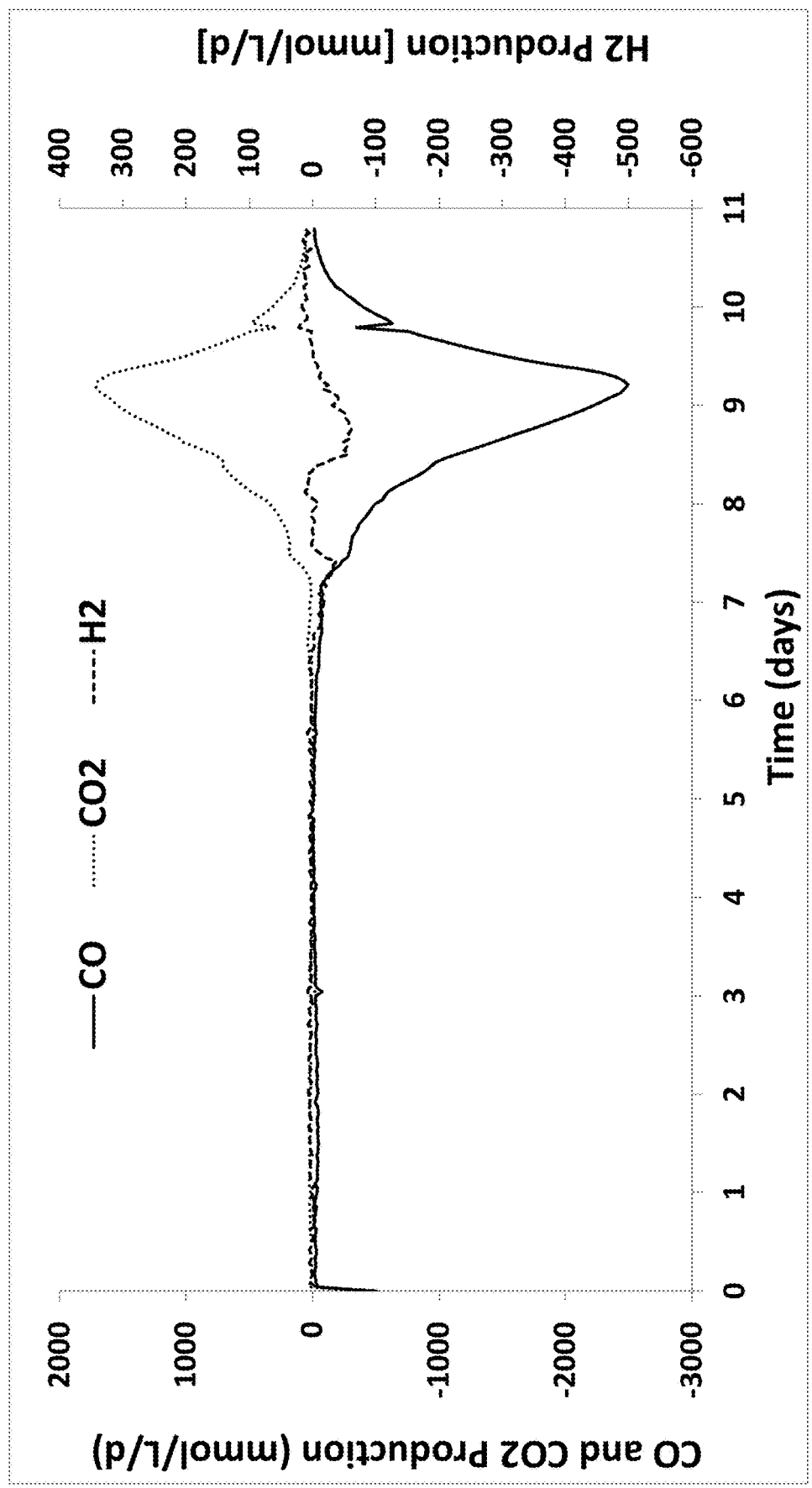
Figure 8C:
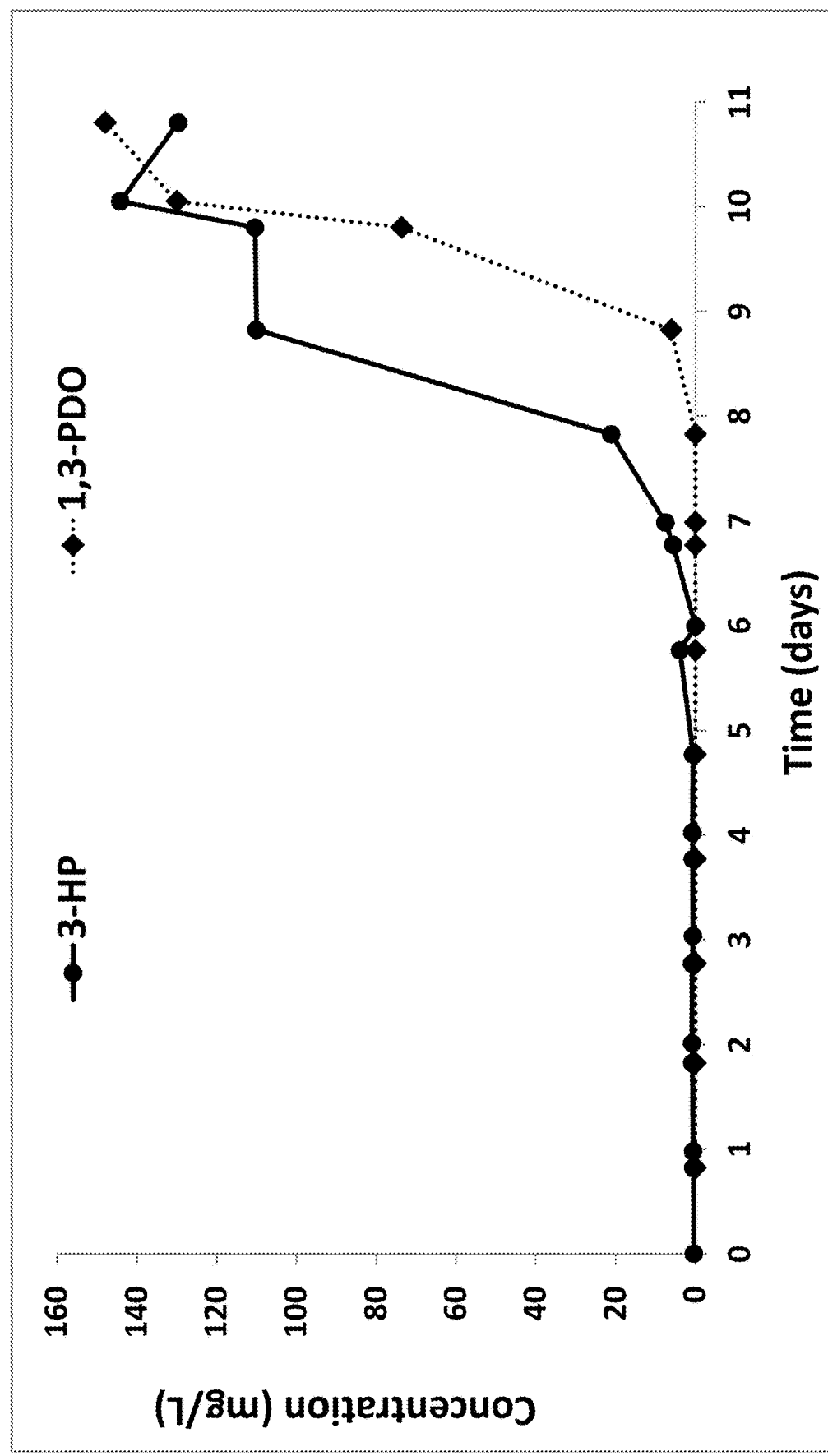

Strain B2A grew to a peak biomass concentration of 2.7 gDCW/L (FIG. 8A) and achieved a peak CO uptake of 2497 mmol/L/d (FIG. 8B) while generating a maximum ethanol titer of 16.6 g/L (FIG. 8A). In the stationary growth phase, a peak 3-HP titer of 144.2 mg/L and peak 1,3-PDO titer of 148 mg/L were measured using LC-MS and GC-MS, respectively (FIG. 8C).

Figure 9A:
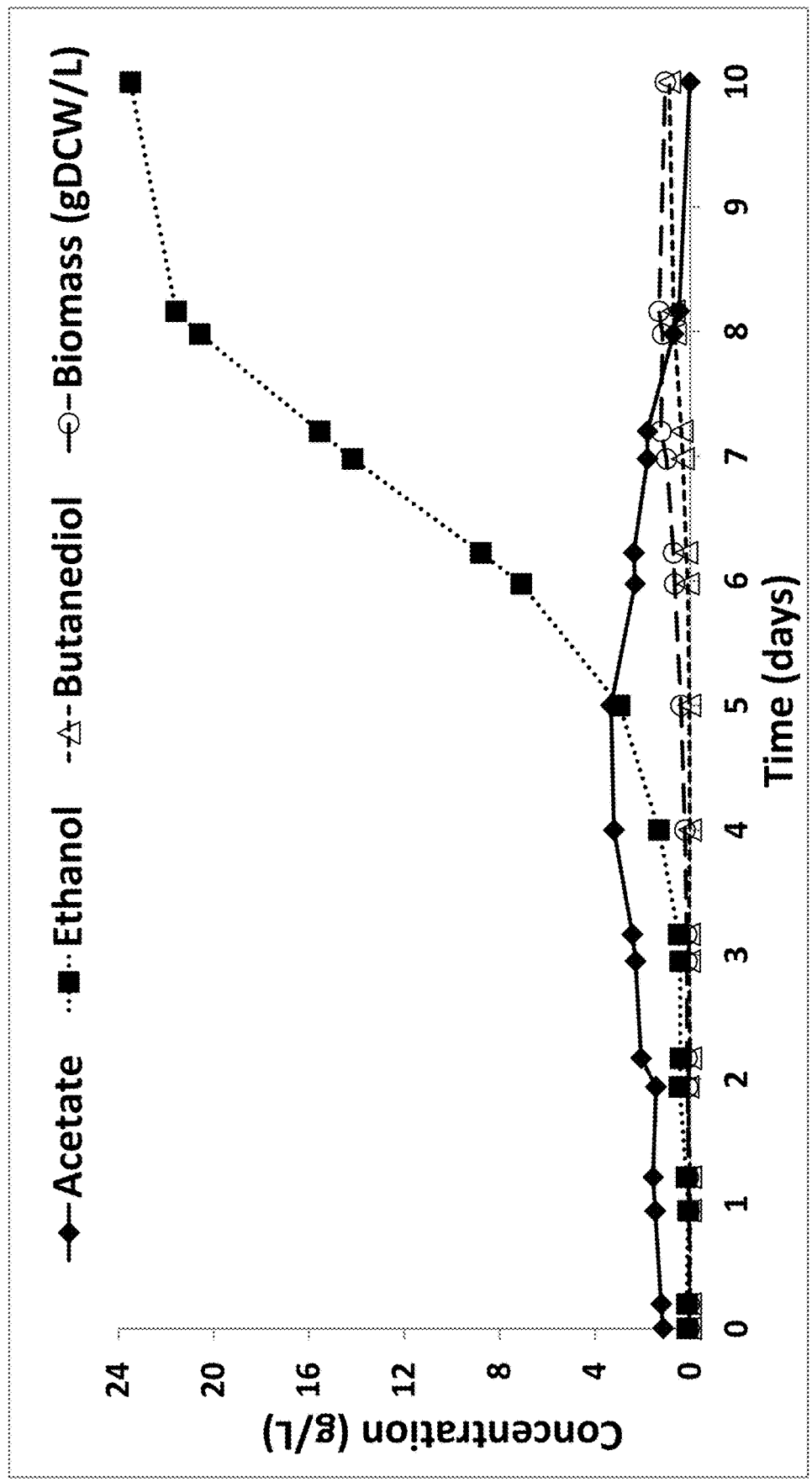
FIGS. 9A-9C show the performance of combinatorial strain A63B in batch CSTR fermentation using a synthetic gas blend (50% CO, 10% $H_2$, 30% $CO_2$ and 10% $N_2$).
Figure 9B:
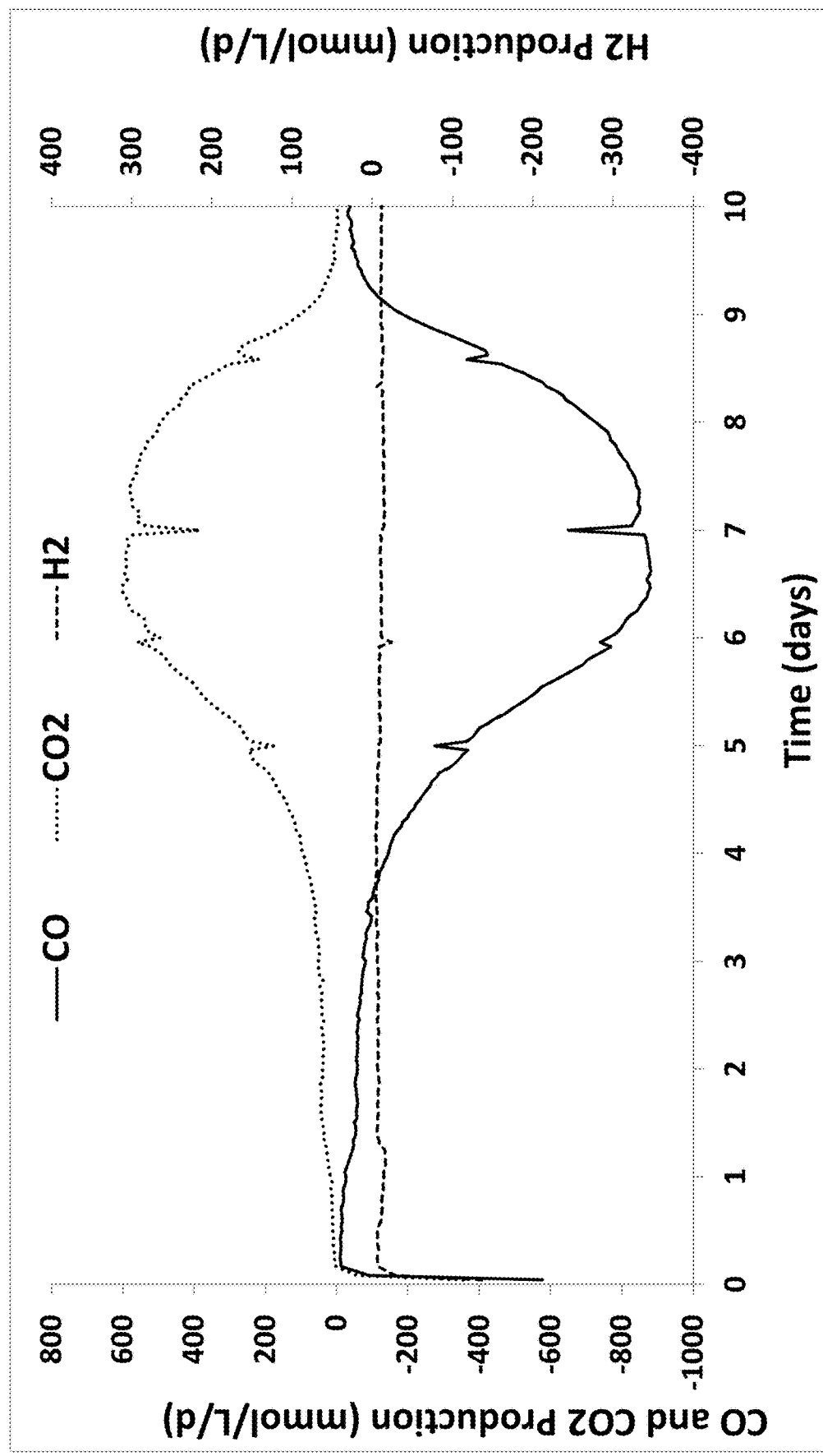
Figure 9C:
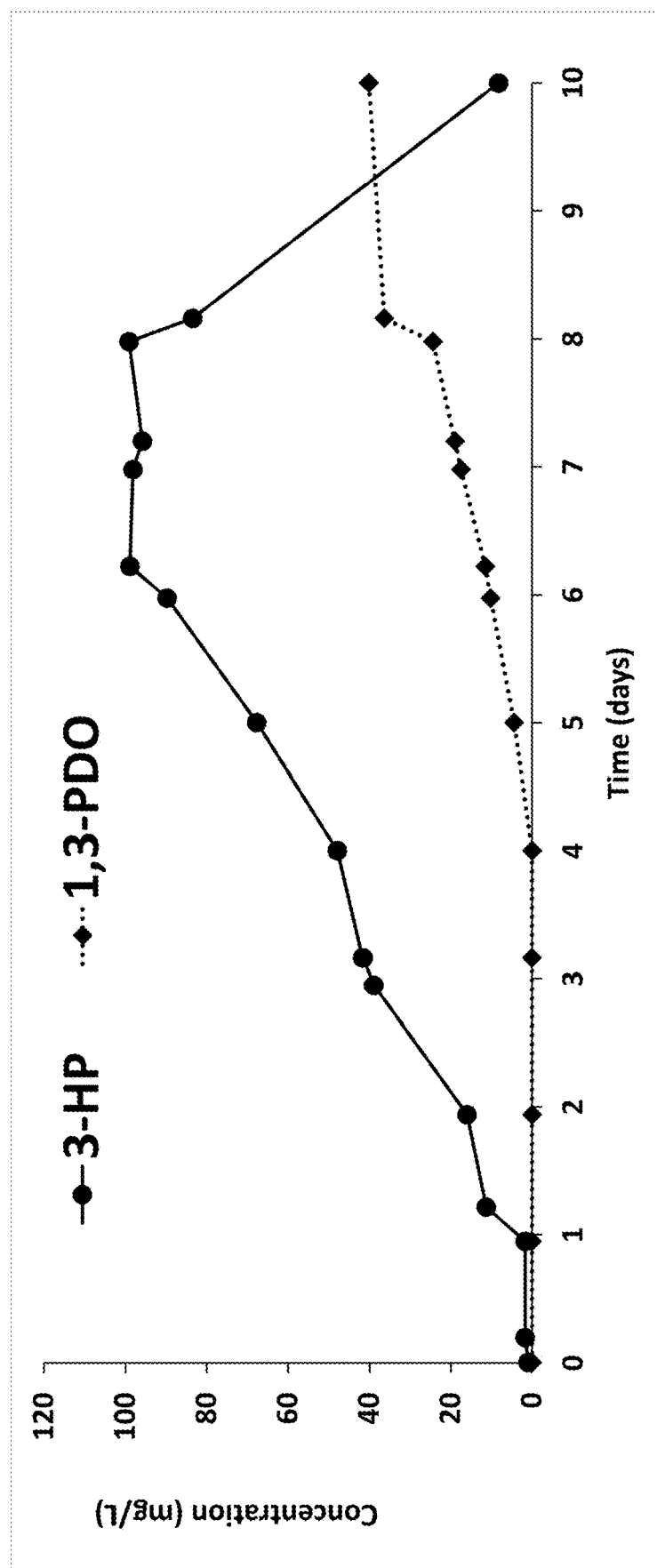

Strain A63B reached a peak biomass concentration of 1.3 gDCW/L (FIG. 9A) and reached a peak CO uptake of 880 mmol/L/d (FIG. 9B). Despite the low peak CO gas uptake, this strain was able to produce a maximum ethanol titer of 23.5 g/L (FIG. 9A), peak 3-HP titer of 99.2 mg/L and peak 1,3-PDO concentration of 40.2 mg/L (FIG. 9C).

Figure 10A:
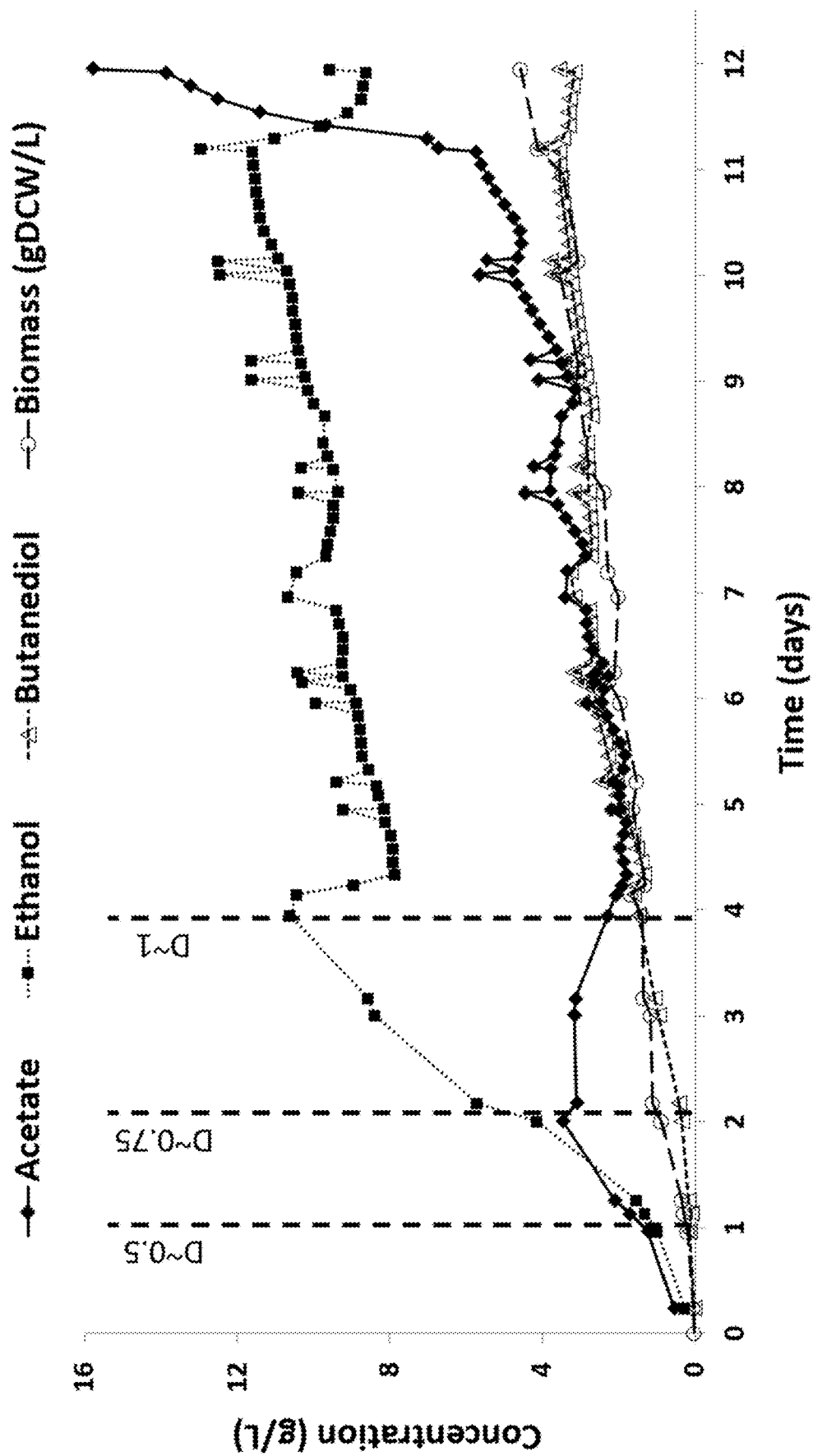
FIG. 10A-10C shows the performance of combinatorial strain A59B in continuous CSTR fermentation using a synthetic gas blend (50% CO, 10% $H_2$, 30% $CO_2$ and 10% $N_2$).
Figure 10B:
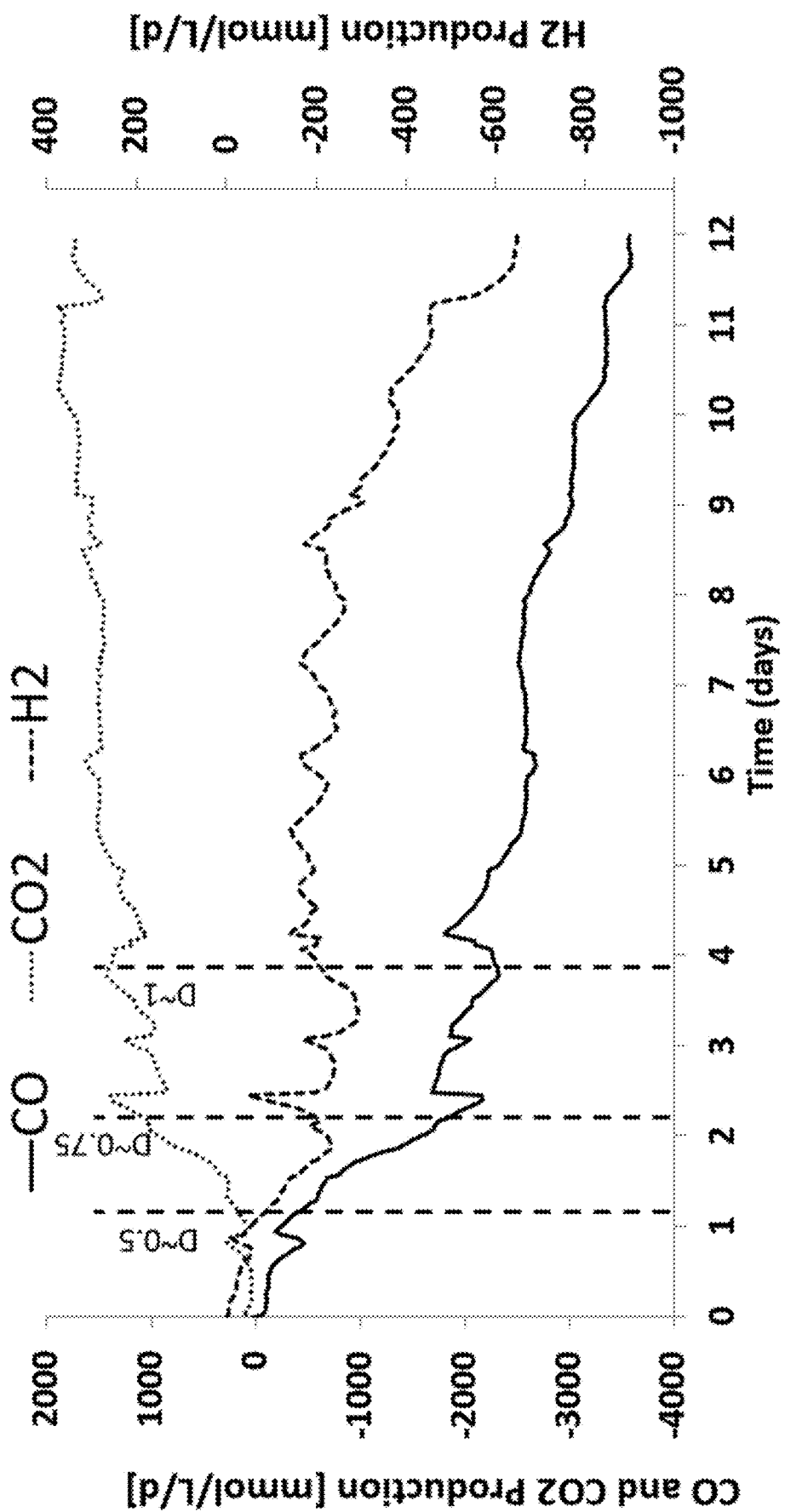
Figure 10C:
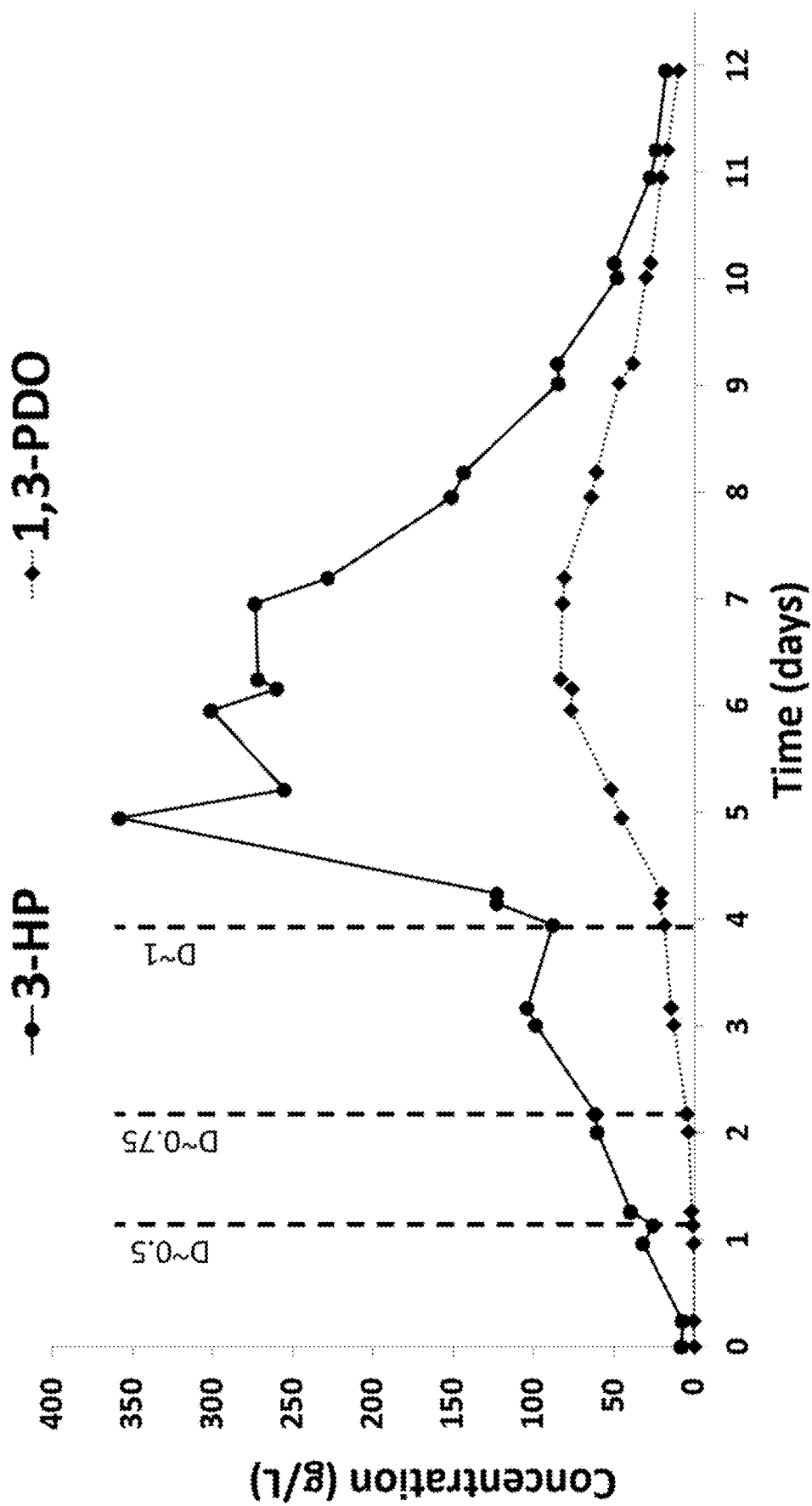

Under continuous CSTR conditions using strain A59B, a dilution (D) rate of 0.5/day was initiated on day 1.2, before increasing to D of 0.75/day on day 2.2, eventually reaching D of 1/day between day 3.9 and day 12. Biomass concentration accumulated to a peak concentration of 4.6 gDCW/L (FIG. 10A) and CO gas uptake reached a peak of 3574 mmol/L/d (FIG. 10B). Following the switch to D of 1/day, this strain achieved peak productivity of 358 mg/L/d 3-HP on day 5 and 82.2 mg/L/d 1,3-PDO on day 7 (FIG. 10C).

All references, including publications, patent applications, and patents, cited herein are hereby incorporated by reference to the same extent as if each reference were individually and specifically indicated to be incorporated by reference and were set forth in its entirety herein. The reference to any prior art in this specification is not, and should not be taken as, an acknowledgement that that prior art forms part of the common general knowledge in the field of endeavor in any country.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. The term "consisting essentially of" limits the scope of a composition, process, or method to the specified materials or steps, or to those that do not materially affect the basic and novel characteristics of the composition, process, or method. The use of the alternative (e.g., "or") should be understood to mean either one, both, or any combination thereof of the alternatives. As used herein, the term "about" means±20% of the indicated range, value, or structure, unless otherwise indicated.

Recitation of ranges of values herein are merely intended to serve as a shorthand method of referring individually to each separate value falling within the range, unless otherwise indicated herein, and each separate value is incorporated into the specification as if it were individually recited herein. For example, any concentration range, percentage range, ratio range, integer range, size range, or thickness range is to be understood to include the value of any integer within the recited range and, when appropriate, fractions thereof (such as one tenth and one hundredth of an integer), unless otherwise indicated.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Embodiments of this disclosure are described herein. Variations of those embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

The invention claimed is:

1. A recombinant C1-fixing bacteria for producing 3-hydroxypropionate (3-HP) from a carbon source comprising a nucleic acid encoding a group of exogenous enzymes comprising β-alanine pyruvate aminotransferase having SEQ ID NO: 13, 14, or 15 and malonic semialdehyde reductase.

2. The bacteria according to claim 1, further comprising a nucleic acid encoding a group of exogenous enzymes comprising pyruvate carboxylase, aspartate aminotransferase, and aspartate decarboxylase, wherein the nucleic acid is operably linked to a promoter.

3. The bacteria according to claim 1, further comprising a nucleic acid encoding a group of exogenous enzymes comprising alanine dehydrogenase and 2,3-alanine aminomutase, wherein the nucleic acid is operably linked to a promoter.

4. The bacteria according to claim 1, which are selected from the group consisting of Clostridium autoethanogenum, Clostridium ljungdahlii, Clostridium ragsdalei, Clostridium carboxidivorans, Clostridium drakei, Clostridium scatologenes, Clostridium aceticum, Clostridium formicoaceticum, Clostridium magnum, Butyribacterium methylotrophicum, Acetobacterium woodii, Alkalibaculum bacchii, Blautia producta, Eubacterium limosum, Moorella thermoacetica, Moorella thermautotrophica, Sporomusa ovata, Sporomusa silvacetica, Sporomusa sphaeroides, Oxobacter pfennigii, and Thermoanaerobacter kivui.

5. The bacteria according to claim 4, which are a Clostridium species selected from the group consisting of C. ljungdahlii, and C. autoethanogenum.

6. The bacteria according to claim 1, further comprising a nucleic acid encoding acetyl-Coenzyme A carboxylase, wherein the nucleic acid is codon optimized for expression in the bacteria.

7. The bacteria according to claim 6, wherein the acetyl-Coenzyme A carboxylase is derived from a member of the genus Clostridium, Metallosphaera, Sulfolobus, or Chloroflexus.

8. The bacteria according to claim 1, wherein the nucleic acid encoding a group of exogenous enzymes comprising β-alanine pyruvate aminotransferase and malonic semialdehyde reductase is codon optimized for expression in the bacteria.

9. The bacteria according to claim 1, further comprising a nucleic acid encoding a group of exogenous enzymes comprising aldehyde::ferrodoxin oxidoreductase and alcohol dehydrogenase, wherein the nucleic acid is operably linked to a promoter.

10. The bacteria according to claim 9, wherein the nucleic acid encoding a group of exogenous enzymes enable production of 1,3-propanediol.

11. The bacteria according to claim 1, wherein 3-HP is converted into a material selected from the group consisting of acrylic acid, acrylonitrile, paint, paper, adhesives, textiles, specialty coatings, ink, superabsorbent polymer polyacrylates, 1,3-propanediol, solvents, adhesives, cosmetics, polytrimethylene terephthalate, 3-hydroxypropionaldehyde, foods, feed additives, and any combination thereof.

12. A method of converting CO and/or $CO_2$ into 3-hydroxyproprionate (3-HP), the method comprises: passing a gaseous CO-containing and/or $CO_2$-containing substrate to a bioreactor containing a culture of a recombinant C1-fixing bacteria according to claim 1, in a culture medium such that the bacteria convert the CO and/or $CO_2$ to 3-HP; and recovering the 3-HP from the bioreactor.

13. A method of culturing the bacteria according to claim 1, comprising growing the bacteria in a medium comprising a gaseous carbon source, wherein the carbon source comprises CO and/or $CO_2$.

14. A method of culturing the bacteria according to claim 1, comprising growing the bacteria in a medium comprising an energy source, wherein the energy source comprises CO and/or $CO_2$.

15. The method according to claim 13, wherein the culturing is strictly anaerobic.

16. The method according to claim 14, wherein the culturing is strictly anaerobic.

17. The method according to claim 13, wherein the carbon source comprises an industrial waste product or off-gas.

18. The method according to claim 14, wherein the energy source comprises an industrial waste product or off-gas.

19. The method according to claim 13, wherein 3-HP is converted into a material selected from the group consisting of acrylic acid, acrylonitrile, paint, paper, adhesives, textiles, specialty coatings, ink, superabsorbent polymer polyacrylates, 1,3-propanediol, solvents, adhesives, cosmetics, polytrimethylene terephthalate, 3-hydroxypropionaldehyde, foods, feed additives, and any combination thereof.

20. The method according to claim 14, wherein 3-HP is converted into a material selected from the group consisting of acrylic acid, acrylonitrile, paint, paper, adhesives, textiles, specialty coatings, ink, superabsorbent polymer polyacrylates, 1,3-propanediol, solvents, adhesives, cosmetics, polytrimethylene terephthalate, 3-hydroxypropionaldehyde, foods, feed additives, and any combination thereof.

\* \* \* \* \*

SEQUENCE LISTING

```
<160> NUMBER OF SEQ ID NOS: 18

<210> SEQ ID NO 1
<211> LENGTH: 879
<212> TYPE: DNA
<213> ORGANISM: Artificial Sequences
<220> FEATURE:
<223> OTHER INFORMATION: LZ1561 codon adapted nucleotide sequence of
      bcMSR
```

<400> SEQUENCE: 1

```
atggaacata aaactttatc aatcggattt ataggaatag agtaatggg aaaatcaatg      60
gtttatcatt taatgcagga tggacataaa gtatatgtat acaacagaac taaagcaaaa    120
actgactcat tagttcaaga tggtgccaac tggtgcaata ctcctaaaga gctagttaaa    180
caagtggata tagttatgac tatggtagga taccctcacg atgtcgagga agtatatttt    240
ggtatagagg gtataattga acatgctaaa gagggaacaa ttgctataga cttcacaaca    300
agtactccta cattggcaaa gagaattaat gaagtagcaa agagaaaaaa tatttatact    360
cttgatgctc ctgtttcagg cggcgatgta ggagctaaag aagctaaact tgctataatg    420
gttggcggcg aaaagaaat ttatgataga tgcttaccat tattagaaaa gctaggaaca    480
aatatacagc ttcaaggacc agctggaagc ggccagcata ctaaaatgtg taatcaaatt    540
gcaatagcct ctaacatgat aggtgtatgt gaggccgtag cttacgcaaa aaaagcagga    600
ttaaatcctg ataaagtact tgaaagtata tctacaggag cagcaggatc ttggagtttg    660
tctaacctag caccacgtat gttgaaaggt gactttgaac caggattcta tgttaagcat    720
tttatgaaag atatgaaaat agcattagag gaagctgaaa gacttcagtt acctgtacct    780
ggattatctt tagctaaaga attatatgaa gaactaataa aagatggcga ggaaaattct    840
ggaacacaag tattatataa gaatatata gaggataa                             879
```

<210> SEQ ID NO 2
<211> LENGTH: 876
<212> TYPE: DNA
<213> ORGANISM: Artificial Sequences
<220> FEATURE:
<223> OTHER INFORMATION: LZ1561 codon adapted nucleotide sequence of pdMSR

<400> SEQUENCE: 2

```
atgaggatag gatttatagg attgggaaac atgggcggcc caatggcagc aaatttacta      60
aaggcaggat ttgacctatc agtatttgat ttatctgcta aagctgtagc tgcagcagta    120
gctttaggag ctagggcact tgcatctcca gctgaagtag caagagatga tgtagaagta    180
atcataacaa tgttacctgc tgctgcccat gtgaaacaag tatttcttgg tgaagatgga    240
ttattagcaa atgttcaacc tggtgtactt ttaattgata gttcaactat agatccatta    300
aatgctagag aagtgtctgc agctgcactt gcacatggaa tccaatgtt agatgctcct    360
gtttcaggcg gcactgctgg tgcagcagct ggtacactta cttttatggt tggcggcgaa    420
ccggcagatt ttgaaaggc tagaccagca ttagctgcta tgggaaaaaa tatagttcat    480
tgtggcggca ctggaaatgg acaagtagca aaagttgcaa ataatttgtt attaggtata    540
tcaatgatag gagtagcaga agcaatgagc ttaggtgtga agttaggcat ggatgctgat    600
gtactagctg gtataataaa tacatcaagt ggaagatgtt ggtcgtcaga agttaataat    660
cctttgaccg gagctccagc tgctagggc tattctggcg gctttggtac agatttgatg    720
ttaaaagatc ttggacttgc atctgaagca gcaagacagg taagacaacc agtattatta    780
ggtgctcttg cacaacaatt atttcaaact ttttcaaatc agggaaatgg acaattagac    840
tttagcgcta ttgttaagct ttatgaacag ggataa                              876
```

<210> SEQ ID NO 3
<211> LENGTH: 945
<212> TYPE: DNA
<213> ORGANISM: Artificial Sequences
<220> FEATURE:

<223> OTHER INFORMATION: LZ1561 codon adapted nucleotide sequence of nmMSR

<400> SEQUENCE: 3

```
atgcacacag taagaatacc aaaagttata aatttcggag aagatgcatt aggtcaaaca      60
gaatatccaa aaaatgcact agtagtaact acagtacctc ctgaactaag tgataaatgg     120
ttggcaaaaa tgggtattca agattatatg ttgtacgata aggtaaaacc agaaccatct     180
atagatgatg taaacacatt aataagtgag ttcaaagaaa agaaaccatc tgtgcttata     240
ggattaggcg gcggctcttc tatggatgtg gtaaaatatg cagcacagga ttttggagtt     300
gaaaagatat taattcctac aacttttggc acaggtgctg aaatgactac ttattgtgta     360
cttaaatttg atggaaagaa gaaactctta agagaagata gattccttgc agatatggca     420
gttgtagata gttattttat ggatggaact cctgaacagg taataaaaaa ttcagtatgt     480
gatgcttgtg cacaagcaac ggaaggttat gattctaaac taggtaatga tcttacaagg     540
acactgtgta agcaagcctt tgaaatttta tatgatgcaa taatgaatga taaaccagaa     600
aattatccgt atggttctat gttatcaggt atgggatttg gaaactgttc cactacatta     660
ggccatgctt tatcttacgt attcagtaat gaaggtgtac ctcacggata ttctttaagc     720
agctgtacta ctgtagctca taagcataat aaaaagcattt tttacgacag attcaaagag     780
gctatggata aacttggctt tgataagtta gaattaaagg ctgacgtcag tgaagcagca     840
gatgtagtaa tgactgacaa gggacattta gatcctaatc ctattccaat ttcaaaagac     900
gatgtagtta atgcttaga agatataaaa gcaggaaatc tctaa                      945
```

<210> SEQ ID NO 4
<211> LENGTH: 747
<212> TYPE: DNA
<213> ORGANISM: Artificial Sequences
<220> FEATURE:
<223> OTHER INFORMATION: LZ1561 codon adapted nucleotide sequence of ecMSR

<400> SEQUENCE: 4

```
atgatagtat tagtaacagg ggctacagca ggatttggag aatgcattac aagaagattt      60
atacagcaag gacacaaggt aatagctact ggcagacgac aagagagatt gcaagagtta     120
aaagatgaat tgggagataa tttatatata gctcaattgg atgtgagaaa tagggctgct     180
atagaagaaa tgcttgcttc cttaccagct gaatggtgta atatagatat tttagtaaat     240
aatgctggtc ttgcccttgg catggagcct gcccataagg cttccgtaga ggactgggag     300
acaatgatag atacaaataa taagggatta gtttatatga cacgtgctgt actccctggt     360
atggtggagc gcaaccacgg acatataata aatataggat caacagcggg ttcctggcct     420
tatgctggcg gcaatgttta tggtgctact aaagcatttg taagacaatt tctttaaat      480
cttagaacag accttcatgg tactgctgtt agagttacag atattgagcc aggattggta     540
ggcggcactg aatttagtaa tgtttagatt taagggagatg atggtaaggc tgaaaaaaca     600
taccaaaata ctgttgcttt aactcctgaa gatgtaagtg aagcagtttg gtgggtaagc     660
actttaccag ctcatgtaaa cataaataca ctagaaatga tgcctgttac tcaaagttat     720
gcaggattaa atgttcatag acagtaa                                          747
```

<210> SEQ ID NO 5
<211> LENGTH: 804
<212> TYPE: DNA
<213> ORGANISM: Artificial Sequences
<220> FEATURE:
<223> OTHER INFORMATION: LZ1561 codon adapted nucleotide sequence of scMSR

<400> SEQUENCE: 5

```
atgtcacaag gtagaaaagc agcagaaaga ttagcaaaga aaacagtact aataacagga      60
gcatcagcag gaataggaaa agctactgca cttgagtatc ttgaagcttc aaatggagat     120
atgaaattaa tattggcagc aagaaggctt gaaaaacttg aggaacttaa aaaaacaatt     180
gatcaagaat tccctaatgc taaagttcac gttgctcagc ttgatataac ccaggcagaa     240
aaaataaaac cattcattga aacttaccct caagaattca agatattga tatactggtt      300
aataatgcag gcaaggcttt aggttcagat agggtaggtc agatagctac tgaggatata     360
caagacgttt ttgatactaa tgtcacagct ctcattaata taacacaagc tgtgttacct     420
atatttcaag caaagaactc aggagatata gttaatctag atcaatagc aggaagagat      480
gcatatccta ctggaagtat atactgtgct tcaaaatttg cagtaggagc atttactgat     540
tctttaagaa aagaacttat aaatactaag ataagggtta tattaattgc tccagggctt     600
gtagaaacag aattttcact tgtaagatat agaggaaatg aagaacaagc taaaatgta      660
tataaggata ctactccatt aatggcagat gatgtagctg acttaatagt atatgctact     720
tcaagaaaac aaaatactgt tatagctgac acacttatat tcccaacaaa tcaggcttca     780
ccacatcata tatttagagg ataa                                            804
```

<210> SEQ ID NO 6
<211> LENGTH: 945
<212> TYPE: DNA
<213> ORGANISM: Artificial Sequences
<220> FEATURE:
<223> OTHER INFORMATION: LZ1561 codon adapted nucleotide sequence of msMSR

<400> SEQUENCE: 6

```
atgacagaaa aagtatcagt tgttggagca ggagttatag gagtaggatg ggcaacttta      60
tttgcatcaa aaggttacag tgtatcctta tatactgaaa agaaggaaac actagataaa     120
ggtattgaaa aactaagaaa ttatgttcag gttatgaaga caacagtca gataactgaa      180
gatgttaata cagtaataag tagagttagt cctaccacta atttagatga ggctgtaaga     240
ggtgctaact tgttatagga ggctgtaatt gaagattatg atgctaaaaa gaaaattttt     300
ggatacttgg attcagtatt agataaagaa gttatactag catcttcaac atctggactt     360
cttataaccg aagtacagaa agcaatgtct aagcatccag aaagggcagt aatagcacat     420
ccttggaatc caccacattt attacctttg gtagaaatag taccaggaga aaaaactagt     480
atggaagtag tagagagaac taaatctctt atggaaaaat tagatagaat agtagtagtt     540
ttaaagaaag aaattcctgg ttttatagga aatagacttg catttgcgct ttttagagag     600
gctgtttatt tagttgatga aggagttgcg acggtagaag atattgataa ggtaatgact     660
gcagctatag gtcttagatg ggcttttatg ggtccttttc ttacctacca tttaggcggc     720
ggcgaaggcg gcttggaata tttcttcaac agaggatttg gatatggtgc gaatgaatgg     780
atgcatacat tggcaaaata tgataaattt cctatactg gagttacaaa ggctattcaa     840
caaatgaaag aatattcatt tataaaggga aagaccttcc aggaaataag taaatggaga     900
gatgaaaaat tattaaaagt gtataaactt gtttgggaaa agtaa                    945
```

<210> SEQ ID NO 7

<211> LENGTH: 1650
<212> TYPE: DNA
<213> ORGANISM: Artificial Sequences
<220> FEATURE:
<223> OTHER INFORMATION: LZ1561 codon adapted nucleotide sequence of caMSR-N

<400> SEQUENCE: 7

```
atgagtggaa caggaagatt ggcaggaaaa atagcactaa taacaggcgg cgcaggaaat      60
ataggctcag aacttacaag aagattcctt gcagaaggtg ctacagtaat tatttcagga     120
agaaaccgtg ccaaattaac tgctttagct gaaagaatgc aggctgaagc aggagttcca     180
gcaaaaagaa tagatttgga agtaatggac ggatctgacc ctgttgcagt aagggcagga     240
atagaagcaa tagttgcaag acatggacaa attgacattc tagtaaacaa tgcaggaagt     300
gcaggagccc agagaagatt agctgaaatc ccattgactg aagcagaact tggaccaggt     360
gctgaagaaa cccttcatgc atctattgcc aatctattag gtatgggctg catcttatg     420
agaatagcag ctccacacat gccagttggt tctgcagtaa taaatgtgtc tactatatt     480
tcaagggctg aatattacgg aaggattcct tatgttacgc ctaaggctgc attaaatgcc     540
ctatcacagc ttgcagctag agaattaggg gcaagaggta ttagggtaaa tactattttc     600
ccaggaccaa ttgagtcgga taggattaga acagtatttc agagaatgga tcagttaaaa     660
ggtcgtcctg agggtgatac agcccatcac tttttaaata caatgaggct ttgtagagca     720
aatgatcaag gtgcactaga aagaagattt cctagtgtag agatgttgc agatgctgca     780
gtatttctgg catctgctga gtctgcagct ctcagcggtg aaactattga agtaactcat     840
ggtatggagt taccagcatg ttcagaaacc agcttacttg ccagaactga tcttagaact     900
atagatgcat ctggaagaac cactttaata tgtgctggtg atcagataga agaagtaatg     960
gctctaacag gaatgttaag aacctgtgga tcagaagtta taataggttt tagatcagca    1020
gcagctcttg cacaatttga acaggctgtt aatgagtcaa gaagattagc tggtgcggat    1080
tttactcctc ctattgcact tcctcttgat ccaagagatc cagcaactat cgatgctgta    1140
tttgattggg ctggtgaaaa tactggcggc attcatgctg ctgtaatact tccagcaact    1200
tcacatgagc cagcaccatg tgtaatagaa gtagatgatg aaagagtatt aaattttta    1260
gcagatgaaa taactggtac tatcgttata gcatcaagat tagctagata ttggcagagc    1320
cagagactta ccccagggc aagggcaaga ggaccaagta atattcct ttcaaatgga    1380
gcagatcaga acggtaatgt ttatggaagg attcaatcag ctgcaatagg tcagcttata    1440
agagtatgga gacatgaagc agagttggat tatcaaaggg cttcagcagc tggtgatcac    1500
gtacttcccc ctgtatgggc aaaccaaata gttagatttg caaacagatc tttagaagga    1560
ttagaatttg cttgtgcctg gacagctcaa ttgttgcatt tcaaagaca tataaatgaa    1620
ataactttaa atattcccgc caacatctaa                                     1650
```

<210> SEQ ID NO 8
<211> LENGTH: 411
<212> TYPE: DNA
<213> ORGANISM: Artificial Sequences
<220> FEATURE:
<223> OTHER INFORMATION: LZ1561 codon adapted nucleotide sequence of cgPAND

<400> SEQUENCE: 8

```
atgttaagaa ctatactagg cagtaaaata cacagggcaa cagttacaca agcagattta     60
gattatgtag gaagtgttac tatagatgca gatttggttc atgctgctgg gcttatagaa    120
```

```
ggagaaaaag ttgctattgt ggatattact aatggtgcta gactggaaac ttatgtaata      180
gtaggagatg caggaacagg aaatatatgt attaatggtg ctgctgcaca tcttattaat      240
ccaggagatc ttgtaataat aatgtcctac cttcaggcaa cagatgcaga agcaaaggca      300
tacgaaccta aaatagttca tgtagatgcc gataatagaa tagtagcatt gggaaatgat      360
ttagctgaag cactaccagg aagtggcctc cttacttcaa ggagtatcta a               411

<210> SEQ ID NO 9
<211> LENGTH: 384
<212> TYPE: DNA
<213> ORGANISM: Artificial Sequences
<220> FEATURE:
<223> OTHER INFORMATION: LZ1561 codon adapted nucleotide sequence of
      caPAND

<400> SEQUENCE: 9
atgcatttaa atatgttaaa aagtaaaata cacagagcaa cggtagtaca agcagatcta       60
aactatgtag gaagtataac tatagataga atcttatgg ataaagcaaa tatattggaa      120
tatgaaaaag tagaaattgc aaacattaac aatggagcaa gatttgagac ttatgtaata      180
gctggagaag caggctcagg aataatatgc ttaaatggtg cagcagcccg ctgtgcacag      240
gctggggata agttattat aatgtgttat tgttctttaa caccagaaga ggcttcagaa      300
catagaccaa aagtagtatt tgtaaacgat gataacagta tttctaatgt aacagaatat      360
gaaaagcatg gcactatagg ataa                                             384

<210> SEQ ID NO 10
<211> LENGTH: 381
<212> TYPE: DNA
<213> ORGANISM: Artificial Sequences
<220> FEATURE:
<223> OTHER INFORMATION: LZ1561 codon adapted nucleotide sequence of
      ecPAND

<400> SEQUENCE: 10
atgataagaa caatgttaca aggaaaacta catagggtaa aggtaacaca cgcagatcta       60
cattatgaag gaagctgtgc aattgatcag gatttcctag atgccgctgg tatacttgaa      120
aatgaagcaa tagatatttg gaatgtaaca aacggaaaaa gatttagtac ctatgctatt      180
gctgctgaaa gaggaagcag aataatatct gtaaatggtg ctgctgcgca ttgtgcaagt      240
gttggagata ttgttataat tgcatcattt gttactatgc ctgatgaaga ggctagaacc      300
tggcgaccta acgtagctta ttttgaaggt gataatgaaa tgaaacgcac ggcaaaagca      360
attccagtac aagttgccta a                                                381

<210> SEQ ID NO 11
<211> LENGTH: 1623
<212> TYPE: DNA
<213> ORGANISM: Artificial Sequences
<220> FEATURE:
<223> OTHER INFORMATION: LZ1561 codon adapted nucleotide sequence of
      tcPAND

<400> SEQUENCE: 11
atgcctgcta caggagaaga tcaagattta gtacaagact aatagaaga accagcaaca       60 tttagtgacg cagtactaag ctctgatgaa gaacttttcc accagaaatg tcctaaacct      120
gctcctattt atagtccagt aagtaaacct gtatcctttg aatcattacc aaacagaaga      180
ttgcatgaag agttccttag aagcagtgtt gatgtacttc tccaagaggc tgtatttgaa      240
```

```
ggaactaata ggaaaaatag agttttacaa tggagagaac ctgaagaact tcgtagatta    300
atggactttg gggtaagatc agctccttct actcatgaag aattgcttga agtactcaaa    360
aaagttgtta cctacagtgt taaaacagga catccttatt ttgtaaatca gttattttca    420
gcagtagatc cttatggatt agtagcacag tgggctacag atgcgttaaa tccatctgta    480
tatacttatg aagtaagccc tgtatttgta cttatggaag aagttgtttt gagagaaatg    540
agggctattg taggatttga aggcggcaaa ggtgacggaa tattctgccc aggcggcagt    600
atagctaatg gttatgctat atcctgtgct agatatcgtt ttatgcctga tataaagaag    660
aaaggattac attcattacc aagacttgta ttatttacaa gtgaagatgc tcattattct    720
ataaaaaaac ttgcttcctt ccagggtata ggtactgaca atgtttatct tataagaaca    780
gatgcaagag aagaatgga tgtgtctcat ctggtagaag aaatagaaag aagtcttaga    840
gaaggtgctg caccgttcat ggtaagtgct acagcaggaa caactgtaat aggagcattt    900 gacccaaatag aaaaaattgc ggatgtttgc caaaaatata agttatggct tcatgttgat    960
gctgcatggg gcggcggcgc acttgtatca gcaaacata gacatctttt gaagggaata   1020
gaacgtgcag attctgtaac ttggaatcca cataaattac ttacagctcc tcagcaatgc   1080
tcaactttat tgttaagaca tgagggagta cttgctgagg ctcattctac taatgcagct   1140
tatcttttcc aaaagataa attttatgat acaaaatacg atacaggaga taagcatatc   1200
caatgtggaa gaagagcaga tgtacttaaa ttctggttca tgtggaaagc aaaaggaaca   1260
tctggacttg aaaaacatgt agataaagta ttgaaaatg ctagattctt tacggattgt   1320
ataaaaaata gagaaggatt tgaaatggtt atagcagaac ctgaatatac aaatatttgt   1380
ttctggtatg tacctaaatc tctcagaggt agaaaggatg aagcagatta taagacaaa   1440 ttacataaag tagcaccaag aataaaggag agaatgatga agagggaag tatgatggta   1500 acttatcagg ctcaaaaggg acacccaaac ttctttagaa tagtatttca aaatagtgga   1560
ctggataaag cagatatggt tcatcttgtt gaagaaatcg agagattagg ctcagatctc   1620
taa                                                                 1623
```

<210> SEQ ID NO 12
<211> LENGTH: 1191
<212> TYPE: DNA
<213> ORGANISM: Artificial Sequences
<220> FEATURE:
<223> OTHER INFORMATION: LZ1561 codon adapted nucleotide sequence of mjPAND

<400> SEQUENCE: 12

```
atgagaaata tgcaagaaaa gggagtatca gaaaaagaaa tattggaaga attaaaaaaa     60
tacagaagtt tggatttgaa gtatgaagat ggaaatatat ttggaagtat gtgtagtaat    120
gttcttccaa taacacgtaa aatagtagat atatttttag aaacaaatct tggtgatcca    180
ggactattca aaggaactaa gttactggaa gaaaaggcag tagcgttgct tggttcctta    240
ttaaataata aagatgccta tggacatata gtttctggcg gcactgaagc aaatttgatg    300
gcacttagat gtataaaaaa tatctggaga gaaaagagaa gaagggatt aagtaaaaat    360 gaacatccta aaataatagt tcctataact gcacatttt catttgaaaa aggaagagaa    420
atgatggact agaatacat ttatgcaccg atcaaagaag attataccat agatgaaaaa    480
tttgttaaag atgccgtaga agattatgat gttgacggta ttataggtat agcaggcaca    540
actgaacttg gaactataga caatatagag gaattatcca aaatcgctaa agaaaataat    600
```

```
atatatatcc atgtagatgc tgcatttggc ggcttagtaa taccattcct tgatgacaaa      660
tacaagaaaa agggagttaa ctataaattt gactttcac ttggagtaga ttctataacc       720
atagatccac acaagatggg acattgtcct attccatcag gcggcatatt gttcaaagat      780
ataggttata aaagatatct ggatgttgat gctccttatc tcactgagac tagacaggct      840
actattttag gaacacgtgt aggttttggc ggcgcttgta cctatgcagt tcttagatat      900
cttggaagag aaggacagag aaaaatagtt aatgaatgta tggagaatac actatatctc      960
tacaaaaaac ttaagaaaa taatttcaaa ccagttatag aacctatatt aaatatagtt      1020
gctatagaag atgaggatta taagaagtt tgcaaaaagt taagagatcg tggaatatat      1080
gtaagtgttt gtaattgtgt aaaggcttta aggattgttg taatgcctca catcaagaga      1140
gaacatattg ataatttcat tgaaatctta aattccataa aaagggacta g              1191
```

<210> SEQ ID NO 13
<211> LENGTH: 1347
<212> TYPE: DNA
<213> ORGANISM: Artificial Sequences
<220> FEATURE:
<223> OTHER INFORMATION: LZ1561 codon adapted nucleotide sequence of
      paBAPAT

<400> SEQUENCE: 13

```
atgaatcagc cactaaatgt tgccccacca gtttcatcag aacttaattt aagagcccat        60
tggatgccat tttcagccaa tagaaacttt caaaaagatc caaggattat agtagcagct       120
gaaggttctt ggcttactga tgacaagggt agaaaagtat acgattcact ttcaggacta       180
tggacatgcg gtgctggtca ttcaagaaaa gaaatacagg aagcagttgc tagacagctt       240
ggtactttgg attatagtcc tggatttcaa tatggacacc cactttcctt tcaactggca       300
gaaaaaatag ctggattact tcctggtgag ctgaaccatg tattctttac aggtagcggt       360
tcagaatgtg cagatacttc aataaaaatg gcaagggctt attggagact caaaggtcag       420
cctcaaaaaa ctaaacttat aggacgtgcc agaggatatc atggtgtaaa tgtggcagga       480
acatctttag gcggcatagg cggcaataga aaaatgttcg gtcaattaat ggatgtagat       540
catttaccac atacacttca gccaggtatg gcatttacta gaggaatggc acagacaggc       600
ggcgtagaat tagctaatga attattgaaa ttgatagaac tccatgatgc ttctaacata       660
gcagctgtca ttgtagaacc tatgtctggt tcagctgggg tccttgttcc tccagtagga       720
tatttgcaaa gactacgtga aatttgtgat caacacaata tattgctaat atttgatgag       780
gtaataactg cttttggaag gctaggaact tattcaggag cagagtactt tggagtaact       840
cctgatctta tgaatgtagc aaaacaagta acgaatggtg ctgtacctat gggtgctgtc       900
atagcatcat cagaaattta cgatacattc atgaaccaag cactgcctga acatgcagta       960
gaattttcac atggttatac ttatagtgcc catccagtag catgtgcagc tggactggca      1020
gcattagata ttcttgcaag ggacaatctt gtacaacaaa gtgctgaatt agctcctcac      1080
tttgaaaagg gacttcatgg acttcaaggt gcaaaaatg tcatagatat aagaaactgt      1140
ggacttgctg gtgctataca aattgcacca agagatggtg accctacagt aagaccttt       1200 gaagcaggaa tgaactttg caacagggga ttctatgtaa gatttggcgg cgatacttta       1260
caatttggac ctacatttaa tgctagacca gaggaattag atagattatt tgatgcagtt       1320
ggagaggcat taaatggtat agcctaa                                          1347
```

```
<210> SEQ ID NO 14
<211> LENGTH: 1356
<212> TYPE: DNA
<213> ORGANISM: Artificial Sequences
<220> FEATURE:
<223> OTHER INFORMATION: LZ1561 codon adapted nucleotide sequence of
      bcBAPAT

<400> SEQUENCE: 14
atggaattaa tgatagtaca ggtaacagaa cagactcaat cacttaaaaa gacagacgaa      60
aaatatttat ggcatgctat gcgtggtgct gctccttcac caacaaatct tataattaca     120
aaggctgaag gtgcgtgggt tacggatatt acggaaaca gatatttaga tggaatgagt      180
ggactttggt gcgtaaatgt tggttatgga agaaaggaat tggctagagc agcattcgaa     240
cagttagaag aaatgcctta ttttcctctt actcaatctc atgtacctgc tataaaatta     300
gctgaaaaat tgaatgaatg ccttgatgat gaatatgtaa tattcttttc aaattcaggt     360
tctgaagcaa acgaaacagc ctttaagata gcaagacaat atcatcaaca aaaggagat      420 catggaagat ataaatttat aagcagatat agggcttatc atggtaattc tatgggagcc     480
ttggcagcta caggccaagc ccagagaaag tacaaatatg aaccacttgg acaaggattt     540
cttcacgttg ctcctcctga tacttataga atcctgaag atgttcacac acttgcgtct     600
gctgaagaaa tcgacagagt tatgacttgg gaattatctc aaacagttgc tggtgttatt     660
atggaaccta ataacagg cggcggcatt ttaatgccac cagatggtta tatggaaaaa      720
gttaaagaga tatgtgaaaa acatggtgct ttattaatct gcgatgaagt aatatgtgga     780 tttgaagaa ctggaaagcc tttttggcttt atgaactatg gagttaaacc agatataata      840
acaatggcaa aaggtattac aagtgcctat cttcctttat ctgctacagc agtaagaaga     900
gaagtatatg aagcatttgt aggaagcgat gattatgata gatttagaca tgtaaatact     960
tttggcggca atcctgctgc atgtgcttta gctttaaaaa atttagaaat tatggaaaac    1020
gaaaaactca ttgaaagatc aaaggaatta ggcgaaagac tcctttacga gcttgaggat    1080
gtaaaagaac acccaaatgt tggggatgtt agaggaaaag acttttgct aggtatagaa      1140 ctagtagagg acaagcaaac taagaaacct gcttctatag agaaaatgaa taagtaata     1200 aatgcgtgca agaaaaagg gcttataatt ggtaaaaatg gtgacactgt tgctggatat     1260
aacaatatat tgcaattagc accaccatta tccataaccg aagaagattt tacatttata    1320
gttaagacaa tgaaagagtg ccttgcacag ctctaa                               1356

<210> SEQ ID NO 15
<211> LENGTH: 1347
<212> TYPE: DNA
<213> ORGANISM: Artificial Sequences
<220> FEATURE:
<223> OTHER INFORMATION: LZ1561 codon adapted nucleotide sequence of
      ppBAPAT

<400> SEQUENCE: 15
atgaacatgc cagagacagg accagcagga atagcaagcc aattaaaact agatgcacat      60
tggatgcctt atacagctaa tagaaacttt caaagagatc caagacttat agtagctgca     120
gaaggaaact atttagtaga tgatcatgga agaaaaatat ttgatgcact aagtgggctt     180
tggacttgtg gagcaggaca cacaagaaag gaaatagctg atgcagtaac aagacaattg     240
tcaacactag attattctcc agcatttcaa tttggacatc ctttgtcttt ccagcttgca     300
gaaaaaattg ctgaattagt tcccggtaat ttaaatcatg tattttacac taacagtgga     360
```

```
tcagaatgtg ctgatacagc actaaaaatg gtaagggctt attggagact taaaggtcag     420
gctactaaga ccaagataat cggaagggct agagggtatc atggagtaaa tatagcagga     480
acttccttag gcggcgtgaa tggcaataga aaaatgttcg gacaattatt agatgttgac     540
catctgccac atacagtttt gccagtaaat gcattttcaa aaggcttacc agaagaaggc     600
ggcatagcac tagcagatga aatgctaaaa ttaattgaat tacatgatgc atctaacatt     660
gcagctgtta tagtggaacc acttgctgga tcagcaggag ttcttcctcc tcctaaggga     720
tacttaaaga ggttaagaga aatatgtact cagcacaata ttttacttat atttgacgaa     780
gttataacag gatttggaag aatgggagca atgacaggaa gtgaggcttt tggtgtaact     840
cctgatttaa tgtgcattgc aaagcaagtt acaaacggtg ctataccaat gggtgctgta     900
atagcatctt cagagatcta ccaaacattt atgaaccaac caactcctga gtatgcagta     960
gagttccctc atggatacac ttactcagct catcctgttg cttgtgcagc tgggcttgca    1020
gcacttgatc ttctgcaaaa agaaaattta gttcaaagtg cagcagaact tgccccacat    1080
tttgaaaaat tactacatgg tgtaaaagga acaaaaaata ttgttgacat tagaaactat    1140
ggattagctg ggcaataca gatagctgct agagatggag atgcaatagt aaggccatac    1200
gaggctgcaa tgaaattatg gaaggcagga ttctatgtta gatttggcgg cgatacatta    1260
caatttggac caactttcaa tactaaacca caggaactag atcggttatt tgatgctgtt    1320
ggagagactt tgaaccttat tgactag                                        1347
```

<210> SEQ ID NO 16
<211> LENGTH: 1428
<212> TYPE: DNA
<213> ORGANISM: Artificial Sequences
<220> FEATURE:
<223> OTHER INFORMATION: LZ1561 codon adapted nucleotide sequence of
      skGABT

<400> SEQUENCE: 16

```
atgccaagtt acagtgttgc agaactatat tatccagatg aaccaacaga accaaaaata      60
tctactagct cttaccctgg tccaaaggct aagcaagaac ttgaaaaatt aagtaatgtt     120
ttcgatacta gagctgctta tttactagca gattattata agagtagggg caattatatt     180
gttgatcagg atggaaatgt acttcttgat gtttatgccc aaatatcttc tatagcttta     240
ggctataaca atccagaaat cttaaaagtt gctaagtctg atgcaatgtc tgttgcctta     300
gccaatagac cagcacttgc ttgtttccca tctaatgatt atggtcagct cttggaagat     360
ggacttctta agctgcacc acaaggacaa gataagattt ggactgcttt atctggaagt     420
gatgccaatg aaactgcatt taaggcatgc tttatgtacc aagcagctaa aagaggaat      480 ggaagaagtt tttcaacaga gaacttgaa agcgttatgg ataatcagct ccctggtact     540
tctgaaatgg taatttgttc ttttgaaaag ggattccatg aaggctttt tggaagctta     600 tccactacta gaagtaaacc aattcacaaa ttagacatac ctgctttcaa ctggcctaaa     660 gctccttttcc cagattaaaa atatcctcta gaagaaaata aggaagccaa taggcagaa     720 gaatcaagtt gtatagaaaa attttctcaa atagttcaag aatggcaagg taaaatagca     780
gctgttataa tagagcctat acagagtgaa ggcggcgata atcatgcatc aagtgatttt     840
tttcaaaagc ttagagaaat tacaattgaa aatggtatat tgatgatagt agacgaagtt     900
caaaccggtg taggagcaac aggtaaaatg tgggctcatg agcactggaa tctttcaaac     960
cccccagatt tagttaccct ttcaaaaaaa ttccaagctg ctggttttta ctatcatgat    1020
```

```
cctaaattac aacctgatca gcctttcaga caatttaata cctggtgtgg tgacccatca    1080
aaggcactta tagctaaggt tatttatgaa gaaattgtaa acatgactt agttacaagg     1140 acagctgaag taggaaatta tctatttaat aggttagaaa agttatttga aggaaagaac    1200
tatattcaaa atttgagagg aaagggacag ggaacttata tagcatttga ttttggtact    1260
tcatctgaaa gggattcttt cctatcaaga ttaagatgta acggtgctaa tgtagctggg    1320
tgtggagatt cagctgtaag attgaggcct tcacttacct ttgaagaaaa gcatgcagat    1380
gttttagttt ctatatttga taaaactctt agacaattgt atggataa                1428
```

```
<210> SEQ ID NO 17
<211> LENGTH: 1251
<212> TYPE: DNA
<213> ORGANISM: Artificial Sequences
<220> FEATURE:
<223> OTHER INFORMATION: LZ1561 codon adapted nucleotide sequence of
      pgAAM

<400> SEQUENCE: 17
atggcagaat caagaagaaa gtattatttc cctgatgtaa ctgatgaaca atggtatgat    60
tggcactggc aagttctaaa tagaatcgag acactagatc aattaaaaaa atatgttact   120
ttaactgcag aagaagaaga aggagtaaaa gaaagcccta agtactcag gatggctata   180 actccttatt atctatcatt aatagatcca gaaaacccaa attgtccaat tagaaagcaa    240
gcaatacctt actcagcaag acttgtacgt gcccctgaag atcaagtaga tcctctaagt    300
gaagatgacg attcaccagt accagggtta actcatagat atcctgatag ggtactgttc    360
cttattactg ataaatgctc aatgtattgt agacattgta caagaagaag atttgctggt    420
caaaaagatg cttcttcacc aagtgaaagg atagatagat gcatagatta tatagcaaat    480
accccaaccg ttagagatgt tttattgtct ggcggcgatg ctttacttgt atctaatgaa    540
agacttgaat acatttttaaa gagattaaga gagataccct catgtagaaat aataagaata    600 ggttcaagaa ctcctgtagt acttcctcaa agaataactc cacagttagt ggatatgtta    660
aaaaagtatc atccagtatg gcttaatact cactttaacc acccaaatga agtaacagaa    720
gaggctgtag aggcatgtga gagaatggct aatgctggca ttccattagg caatcagaca    780
gttttgctca ggggaataaa tgactgtact catgttatga aagattagt tcatcttttg    840 gttaaaatga gagtgaggcc ttattatata tatgtatgtg atctttcact tggaataggc    900 catttttagaa ctcctgtatc aaaaggcata gaaattattg aaaatcttcg tggtcatact    960
agtggatatg ccgtacctac atttgtagtt gggggcaccag gcggcggcgg caaaattcct   1020
gttactccaa attatgtagt aagtcagtca ccaagacatg tagttttaag aaattatgaa   1080
ggtgttataa ctacttacac agaaccagaa aactatcatg aagaatgtga ttgtgaagat   1140
tgtagggctg gaaaacataa ggaaggagtt gctgcattga gtggcggcca acagcttgca   1200
atagaaccat ctgatttagc caggaagaag agaaaatttg ataaaaacta g            1251
```

```
<210> SEQ ID NO 18
<211> LENGTH: 1416
<212> TYPE: DNA
<213> ORGANISM: Artificial Sequences
<220> FEATURE:
<223> OTHER INFORMATION: LZ1561 codon adapted nucleotide sequence of
      bsAAM

<400> SEQUENCE: 18
atgaaaaata atggtataaa acctaaaaga cactggaagg aaattgaatt atggaaagat    60
```

```
gtacctgagg aaaagtggaa tgattggttg tggcaattga cccacacagt gaggacatta    120
gatgatttaa aaaaggtaat taatcttaca gaagatgaag aagaaggtgt aaggattagt    180
accaagacaa tacctttaaa tataactcct tattatgcaa gccttatgga ccctgacaat    240
ccaagatgtc cagtgagaat gcaatcagta ccattaagtg aagaaatgca taaaactaaa    300
tatgatatgg aagatcctct tcatgaagat gaagatagtc ctgttcctgg attaactcat    360
agatatcctg acagagtttt attcctcgta acaaaccaat gttcagtata ttgtagatat    420
tgtactagaa gaagattttc tggacaaata ggaatgggag ttcctaaaaa acaattagat    480
gcagctatag catacataag agaaactcca gaaatacgcg actgcctcat atcaggcggc    540
gatggattac taataaatga ccaaatatta gagtacatac ttaaagaatt aagatcaata    600
cctcatttgg aagtaataag aataggtaca agggctcctg ttgtattccc acagagaata    660
acagatcatc tgtgtgacat attaaagaaa tatcatccag tctggttaaa tacacatttt    720
aacacttcaa ttgaaatgac agaagaatct gtagaggctt gtgaaaaatt agtaaatgcg    780
ggtgtacctg ttggtaatca ggcagttgta cttgcgggca ttaacgattc agtaccaata    840
atgaagaaat taatgcatga tttggtaaaa ataagggtaa gaccttatta tatatatcag    900 tgtgatctttt cagaaggcat aggacacttt agggcaccag tatcaaaggg cttagagatt    960
attgaaggat taagaggaca cacttcagga tatgcagtac caacttttgt agtccatgca   1020
ccaggcggcg gcggcaaaat tgcattacag ccaaattatg tattgtcaca gtcaccagat   1080
aaagttatat tgagaaactt cgaaggtgta ataacaagtt acccagagcc agaaaattat   1140
attcctaatc aggcagatgc atactttgaa tctgtattcc cagaaactgc tgataagaaa   1200
gaaccaattg gcttaagtgc tatatttgct gataaagaag tatcttttac tccagaaaat   1260
gtagatagaa taaaagaag agaggcatac atagctaatc cagaacatga aactctaaag   1320
gatagaagag aaaaaagaga tcaattaaaa gaaaagaagt tccttgcaca acaaaaaaaa   1380
caaaaggaaa ctgaatgcgg cggcgattcc tcctaa                             1416
```